US012570965B2

(12) United States Patent
Livore et al.

(10) Patent No.: US 12,570,965 B2
(45) Date of Patent: Mar. 10, 2026

(54) HERBICIDE-RESISTANT RICE PLANTS, POLYNUCLEOTIDES ENCODING HERBICIDE-RESISTANT ACETOHYDROXYACID SYNTHASE LARGE SUBUNIT PROTEINS, AND METHODS OF USE

(75) Inventors: Alberto Livore, Entre Rios (AR);
Alberto Raul Prina, de Buenos Aires (AR); Bijay K. Singh, Cary, NC (US);
Robert Ascenzi, Cary, NC (US);
Sherry R. Whitt, Raleigh, NC (US)

(73) Assignee: INSTITUTO NACIONAL DE TECHNOLOGIA AGROPECUARIA, Buenos Aires (AR)

( * ) Notice: Subject to any disclaimer, the term of this patent is extended or adjusted under 35 U.S.C. 154(b) by 34 days.

(21) Appl. No.: 11/816,884

(22) PCT Filed: Feb. 28, 2006

(86) PCT No.: PCT/US2006/007343

§ 371 (c)(1),
(2), (4) Date: Sep. 9, 2009

(87) PCT Pub. No.: WO2006/094084

PCT Pub. Date: Sep. 8, 2006

(65) Prior Publication Data

US 2010/0029485 A1      Feb. 4, 2010

Related U.S. Application Data

(60) Provisional application No. 60/657,968, filed on Mar. 2, 2005.

(51) Int. Cl.
*C12N 15/82*      (2006.01)
*C12N 9/10*       (2006.01)
*C12N 9/88*       (2006.01)

(52) U.S. Cl.
CPC ............. *C12N 9/1022* (2013.01); *C12N 9/88* (2013.01); *C12N 15/8278* (2013.01)

(58) Field of Classification Search
CPC ........................ C12N 15/8278; C12N 15/8274
See application file for complete search history.

(56) References Cited

U.S. PATENT DOCUMENTS

| | | | |
|---|---|---|---|
| 4,443,971 | A | 4/1984 | Chaleff |
| 4,761,373 | A | 8/1988 | Anderson et al. |
| 4,774,381 | A | 9/1988 | Chaleff et al. |
| 5,013,659 | A | 5/1991 | Bedbrook et al. |
| 5,084,082 | A | 1/1992 | Sebastian |
| 5,116,402 | A | 5/1992 | Dutka et al. |
| 5,141,870 | A | 8/1992 | Bedbrook et al. |
| 5,198,599 | A | 3/1993 | Thill |
| 5,304,732 | A | 4/1994 | Anderson et al. |
| 5,331,107 | A | 7/1994 | Anderson et al. |

| | | | |
|---|---|---|---|
| 5,378,824 | A | 1/1995 | Bedbrook et al. |
| 5,478,789 | A | 12/1995 | Hattori et al. |
| 5,478,798 | A | 12/1995 | Mayer et al. |
| 5,488,029 | A | 1/1996 | Hamprecht et al. |
| 5,539,092 | A | 7/1996 | Haselkorn et al. |
| 5,545,822 | A | 8/1996 | Croughan |
| 5,595,890 | A | 1/1997 | Newton et al. |
| 5,597,717 | A | 1/1997 | Guerireau et al. |
| 5,605,011 | A | 2/1997 | Bedbrook et al. |
| 5,633,437 | A | 5/1997 | Bernasconi et al. |
| 5,633,444 | A | 5/1997 | Guerineau et al. |
| 5,643,779 | A | 7/1997 | Ehrlich et al. |
| RE35,661 | E | 11/1997 | Thill |
| 5,718,079 | A | 2/1998 | Anderson et al. |
| 5,719,046 | A | 2/1998 | Guerieneau et al. |
| 5,731,180 | A | 3/1998 | Dietrich |
| 5,736,629 | A | 4/1998 | Croughan |
| 5,767,361 | A | 6/1998 | Dietrich |
| 5,767,366 | A | 6/1998 | Sathaswan et al. |
| 5,773,702 | A | 6/1998 | Penner et al. |
| 5,773,703 | A | 6/1998 | Croughan |
| 5,773,704 | A | 6/1998 | Croughan |
| 5,821,126 | A | 10/1998 | Durzan |
| 5,853,973 | A | 12/1998 | Kakefuda et al. |
| 5,858,652 | A | 1/1999 | Laffler et al. |

(Continued)

FOREIGN PATENT DOCUMENTS

| | | |
|---|---|---|
| CA | 1335412 | 3/1988 |
| CA | 2340282 | 10/2001 |

(Continued)

OTHER PUBLICATIONS

Ashigh et al 2007 Weed Science 55: 558-565.*
Kolkman et al 2004, Theoretical and Applied Genetics 109: 1147-1159.*
Okuzaki et al, Chimeric RNA/DNA oligonucleotide-directed gene targeting in rice, Plant Cell Rep. (2004, published online Nov. 21, 2003) 22:509-512.*
Tan et al, Pest Manag. Sci. (2005) 61:246-257, published online on Dec. 31, 2004.*
Battista, May 2002, Better Crops International vol. 16, Special Supplement, pp. 41-42.*

(Continued)

*Primary Examiner* — Mykola V. Kovalenko
(74) *Attorney, Agent, or Firm* — Lowenstein Sandler LLP

(57)      ABSTRACT

Herbicide-resistant rice plants, isolated polynucleotides that encode herbicide resistant and wild-type acetohydroxy-acid synthase large subunit 1 (AHASL1) polypeptides, and the amino acid sequences of these polypeptides, are described. Expression cassettes and transformation vectors comprising the polynucleotides of the invention, as well as plants and host cells transformed with the polynucleotides, are described. Methods of using the polynucleotides to enhance the resistance of plants to imidazolinone herbicides, and methods for controlling weeds in the vicinity of herbicide-resistant plants are also described.

19 Claims, 14 Drawing Sheets

Specification includes a Sequence Listing.

(56) References Cited

U.S. PATENT DOCUMENTS

| | | | |
|---|---|---|---|
| 5,859,348 A | 1/1999 | Penner et al. | |
| 5,876,932 A | 3/1999 | Fischer | |
| 5,928,937 A | 7/1999 | Kakefuda et al. | |
| 5,952,553 A | 9/1999 | Croughan | |
| 6,043,196 A | 3/2000 | Mayer et al. | |
| 6,100,030 A | 8/2000 | McCasky Feazel et al. | |
| 6,114,116 A | 9/2000 | Lemieux et al. | |
| 6,175,065 B1 | 1/2001 | Schmidt et al. | |
| 6,207,425 B1 | 3/2001 | Liu et al. | |
| 6,211,438 B1 | 4/2001 | Anderson et al. | |
| 6,211,439 B1 | 4/2001 | Anderson et al. | |
| 6,222,100 B1 | 4/2001 | Anderson et al. | |
| 6,225,105 B1 | 5/2001 | Sathasivan et al. | |
| 6,274,796 B1 | 8/2001 | Croughan | |
| 6,339,184 B1 | 1/2002 | Smith | |
| 6,348,643 B1 | 2/2002 | Kakefuda et al. | |
| 6,358,686 B1 | 3/2002 | Lemieux et al. | |
| 6,475,736 B1 | 11/2002 | Stanton, Jr. | |
| 6,492,582 B2 | 12/2002 | Johnson | |
| 6,613,963 B1 | 9/2003 | Gingera et al. | |
| 6,627,401 B2 | 9/2003 | Ralhan | |
| 6,696,294 B1 | 2/2004 | Konzak | |
| 6,943,280 B2 | 9/2005 | Croughan | |
| 7,019,196 B1 | 3/2006 | Croughan | |
| 7,345,221 B2 | 3/2008 | Croughan | |
| 7,399,905 B2 | 7/2008 | Croughan | |
| 7,495,153 B2 | 2/2009 | Croughan | |
| 7,595,177 B2 | 9/2009 | Barnes et al. | |
| 7,754,947 B2 | 7/2010 | Croughan | |
| 7,786,360 B2 | 8/2010 | Linscombe | |
| 7,807,882 B2 | 10/2010 | Leon et al. | |
| 2001/0044939 A1 | 11/2001 | Abell et al. | |
| 2002/0120962 A1 | 8/2002 | Charne et al. | |
| 2002/0138866 A1 | 9/2002 | Gingera et al. | |
| 2002/0138881 A1 | 9/2002 | Charne et al. | |
| 2003/0096277 A1 | 5/2003 | Chen | |
| 2003/0097692 A1 | 5/2003 | Jander et al. | |
| 2003/0138780 A1 | 7/2003 | Gill et al. | |
| 2003/0180929 A1 | 9/2003 | Kafefuda et al. | |
| 2003/0217381 A1 | 11/2003 | Croughan | |
| 2003/0236208 A1* | 12/2003 | Kmiec et al. | 514/44 |
| 2004/0142353 A1 | 7/2004 | Cheung et al. | |
| 2004/0171027 A1 | 9/2004 | Barnes et al. | |
| 2004/0172729 A1 | 9/2004 | Moldenhauer et al. | |
| 2004/0187178 A1 | 9/2004 | Slinkard et al. | |
| 2004/0219675 A1 | 11/2004 | Sainz et al. | |
| 2004/0237134 A1 | 11/2004 | Pozniak et al. | |
| 2004/0244080 A1 | 12/2004 | Hucl | |
| 2005/0044597 A1 | 2/2005 | Konzak | |
| 2005/0198705 A1 | 9/2005 | Croughan | |
| 2005/0208506 A1 | 9/2005 | Zhao et al. | |
| 2005/0283858 A1 | 12/2005 | Yao et al. | |
| 2006/0010514 A1 | 1/2006 | Birk et al. | |
| 2006/0095992 A1 | 5/2006 | Bowran et al. | |
| 2007/0028318 A1 | 2/2007 | Livore et al. | |
| 2007/0033670 A1 | 2/2007 | Konzak et al. | |
| 2007/0118920 A1 | 5/2007 | Leon et al. | |
| 2008/0167186 A1 | 7/2008 | Croughan | |
| 2008/0276329 A1 | 11/2008 | Moldenhauer | |
| 2009/0025108 A1 | 1/2009 | Croughan | |

FOREIGN PATENT DOCUMENTS

| | | |
|---|---|---|
| EP | 0154204 | 11/1985 |
| EP | 0257993 | 3/1988 |
| EP | 0360750 | 3/1990 |
| EP | 0364580 | 4/1990 |
| EP | 0375875 | 7/1990 |
| EP | 0461355 | 12/1991 |
| EP | 0502588 | 9/1992 |
| EP | 0508161 | 10/1992 |
| EP | 0525384 | 2/1993 |
| EP | 1754786 | 4/1996 |
| EP | 0730030 | 9/1996 |
| EP | 0965265 | 12/1999 |
| EP | 1033405 | 9/2000 |
| WO | WO199014000 | 11/1990 |
| WO | WO199113159 | 9/1991 |
| WO | WO199208794 | 5/1992 |
| WO | WO199633270 | 10/1996 |
| WO | WO199741218 | 11/1997 |
| WO | WO199802526 | 1/1998 |
| WO | WO199802527 | 1/1998 |
| WO | WO199832706 | 7/1998 |
| WO | WO199919493 | 4/1999 |
| WO | WO199953081 | 10/1999 |
| WO | WO199965292 | 12/1999 |
| WO | WO199965314 | 12/1999 |
| WO | WO200026390 | 5/2000 |
| WO | WO200027182 | 5/2000 |
| WO | WO200053763 | 9/2000 |
| WO | WO200121821 | 3/2001 |
| WO | WO200165922 | 9/2001 |
| WO | WO 01/84970 A2 * | 11/2001 |
| WO | WO 01/85970 A2 | 11/2001 |
| WO | WO200182685 | 11/2001 |
| WO | WO200183818 | 11/2001 |
| WO | WO200185970 | 11/2001 |
| WO | WO200192512 | 12/2001 |
| WO | WO200200915 | 1/2002 |
| WO | WO200208794 | 1/2002 |
| WO | WO2002092820 | 11/2002 |
| WO | WO2003012115 | 2/2003 |
| WO | WO2003013225 | 2/2003 |
| WO | WO2003014356 | 2/2003 |
| WO | WO2003014357 | 2/2003 |
| WO | WO2003076574 | 9/2003 |
| WO | WO2004007691 | 1/2004 |
| WO | WO2004016073 | 2/2004 |
| WO | WO2004022715 | 3/2004 |
| WO | WO2004040012 | 5/2004 |
| WO | WO2004106529 | 12/2004 |
| WO | WO2005020673 | 3/2005 |
| WO | WO2005093093 | 10/2005 |
| WO | WO2006007373 | 1/2006 |
| WO | WO2006024351 | 3/2006 |
| WO | WO2006060634 | 6/2006 |
| WO | WO2006094084 | 9/2006 |
| WO | WO2007005581 | 1/2007 |
| WO | WO2007032807 | 3/2007 |
| WO | WO2007140451 | 12/2007 |
| WO | WO2008124495 | 10/2008 |
| WO | WO2009046334 | 4/2009 |

OTHER PUBLICATIONS

U.S. Appl. No. 10/569,576, 2007-0028318, filed Feb. 1, 2007.
U.S. Appl. No. 13/420,958, 2012-0172224, filed Jul. 5, 2012.
U.S. Appl. No. 13/418,018, 2012-0233723, filed Sep. 13, 2012.
U.S. Appl. No. 12/862,958, 2010-0325758, filed Dec. 23, 2010.
U.S. Appl. No. 12/819,360, 2010-0257623, filed Oct. 7, 2010.
U.S. Appl. No. 12/166,517, 2009-0025108, filed Jan. 22, 2009.
U.S. Appl. No. 13/129,860, 2011-0296548, filed Dec. 1, 2011.
U.S. Appl. No. 12/517,919, 2012-0023601, filed Jan. 26, 2012.
U.S. Appl. No. 12/594,289, 2011-0277051, filed Nov. 10, 2011.
U.S. Appl. No. 12/594,425, 2010-0287641, filed Nov. 11, 2010.
U.S. Appl. No. 11/592,444, 2007-0118920, filed May 24, 2007.
U.S. Appl. No. 12/854,520, 2011-0138503, filed Jun. 9, 2011.
U.S. Appl. No. 11/993,725, 2011-0209232, filed Aug. 25, 2011.
Al-Khatib, K., et al., "Survey of Common Sunflower (*Helianthus annuus*) Resistance to ALS-inhibiting Herbicides in Northeast Kansas". Proceedings of the 21st Sunflower Research Workshop. National Sunflower Association, pp. 210-215; Bismark, ND (Jan. 14-15, 1999).
Al-Khatib, K., et al., "Imazethapyr resistance in common sunflower (*Helianthus annuus*)" Weed Science, 46:403-407 (1998).
Avila, L. A., et al., "Assessment of Acetolactate Synthase (ALS) tolerance to Imazethapyr in Red Rice Ecotypes (*Oryza* spp) and Imidazolinone Tolerant/Resistant Rice (*Oryza sativa*) Varieties". Pest Management Science, vol. 61, No. 2, pp. 171-178 (2005).
Ayyadevara, S., et al., "Discrimination of Primer 3'—Nucleotide Mismatch by Taq DNA Polymerase during Polymerase Chain Reaction". Analytical Biochemistry, vol. 284, pp. 11-18 (2000); Academic Press.

(56)                References Cited

OTHER PUBLICATIONS

Barbosa Filho, M.P., et al., "Upland Rice Production in Brazil," Better Crops International, vol. 16, pp. 43-47, Special Supplement, May 2002.

Barrett, M., "Protection of Grass Crops from Sulfonylurea and Imidazolinone Toxicity". Crop Safeners for Herbicides, pp. 195-220 (1990); Academic Press Inc.

Bennett, Full Complement of Clearfield rice varieties: 2009, Delta Farm Press, Feb. 25, 2008 [online]. [Retrieved on Jan. 3, 2010]. Retrieved from the internet: <URL: http://deltafarmpress.com/rice/clearfield-update-0225/> p. 1, paragraph 14, in 1.

Bernasconi, P., et al., "A Naturally Occurring Point Mutation Confers Broad Range Tolerance to Herbicides That Target Acetolactate Synthase". Journal of Biological Chemistry, vol. 270, No. 29, pp. 17381-17385 (1995).

Boutsalis, P., et al., "Molecular Basis of Resistance to Acetolactate Synthase-Inhibiting Herbicides in Sisymbrium Orientale and Bassica Tournefortii". Pesticide Science, vol. 55, pp. 507-516 (1999).

Brown, M., et al., "Hydrolytic Activation versus Oxidative Degradation of Assert Herbicide, an Imidazolinone Aryl-carboxylate, in Susceptible Wild Oat versus Tolerant Corn and Wheat". Pesticide Biochemistry and Physiology, vol. 27, pp. 24-29 (1987); Academic Press Inc.

Buchheim, J., et al., "Maturation of Soybean Somatic Embryos and the Transition to Plantlet Growth". Plant Physiol., vol. 89, pp. 768-775 (1989).

Chamovitz, D., et al., "The Molecular Basis of Resistance to the Herbicide Norflurazon". Plant Molecular Biology, vol. 16, pp. 967-974 (1991).

Chang, et al., "Herbicide-resistant forms of *Arabidopsis thaliana* acetohydroxyacid synthase: characterization of the catalytic properties and sensitivity to inhibitors of four defined mutants". Biochem. J., vol. 333, pp. 765-777 (1998).

Chong, C, et al., "Amino Acid Residues Conferring Herbicide Tolerance in Tobacco Acetolactate Synthase". Biochemical and Biophysical Research Communications, vol. 279, pp. 462-467 (2000); Academic Press Inc.

De Battista, Juan Jose. "Rice Management and Fertilization in Entre Rios Province"; Special Supplement Publication; Better Crops International, vol. 16, pp. 40-42 (May 2002).

Delrio-Lafreniere SA et al., "Simultaneous allele-specific amplification: a strategy using modified primer-template mismatches for SNP detection—application to prothrombin 20210A (factor II) and factor V Leiden (1691A) gene mutations". Molecular Diagnostics, vol. 6, No. 3, pp. 201-209 (2001).

Doberman, A., et al., "Rice Straw Management", Better Crops International, vol. 16, pp. 7-11, Special Supplementa, May 2002.

Duggleby, R. G., et al., "Acetohydroxyacid Synthase". Journal of Biochemistry and Molecular Biology, Korean Society for Biochemistry and Molecular Biology, KR, vol. 33, No. 1, pp. 1-36 (Jan. 2000).

Duggleby, R., "Identification of an Acetolactate Synthase Small Subunit Gene in Two Eukaryotes". Gene, vol. 190, pp. 245-249 (1997).

Fairhurst, et al., "Rice In the Global Food Supply," Better Crops International, vol. 16, pp. 3-6, Special Supplement May 2002.

Finer, J., et al., "Apical Proliferation of Embryogenic Tissue of Soybean [*Glycine max* (L.) Merrill]". Plant Cell Reports, vol. 7, pp. 238-241 (1988).

Finer, J.J., et al., "Development of an Embryogenic Suspension Culture of Soybean (*Glycine maxMerill*)". Plant Cell, Tissue, and Organ Culture, vol. 15, pp. 125-146 (1988). Kluwer Academic Publishers, Dordrecht Netherlands.

Gallie, D. R., et al., "The Regulation of Gene Expression in Transformed Maize Aleurone and Endosperm Protoplasts: Analysis of Promoter Activity, Intron Enhancement, and mRNA Untranslated Regions on Expression". Plant Physiol., vol. 106, ppn 929-939 (1994).

Gang, Pan et al., "Map-based cloning of a novel rice cytochrome P450 gene CYP81A6 that confers resistance to two different classes of herbicides". Plant Molecular Biology, Kluwer Academic Publishers, DO, vol. 61, No. 6, pp. 933-943 (Aug. 2006).

Hattori, J., et al., "An Acetohydroxyacid Synthase Mutant Reveals a Single Site Involved in Multiple Herbicide Resistance". Molecular and General Genetics, vol. 246, pp. 419-425 (1995); Springer Verlag, Berlin, Germany.

Hattori, J., et al., "Multiple resistance to sulfonylureas and imidazolinones conferred by an acetohydroxyacid synthase gene with separate mutation for selective resistance". Molecular Genetics, vol. 232, pp. 167-173 (1992).

Hershey, H., et al., "Cloning and Functional Expression of the Small Subunit of Acetolactate Synthase from Nicotiana plumbaginifolia". Plant Molecular Biology, vol. 40, pp. 795-806 (1999); Kluwer Academic Publishers; Netherlands.

Inui, Hideyuki, et al., "Herbicide resistance in transgenic plants with mammalian P450 monooxygenase genes". Pest Management Science, vol. 61, No. 3, pp. 286-291 (Mar. 2005).

Jacq, B., et al., "Efficient Production of Uniform Plants from Cotyledon Explants of Sugarbeets (*Beta vulgaris* L.)". Plant Breeding, vol. 110, pp. 185-191 (1993).

Ji-Yun, J., et al., "Rice Production and Fertilization in China," Better Crops International, vol. 16, pp. 26-29, Special Supplement, May 2002.

Kadaru, S., et al., "Development and application of allele-specific PCR assays for imazethapyr resistance in rice (*Oryza sativa*)," Euphytica, vol. 160, pp. 431-438, (2008).

Kaneda, Y., et al., Combination of Thidiazuron and Basal Media with Low Salt Concentrations Increases the Frequency of Shoot Organogenesis in Soybeans [*Glycine max* (l.) Merr.]. Plant Cell Reports, vol. 17, pp. 8-12 (1997).

Kolkman, J. M., et al., "Acetohydroxyacid synthase mutations conferring resistance to imidazolinone or sulfonylurea herbicides in sunflower". Theor. Appl. Genet, vol. 109, pp. 1147-1159 (2004).

Koziel, M. G., et al., "Optimizing expression of transgenes with an emphasis on post-transcriptional events". Plant Molecular Biology, vol. 32, pp. 393-405 (1996).

Kulshreshtha, S., et al., "Direct Somatic Embryogenesis and Plant Regeneration from Mature Sugarbeet (*Beta vulgaris* L.) Zygotic Cotyledons". Plant Growth Regulation, vol. 22, pp. 87-92 (1997).

Lai, F. M., et al., "Scale-up of Somatic Embryogenesis in Alfalfa (*Medicago sativa* L.) I Subculture and Indirect Secondary Somatic Embryogenesis". Plant Cell, Tissue and Organ Culture, vol. 37, pp. 151-158 (1994).

Lee, I., et al., "Guidelines for incorporating non-perfectly matched oligonucleotides into target-specific hybridization probes for DNA microarray". Nucleic Acids Research, vol. 32, pp. 681-690 (2004); Oxford University Press.

Lee, Y., et al., "Effect of Mutagenesis at Serine 653 of *Arabidopsis thaliana* Acetohydroxyacid Synthase on the Sensitivity to Imidazolinone and Sulfonylurea Herbicides". FEBS Letters, vol. 452, pp. 341-345 (1999); Federation of European Biochemical Societies.

Lee, Y., et al., "Identification of the Regulatory Subunit of *Arabidopsis thaliana* Acetohydroxyacid Synthase and Reconstitution with its Catalytic Subunit". Biochemistry, vol. 40, pp. 6836-6844 (2001).

Lenzner, S., et al., "Plant Regeneration form Protoplasts of Sugar Beet (*Beta vulgaris*)". Physiologia Plantarum, vol. 94, pp. 342-350 (1995); Denmark.

Li D., et al., "A mutation at the Ala122 position of acetohydroxyacid synthase (AHAS) located on chromosome 6D of wheat: improved resistance to imidazolinone and a faster assay for marker assisted selection". Mol. Breeding, vol. 22, pp. 217-225 (2008).

Li, L., et al., "An improved rice transformation system using the biolistic method". Plant Cell Reports, vol. 12, pp. 250-255 (1993).

Liu, W., et al., "Somatic Embryo Cycling: Evaluation of a Novel Transformation and Assay System for Seed-Specific Gene Expression in Soybean". Plant Cell, Tissue and Organ Culture, vol. 47, pp. 33-42 (1996).

Mazur, et al., "Isolation and Characterization of Plant Genes Coding for Acetolactate Synthase, the Target Enzyme for Two Classes of Herbicides". Plant Physiol., vol. 85, pp. 1110-1117 (1987).

Mcgranahan, G. H., et al., "Improved Efficiency of the Walnut Somatic Embryo Gene Transfer System". Plant Cell Reports, vol. 8, pp. 512-516 (1990).

(56)                References Cited

OTHER PUBLICATIONS

Miki et al., "Transformation of *Brassica napus* canola cultivars with *Arabidopsis thaliana* Acetohydroxyacid Synthase Genes and Analysis of Herbicide Resistance". Theor. Appl. Genet., vol. 80, pp. 449-458 (1990).

Miller, J.F., et al., "Registration of Two Oilseed Sunflower Genetic Stocks, SURES-1 and SURES-2 Resistant to Tribenuron Herbicide," Crop Science Society of America, vol. 44 No. 3, pp. 1037-1038 (May 2004).

Milliman, L. D., et al., "Characterization of two biotypes of imidazolinone-resistant eastern black nightshade (*Solanum ptycanthum*)". Weed Science, vol. 51, pp. 139-144 (2003).

Moghaddam, B., et al., "The Effect of In Planta TIBA and Proline Treatment on Somatic Embryogenesis of Sugar Beet (*Beta vulgaris* L.)". Euphytica, vol. 112, No. 2, pp. 151-156 (Jan. 2000).

Mutert, E., et al., "Developments in Rice Production in Southeast Asia", Better Crops International, vol. 15, pp. 12-17, Special Supplement, May 2002.

Newhouse, K., et al., "Mutations in corn (*Zea mays* L.) Conferring Resistance to Imidazolinone Herbicides". Theor. Appl. Genet., vol. 83, pp. 65-70 (1991); Springer-Verlag.

Newhouse, K., et al., "Tolerance to Imidazolinone Herbicides in Wheat". Plant Physiology, vol. 100, pp. 882-886 (1992).

Nielsen, J. M., et al., "Synergism of Thidiazuron and Benzyladenine in Axillary Shoot Formation Depends on Sequence of Application in Miscanthus X ogiformis 'Giganteus'". Plant Cell, Tissue and Organ Culture, vol. 41, pp. 165-170 (1995).

Odell, et al., "Comparision of Increased Expression of Wild-Type and Herbicide-Resistant Acetolactate Synthase Genes in Transgenic Plants, and Indication of Posttranscriptional Limitation on Enzyme Activity". Plant Physiol., vol. 94, pp. 1647-1654 (1990).

Ott, K., et al., "Rational Molecular Design and Genetic Engineering of Herbicide Resistant Crops by Structure Modeling and Site-directed Mutagenesis of Acetohydroxyacid Synthase". J. Mol. Biol., vol. 263, pp. 359-368 (1996); Academic Press Limited.

Owens, L. D., et al., "Sugarbeet Leaf Disc Culture: An Improved Procedure for Inducing Morphogenesis". Plant Cell, Tissue and Organ Culture, vol. 31, pp. 195-201 (1992).

Pettersson, M., et al., "Molecular haplotype determination using allele-specific PCR and Pyrosequencing technology". Genomics, vol. 82, pp. 390-396 (2003); Reed Elsevier Science.

Pozniak, C. J., et al., "Physiological and Molecular Characterization of Mutation-Derived Imidazolinone Resistance in Spring Wheat". Crop Science, vol. 44, No. 4, pp. 1434-1443 (2004).

Ray et al., "Mutant Acetolactate Synthase Gene is an Efficient in vitro Selectable Marker for the Genetic Transformation of *Brassica juncea* (Oilseed Mustard)". Journal of Plant Physiology, vol. 161, pp. 1079-1083 (2004).

Repellin, et al., "Genetic Enrichment of Cereal Crops via Alien Gene Transfer: New Challenges". Plant Cell, Tissue and Organ Culture, vol. 64, pp. 159-183 (2001).

Roesler, K., et al., "Targeting of the *Arabidopsis homomeric* acetyl-coenzyme A carboxylase to plastids of rapeseeds". Plant Physiology, vol. 113, pp. 75-81 (1997).

Roussey, I., et al., "In Planta 2,3,5 Triiodobenzoic Acid Treatment Promotes High Frequency and Routine On Vitro Regeneration of Sugarbeet (*Beta vulgaris* L.) Plant". Plant Cell Reports, vol. 16, pp. 142-146 (1996).

Rutledge, et al. Molecular and General Genetics, vol. 229, pp. 31-40 (1991).

Sathasivan, K., et al., "Molecular Basis of Imidazolinone Herbicide Resistance in *Arabidopsis thaliana* var. Columbia". Plant Physiology, vol. 97, pp. 1044-1050 (1991).

Sato, S., et al., "Stable Transformation Via Particle Bombardment in Two Different Soybean Regeneration Systems". Plant Cell Reports, vol. 12, pp. 408-413 (1993).

Saxena et al., "Herbicide Resistance in Datura innoxia ". Plant Physiol., vol. 86, pp. 863-867 (1988).

Schmitzer, P. R., et al., "Lack of Cross-Resistance of Imazaquin-Resistant Xanthium strumarium Acetolactate Synthase to Flumetsulam and Chlorimuron". Plant Physiol, vol. 103, pp. 281-283 (1993).

Sella, C., et al., "Subunit Association in Acetohydroxy Acid Synthase Isozyme III". Journal of Bacteriology, vol. 175, No. 17, pp. 5339-5343 (Sep. 1993).

Sha, X.Y., "Field Evaluation of Imidazolinone-Tolerant Clearfield Rice (*Oryza sativa* L.) at Nine Louisiana Locations," CropScience, vol. 47, pp. 1177-1185 (2007).

Shaner, D., et al., "Imidazolinones: Potent Inhibitors of Acetohydroxyacid Synthase". Plant Physiol, vol. 76, pp. 545-546 (1984).

Shivrain, V.K., et al., "Gene flow between Clearfield™ rice and red rice," ScienceDirect, Crop Protection, vol. 26 pp. 349-356, (2007).

Snyder, C.S., et al., "Rice Production in the United States—An Overview," Better Crops International, vol. 16, pp. 30-35, Special Supplement, May 2002.

Stein, N., et al., "A new DNA extraction method for high-throughput marker analysis in a large-genome species such as Triticum aestivum". Plant Breeding, vol. 120, pp. 354-356 (2001).

Swanson, E., et al., "Microspore Mutagenesis and Selection: Canola Plants with Field Tolerance to the Imidazolinones". Theor Appl Genet, vol. 96, pp. 525-530 (1989); Springer-Verlag.

Tan et al., "Herbicidal Inhibitors of Amino Acid Biosynthesis and Herbicide-Tolerant Crops". Amino Acids, vol. 30, pp. 195-204 (2006).

Tan, S., et al., "Imidazolinone-Tolerant Crops: History, Current Status and Future". Pest Management Science, vol. 61, No. 3, pp. 246-257 (2005).

Tenning, Paul, et al., "Somatic Embryo genesis from zygotic embryos of sugar beet Beta vulgaris". Plant Science, vol. 81, pp. 103-109 (1992).

Tiwari, K.N., "Rice Production and Nutrient Management in India," Better Crops International, vol. 16, pp. 18-22, Special Supplement, May 2002.

Tranel, P. J., et al., "Resistance of Weeds to ALS-Inhibiting Herbicides: What Have We Learned?". Weed Science, Weed Science Society of America, Champaign, IL (US), vol. 50, No. 6, pp. 700-712 (Nov. 2002).

Wagner, J., et al., "Identification of ALS-inhibitor-resistant Amaranthus biotypes using polymerase chain reaction amplification of . . . ". Weed Research, vol. 42, pp. 280-286 (2002).

Warner, Thomas G., "Sweet success with tethered enzyme catalysis". Nature Biotechnology, vol. 16, pp. 720-721 (Aug. 1998).

Weinstock, et al., "Properties of Subcloned Subunits of Bacterial Acetohydroxy Acid Synthases". Journal of Bacteriology, vol. 174, No. 17, pp. 5560-5556 (Sep. 1992); American Society for Microbiology.

Werck-Reichhart, D., et al., "Cytochromes P450 for engineering herbicide tolerance". Trends in Plant Science, Elsevier Science, Oxford, GB, vol. 5, No. 3, p. 116-123 (Mar. 2000).

Werle E., et al., "Convenient single-step, one tube purification of PCR products for direct sequencing". Nucleic Acids Research, vol. 22, No. 20, pp. 4354-4355 (1994).

White, A. D., et al., "Common sunflower resistance to acetolactate synthase-inhibiting herbicides". Weed Science, vol. 50, pp. 432-437 (2002).

White, A. D., et al., "Isolation of Acetolactate Synthase Homologs in Common Sunflowers". Weed Science, Weed Science Society of America, Champaign, IL, vol. 51, No. 6, pp. 845-853 (Nov. 6, 2003).

Wiersma, C., et al., "Isolation, Expression and Phylogenetic Inheiritance of an Acetolactate Synthase Gene from *Brassica napus*". Mol. Gen. Genet., vol. 219, pp. 413-420 (1989).

Wright, M., et al., "A Simple Method for the Recovery of Multiple Fertile Plants from Individual Somatic Embryos of Soybean [*Glycine max* (L) Merrill]". In Vitro Cell Dev Bio., vol. 27P, pp. 153-157 (Jul. 1991). Tissue Culture Association.

Wright, T. R., et al., "Cell Selection and Inheritance of Imidazolinone Resistance in Sugarbeet (*Beta vulgaris*)". Theor. Appl. Genet., vol. 96, pp. 612-620 (1998); Springer-Verlag.

(56) References Cited

OTHER PUBLICATIONS

Wu, D., et al., "Allele-specific enzymatic amplification of B-globin genomic DNA for diagnosis of sickle cell anemia". Proceedings of the National Academy of Sciences, vol. 86, pp. 2757-2760 (1989).

Yu Qin et al., "Tolerance to acetolactate synthase and acetyl-coenzyme A carboxylase inhibiting herbicides in Vulpia bromoides is conferred by two co-existing resistance mechanisms". Pesticide Biochemistry and Physiology, vol. 78, No. 1, pp. 21-30 (Jan. 2004).

Zhang, W., et al., "Genetic and agronomic analyses of red rice-Clearfield hybrids and their progeny produced from natural and controlled crosses," Euphytica, vol. 164, pp. 659-668 (2008).

Zhu et al., "Engineering herbicide-resistant maize using chimeric RNA/DNA oligonucleotides". Nature Biotechnology, vol. 18, pp. 555-558 (2000).

Zhu, X. L., "Computational simulations of the interactions between acetyl-coenzyme-A carboxylase and clodinafop: resistance mechanism due to active and nonactive site mutations." J. Chem. Inf. Model., vol. 49, pp. 1936-1843 (Jul. 13, 2009).

European Office Action dated Nov. 16, 2016 from 06 736 630.2.

S.S. Sandhu et al., "RAPD analysis of herbicide-resistant Brasilian rice lines produced via mutagenesis" Genet. Mol. Res. 1 (4): 359-370 (Dec. 30, 2002).

C. Duncan, "Factors Affecting Herbicide Performance," TechLine Invasive Plant News , Jun. 5, 2018, 5 pgs. (http://techlinenews.com/herbicides/herbicidepeformance2014).

B.H. Wells, "Effects of Lactofen Herbicide on Cellular Uptake of Glyphosate Herbicide in *Malva parviflora* L..," Crop Science Ph.D. Thesis, Oregon State University, Jan. 31, 1989, 127 pgs.

J.L.P. van Oorschot, "Types of Selective Action by Herbicides which Inhibit Photosynthesis," Z. Naturforsch, 34c(11), 1979, pp. 900-904.

R. Ma, et al., "Measuring Rates of Herbicide Metabolism in Dicot Weeds with an Excised Leaf Assay," J Vis Exp., 103:53236, 2015, ePub Sep. 7, 2015; doi: 10.3791/53236.

J.R. Qasem, "Herbicides Applications: Problems and Considerations," Ch. 32 in A. Kortekamp (ed.), Herbicides and Environment, pp. 643-664, Jan. 2011, ePub Jan. 8, 2011: ISBN: 978-953-307-476-4. (available from InTechOpen at: http://www.intechopen.com/books/herbicides-and-environment/herbicides-applications-problems-and-condiiserations).

Sega, G.A., "A review of the genetic effects of ethyl methanesulfonate," Abstract.

Ducar et al, Weed Technology (2004) 18: 1018-1022.

Sibony et al (2001) 41 :509-522.

Singh (1999) "Biosynthesis of valine, leucine and isoleucine," in Plant Amino Acid.

Subramanian et al. (1990) Plant Physiol. 94: 239-244.

The Arable Farming publication, New SU for Grass Weed Control in Cereals, Arable Framing, Dec. 8, 2001.

Webster et al, Weed Science (2001) 49:652-657.

Jander et al., Ethylmethane Sulfonate Saturation Mutagenesis in *Arabidopsis* to Determine Frequency of Herbicide Resistance, Plant Physiol. 131(1):139-146 (Jan. 2003) (ePublished Jan. 1, 2003; doi: 10.1104/pp.102.010397).

Elizabeth A. Greene, et al., Spectrum of Chemically Induced Mutations From a Large-Scale Reverse-Genetic Screen in *Arabidopsis*, Fred Hutchinson Cancer Research Center and Howard Hughes Medical Institute, Seattle, Washington 98109 and Department of Biology, University of Washington, Seattle, Washington 98195, Copyright 2003 by the Genetics Society of America, pp. 731-740.

Peng et al,Transgenic rice resistant to imidazolinone herbicides, in Khush et al., Ed. 2003. Advances in rice genetics. Supplement to Rice genetics IV. Proceedings of the Fourth International Rice Genetics Symposium, Oct. 22-27, 2000, Los Banos, Philippines; p. 590-593.

Invasive.org Handbook, Imazapic, 7g.1-7g.7, available at: https://www.invasive.org/gist/ products/handbook/16.imazapic.pdf, last accessed Sep. 12, 2023.

Invasive.org Handbook, Imazapyr, 7h.1-7h.7, available at: https://www.invasive.org/gist/ products/handbook/17.imazapyr.pdf, last accessed Sep. 12, 2023.

* cited by examiner

FIGURE 1

```
            601                                                    650
SEQ ID NO:1 .......... .......... .......... .......... ..........
OsAHASL1.1  .......... .......... .......... .......... ..........
OsAHASL1.2  .......... .......... .......... .......... ..........
OsAHASL1.4  .......... ....CCCAAA CCCAGAAACC CTCGCCGCCG CCGCCGCCGC
OsAHASL1.6  .......... .......... .......... CTCGCCGCCG CCGCCGCCGC
   ZmAHASL1 CCCACTCCGT GCCAGGTGCC ACCCTCCCCA AGCCCTCGCG CCGCCTCCGA
   ZmAHASL2 CCCACTCCGT GTC.CGTGGC ACCCACCCCA AACCCTCGCG CCGCCTCCGA
   OsAHASL2 .......... .......... .......... ATGGCTGCCG CCGCCGCCGC
    AtAHASL ATGGCGGCGG CAACAACAAC AACAACAACA TCTTCTTCGA TCTCCTTCTC 651                                                    700
SEQ ID NO:1 .....CCCAC CATGGCTACG ACCGCCGCGG CC..GCGGCC GCCACCTTGT
OsAHASL1.1  .....CCCAC CATGGCTACG ACCGCCGCGG CC..GCGGCC GCCACCTTGT
OsAHASL1.2  .......... .ATGGCTACG ACCGCCGCGG CC..GCGGCC GCCACCTTGT
OsAHASL1.4  CACCACCCAC CATGGCTACG ACCGCCGCGG CC..GCGGCC GCCGCCCTGT
OsAHASL1.6  CACCACCCAC CATGGCTACG ACCGCCGCGG CC..GCGGCC GCCGCCCTGT
   ZmAHASL1 GACAGCCGCC CGCAACCATG GCCACCGCCG CC..ACCGCC GCCGCCGCGC
   ZmAHASL2 GACAGCCG.C CGCAACCATG GCCACCGCCG CC..GCCGCG TCTACCGCGC
   OsAHASL2 CGCCTCACTC TCCGTCTCCG AC.GCCGCCG CTAAGCTGCC CAAACCGGGA
    AtAHASL CACCAAAC.C ATCTCCTTCC TCCTCCAAAT CACCATTACC AATCTCCAGA 701                                                    750
SEQ ID NO:1 CCGCCGCCGC GACGGCCAAG ACCGGCCGTA AGAACCACCA GCGACACCAC
OsAHASL1.1  CCGCCGCCGC GACGGCCAAG ACCGGCCGTA AGAACCACCA GCGACACCAC
OsAHASL1.2  CCGCCGCCGC GACGGCCAAG ACCGGCCGTA AGAACCACCA GCGACACCAC
OsAHASL1.4  CCGCCGCCGC GACGGCCAAG ACCGGCCGTA AGAACCACCA GCGACACCAC
OsAHASL1.6  CCGCCGCCGC GACGGCCAAG ACCGGCCGTA AGAACCACCA GCGACACCAC
   ZmAHASL1 TCACCGGCGC CACTACCGCT ACGCCCAAGT CGAGGCGCCG AGCCCACCAC
   ZmAHASL2 TCACTGGCGC CACTACCGCT GCGCCCAAGG CGAGGCGCCG GGCGCACCTC
   OsAHASL2 GGGCAAGTGC AACGGCGACG CGACAGGGAT CGTCCACGCG TGGATGCTGC
    AtAHASL TTCTCCCTCC CATTCTCCCT AAACCCCAAC AAATCATCCT CCTCCTCCCG 751                                                    800
SEQ ID NO:1 GTCTT.TCCC GCTCGAGGCC GG.GTGGGGG CGGCGGCGGT CAGGTGCTCG
OsAHASL1.1  GTCTT.TCCC GCTCGAGGCC GG.GTGGGGG CGGCGGCGGT CAGGTGCTCG
OsAHASL1.2  GTCTT.TCCC GCTCGAGGCC GG.GTGGGGG CGGCGGCGGT CAGGTGCTCG
OsAHASL1.4  GTCCT.TCCC GCTCGAGGCC GG.GTGGGGG CGGCGGCGGT CAGGTGCTCG
OsAHASL1.6  GTCCT.TCCC GCTCGAGGCC GG.GTGGGGG CGGCGGCGGT CAGGTGCTCG
   ZmAHASL1 TTGGC....C ACCCGGCGCG CC.CTC...G CCGCGCCCAT CAGGTGCTCA
   ZmAHASL2 CTGGC....C ACCCGCCGCG CC.CTC...G CCGCGCCCAT CAGGTGCTCA
   OsAHASL2 CGCCT...GC ACCCGCGACA GC.CGCCGTC CCACGCGCGA GAGGTGCTCG
    AtAHASL CCGCCGCGGT ATCAAATCCA GCTCTCCCTC CTCCATCTCC GCCGTGCTCA
```

FIGURE 1 (continued)

```
             851                                                    900
SEQ ID NO:1  .......... .GCTCCGGCC GTGGGGGCCG GCCGAGCCCC GCAAGGGCGC
OsAHASL1.1   .......... .GCTCCGGCC GTGGGGGCCG GCCGAGCCCC GCAAGGGCGC
OsAHASL1.2   .......... .GCTCCGGCC GTGGGGGCCG GCCGAGCCCC GCAAGGGCGC
OsAHASL1.4   .......... .GCTCCGGCC GTGGGGGCCG GCCGAGCCCC GCAAGGGCGC
OsAHASL1.6   .......... .GCTCCGGCC GTGGGGGCCG GCCGAGCCCC GCAAGGGCGC
   ZmAHASL1  .......... .GCTACGTCC GTGGGGCCCC AACGAGCCCC GCAAGGGCTC
   ZmAHASL2  .......... .GCTCCGGCC GTGGGGCCCC ACCGATCCCC GCAAGGGCGC
   OsAHASL2  GTGCGCGCGC CGGTCCGGAC GCGGGCGCCC ATGGGGCAGC GGAAGGGCGC
    AtAHASL  CCCGAAACAT TCATCTCCCG ATTCGCTCCA GATCAACCCC GCAAAGGCGC 901                                                    950
SEQ ID NO:1  GGACATCCTC GTGGAGGCGC TGGAGCGGTG CGGCGTCAGC GACGTGTTCG
OsAHASL1.1   GGACATCCTC GTGGAGGCGC TGGAGCGGTG CGGCGTCAGC GACGTGTTCG
OsAHASL1.2   GGACATCCTC GTGGAGGCGC TGGAGCGGTG CGGCGTCAGC GACGTGTTCG
OsAHASL1.4   GGACATCCTC GTGGAGGCGC TGGAGCGGTG CGGCGTCAGC GACGTGTTCG
OsAHASL1.6   GGACATCCTC GTGGAGGCGC TGGAGCGGTG CGGCGTCAGC GACGTGTTCG
   ZmAHASL1  CGACATCCTC GTCGAGGCTC TCGAGCGCTG TGGCGTCCGT GACGTCTTCG
   ZmAHASL2  CGACATCCTC GTCGAGTCCC TCGAGCGCTG CGGCGTCCGC GACGTCTTCG
   OsAHASL2  GGACATCGTC GTCGAGGCGC TGGAGCGGTG CGGCGTCCGC GACGTGTTCG
    AtAHASL  TGATATCCTC GTCGAAGCTT TAGAACGTCA AGGCGTAGAA ACCGTATTCG 951                                                   1000
SEQ ID NO:1  CCTACCCGGG CGGCGCGTCC ATGGAGATCC ACCAGGCGCT GACGCGCTCC
OsAHASL1.1   CCTACCCGGG CGGCGCGTCC ATGGAGATCC ACCAGGCGCT GACGCGCTCC
OsAHASL1.2   CCTACCCGGG CGGCGCGTCC ATGGAGATCC ACCAGGCGCT GACGCGCTCC
OsAHASL1.4   CCTACCCGGG CGGCGCGTCC ATGGAGATCC ACCAGGCGCT GACGCGCTCC
OsAHASL1.6   CCTACCCGGG CGGCGCGTCC ATGGAGATCC ACCAGGCGCT GACGCGCTCC
   ZmAHASL1  CCTACCCCGG CGGCGCATCC ATGGAGATCC ACCAGGCACT CACCCGCTCC
   ZmAHASL2  CCTACCCCGG CGGCGCGTCC ATGGAGATCC ACCAGGCACT CACCCGCTCC
   OsAHASL2  AGTACCCGGG CGGCGCGTCA ATGGAGATCC ACCAGGCGCT GACGCGGTCG
    AtAHASL  CTTACCCTGG AGGTGCATCA ATGGAGATTC ACCAAGCCTT AACCCGCTCT 1001                                                  1050
SEQ ID NO:1  CCGGTCATCA CCAACCACCT CTTCCGCCAC GAGCAGGGCG AGGCGTTCGC
OsAHASL1.1   CCGGTCATCA CCAACCACCT CTTCCGCCAC GAGCAGGGCG AGGCGTTCGC
OsAHASL1.2   CCGGTCATCA CCAACCACCT CTTCCGCCAC GAGCAGGGCG AGGCGTTCGC
OsAHASL1.4   CCGGTCATCA CCAACCACCT CTTCCGCCAC GAGCAGGGCG AGGCGTTCGC
OsAHASL1.6   CCGGTCATCA CCAACCACCT CTTCCGCCAC GAGCAGGGCG AGGCGTTCGC
   ZmAHASL1  CCCGTCATCG CCAACCACCT CTTCCGCCAC GAACAAGGGG AGGCCTTCGC
   ZmAHASL2  CCCGTCATCG CCAACCACCT CTTCCGCCAC GAGCAAGGGG AGGCCTTTGC
   OsAHASL2  CCGGTGATCC GCAACCACCT GCTCCGCCAC GAGCAGGGGG AGGCCTTCGC
    AtAHASL  TCCTCAATCC GTAACGTCCT TCCTCGTCAC GAACAAGGAG GTGTATTCGC
```

FIGURE 1 (continued)

```
            1051                                              1100
SEQ ID NO:1 GGCGTCCGGG TACGCGCGCG CGTCCGGCCG CGTCGGGGTC TGCGTCGCCA
OsAHASL1.1  GGCGTCCGGG TACGCGCGCG CGTCCGGCCG CGTCGGGGTC TGCGTCGCCA
OsAHASL1.2  GGCGTCCGGG TACGCGCGCG CGTCCGGCCG CGTCGGGGTC TGCGTCGCCA
OsAHASL1.4  GGCGTCCGGG TACGCGCGCG CGTCCGGCCG CGTCGGGGTC TGCGTCGCCA
OsAHASL1.6  GGCGTCCGGG TACGCGCGCG CGTCCGGCCG CGTCGGGGTC TGCGTCGCCA
   ZmAHASL1 CGCCTCCGCG TACGCGCGCT CCTCGGGCCG CGTTGGCGTC TGCATCGCCA
   ZmAHASL2 GGCCTCCGGC TACGCGCGCT CCTCGGGCCG CGTCGGCGTC TGCATCGCCA
   OsAHASL2 GGCGTCCGGG TACGCGCGCT CGTCGGGGCG GCCGGGCGTC TGCGTCGCCA
    AtAHASL AGCAGAAGGA TACGCTCGAT CCTCAGGTAA ACCAGGTATC TGTATAGCCA 1101                                              1150
SEQ ID NO:1 CCTCCGGCCC CGGGGCAACC AACCTCGTGT CCGCGCTCGC CGACGCGCTG
OsAHASL1.1  CCTCCGGCCC CGGGGCAACC AACCTCGTGT CCGCGCTCGC CGACGCGCTG
OsAHASL1.2  CCTCCGGCCC CGGGGCAACC AACCTCGTGT CCGCGCTCGC CGACGCGCTG
OsAHASL1.4  CCTCCGGCCC CGGGGCAACC AACCTCGTGT CCGCGCTCGC CGACGCGCTG
OsAHASL1.6  CCTCCGGCCC CGGGGCAACC AACCTCGTGT CCGCGCTCGC CGACGCGCTG
   ZmAHASL1 CCTCCGGCCC CGGCGCCACC AACCTAGTCT CTGCGCTCGC AGACGCGTTG
   ZmAHASL2 CCTCCGGCCC CGGCGCCACC AACCTTGTCT CCGCGCTCGC CGACGCGCTG
   OsAHASL2 CCTCCGGCCC GGGCGCCACC AACCTCGTGT CCGCGCTCGC CGACGCCCAC
    AtAHASL CTTCAGGTCC CGGAGCTACA AATCTCGTTA GCGGATTAGC CGATGCGTTG 1151                                              1200
SEQ ID NO:1 CTCGACTCCG TCCCGATGGT CGCCATCACG GGCCAGGTCC CCCGCCGCAT
OsAHASL1.1  CTCGACTCCG TCCCGATGGT CGCCATCACG GGCCAGGTCC CCCGCCGCAT
OsAHASL1.2  CTCGACTCCG TCCCGATGGT CGCCATCACG GGCCAGGTCC CCCGCCGCAT
OsAHASL1.4  CTCGACTCCG TCCCGATGGT CGCCATCACG GGCCAGGTCC CCCGCCGCAT
OsAHASL1.6  CTCGACTCCG TCCCGATGGT CGCCATCACG GGCCAGGTCC CCCGCCGCAT
   ZmAHASL1 CTCGACTCCG TCCCCATGGT CGCCATCACG GGACAGGTGC CGCGACGCAT
   ZmAHASL2 CTCGATTCCG TCCCCATGGT CGCCATCACG GGACAGGTGC CGCGACGCAT
   OsAHASL2 CTCGACTCCG TCCCGCTCGT CGCCATCACG GGGCAGGCCC CGCGCCGCAT
    AtAHASL TTAGATAGTG TTCCTCTTGT AGCAATCACA GGACAAGTCC CTCGTCGTAT 1201                                              1250
SEQ ID NO:1 GATCGGCACC GACGTCTTCC AGGAGACGCC CATAGTCGAG GTCACCCGCT
OsAHASL1.1  GATCGGCACC GACGCCTTCC AGGAGACGCC CATAGTCGAG GTCACCCGCT
OsAHASL1.2  GATCGGCACC GACGCCTTCC AGGAGACGCC CATAGTCGAG GTCACCCGCT
OsAHASL1.4  GATCGGCACC GACGCCTTCC AGGAGACGCC CATAGTCGAG GTCACCCGCT
OsAHASL1.6  GATCGGCACC GACGCCTTCC AGGAGACGCC CATAGTCGAG GTCACCCGCT
   ZmAHASL1 GATTGGCACC GACGCCTTTC AGGAGACGCC CATCGTCGAG GTCACCCGCT
   ZmAHASL2 GATTGGCACC GACGCCTTCC AGGAGACGCC CATCGTCGAG GTCACCCGCT
   OsAHASL2 GATCGGCACC GACGCGTTCC AGGAGACGCC CATCGTCGAG TTCACCCGCT
    AtAHASL GATTGGTACA GATGCGTTTC AAGAGACTCC GATTGTTGAG GTAACGCGTT
```

FIGURE 1 (continued)

```
            1251                                                       1300
SEQ ID NO:1 CCATCACCAA GCACAATTAC CTTGTCCTTG ATGTGGAGGA CATCCCCCGC
OsAHASL1.1  CCATCACCAA GCACAATTAC CTTGTCCTTG ATGTGGAGGA CATCCCCCGC
OsAHASL1.2  CCATCACCAA GCACAATTAC CTTGTCCTTG ATGTGGAGGA CATCCCCCGC
OsAHASL1.4  CCATCACCAA GCACAATTAC CTTGTCCTTG ATGTGGAGGA CATCCCCCGC
OsAHASL1.6  CCATCACCAA GCACAATTAC CTTGTCCTTG ATGTGGAGGA CATCCCCCGC
   ZmAHASL1 CCATCACCAA GCACAACTAC CTGGTCCTCG ACGTCGACGA CATCCCCCGC
   ZmAHASL2 CCATCACCAA GCACAACTAC CTGGTCCTCG ACGTCGACGA CATCCCCCGC
   OsAHASL2 CCATCACCAA GCACAACTAC CTAATCCTCG ACGTCGACGA CATCCCCCGC
     AtAHASL CGATTACGAA GCATAACTAT CTTGTGATGG ATGTTGAAGA TATCCCTAGG 1301                                                       1350
SEQ ID NO:1 GTCATACAGG AAGCCTTCTT CCTCGCGTCC TCGGGCCGTC CTGGCCCGGT
OsAHASL1.1  GTCATACAGG AAGCCTTCTT CCTCGCGTCC TCGGGCCGTC CTGGCCCGGT
OsAHASL1.2  GTCATACAGG AAGCCTTCTT CCTCGCGTCC TCGGGCCGTC CTGGCCCGGT
OsAHASL1.4  GTCATACAGG AAGCCTTCTT CCTCGCGTCC TCGGGCCGTC CTGGCCCGGT
OsAHASL1.6  GTCATACAGG AAGCCTTCTT CCTCGCGTCC TCGGGCCGTC CTGGCCCGGT
   ZmAHASL1 GTCGTGCAGG AGGCCTTCTT CCTCGCATCC TCTGGTCGCC CGGGGCCGGT
   ZmAHASL2 GTCGTGCAGG AGGCTTTCTT CCTCGCCTCC TCTGGTCGAC CGGGGCCGGT
   OsAHASL2 GTCATCAACG AGGCCTTCTT CCTCGCGTCC ACGGGTCGCC CCGGCCCGGT
     AtAHASL ATTATTGAGG AAGCTTTCTT TTTAGCTACT TCTGGTAGAC CTGGACCTGT 1351                                                       1400
SEQ ID NO:1 GCTGGTCGAC ATCCCCAAGG ACATCCAGCA GCAGATGGCT GTGCCAGTCT
OsAHASL1.1  GCTGGTCGAC ATCCCCAAGG ACATCCAGCA GCAGATGGCT GTGCCAGTCT
OsAHASL1.2  GCTGGTCGAC ATCCCCAAGG ACATCCAGCA GCAGATGGCT GTGCCAGTCT
OsAHASL1.4  GCTGGTCGAC ATCCCCAAGG ACATCCAGCA GCAGATGGCC GTGCCGGTCT
OsAHASL1.6  GCTGGTCGAC ATCCCCAAGG ACATCCAGCA GCAGATGGCC GTGCCGGTCT
   ZmAHASL1 GCTTGTTGAC ATCCCCAAGG ACATCCAGCA GCAGATGGCG GTGCCGGCCT
   ZmAHASL2 GCTTGTCGAC ATCCCCAAGG ACATCCAGCA GCAGATGGCG GTGCCTGTCT
   OsAHASL2 GCTCGTCGAC ATCCCCAAGG ACATCCAGCA GCAGATGGCC GTGCCGTCCT
     AtAHASL TTTGGTTGAT GTTCCTAAAG ATATTCAACA ACAGCTTGCG ATTCCTAATT 1401                                                       1450
SEQ ID NO:1 GGGACACCTC GATGAATCTA CCGGGGTACA TTGCACGCCT GCCCAAGCCA
OsAHASL1.1  GGGACACCTC GATGAATCTA CCGGGGTACA TTGCACGCCT GCCCAAGCCA
OsAHASL1.2  GGGACACCTC GATGAATCTA CCGGGGTACA TTGCACGCCT GCCCAAGCCA
OsAHASL1.4  GGGACACCTC GATGAATCTA CCAGGGTACA TCGCACGCCT GCCCAAGCCA
OsAHASL1.6  GGGACACCTC GATGAATCTA CCAGGGTACA TCGCACGCCT GCCCAAGCCA
   ZmAHASL1 GGGACACGCC CATGAGTCTG CCTGGGTACA TCGCGCGCCT TCCCAAGCCT
   ZmAHASL2 GGGACAAGCC CATGAGTCTG CCTGGGTACA TTGCGCGCCT TCCCAAGCCC
   OsAHASL2 GGGACGCGCC GATGCGCCTC CCGGGGTACA TCTCCCGGCT GCCGAAGCCG
     AtAHASL GGGAACAGGC TATGAGATTA CCTGGTTATA TGTCTAGGAT GCCTAAACCT
```

FIGURE 1 (continued)

```
            1451                                                    1500
SEQ ID NO:1 CCCGCGACAG AATTGCTTGA GCAGGTCTTG CGTCTGGTTG GCGAGTCACG
OsAHASL1.1  CCCGCGACAG AATTGCTTGA GCAGGTCTTG CGTCTGGTTG GCGAGTCACG
OsAHASL1.2  CCCGCGACAG AATTGCTTGA GCAGGTCTTG CGTCTGGTTG GCGAGTCACG
OsAHASL1.4  CCCGCGACAG AATTGCTTGA GCAGGTCTTG CGTCTGGTTG GCGAGTCACG
OsAHASL1.6  CCCGCGACAG AATTGCTTGA GCAGGTCTTG CGTCTGGTTG GCGAGTCACG
   ZmAHASL1 CCCGCGACTG AATTTCTTGA GCAGGTGCTG CGTCTTGTTG GTGAATCACG
   ZmAHASL2 CCTGCGACTG AGTTGCTTGA GCAGGTGCTG CGTCTTGTTG GTGAATCCCG
   OsAHASL2 CCGGCCGCCA ACCTGCTCGA CGAAGTCATC CGCCTCGTCG GCGACGCCGA
    AtAHASL CCGGAAGATT CTCATTTGGA GCAGATTGTT AGGTTGATTT CTGAGTCTAA 1501                                                    1550
SEQ ID NO:1 GCGCCCGATT CTCTATGTCG GTGGTGGCTG CTCTGCATCT GGTGATGAAT
OsAHASL1.1  GCGCCCGATT CTCTATGTCG GTGGTGGCTG CTCTGCATCT GGTGATGAAT
OsAHASL1.2  GCGCCCGATT CTCTATGTCG GTGGTGGCTG CTCTGCATCT GGTGATGAAT
OsAHASL1.4  GCGCCCGATT CTCTATGTCG GTGGTGGCTG CTCTGCATCT GGTGACGAAT
OsAHASL1.6  GCGCCCGATT CTCTATGTCG GTGGTGGCTG CTCTGCATCT GGTGACGAAT
   ZmAHASL1 GCGCCCTGTT CTTTATGTTG GCGGTGGCTG TGCAGCATCA GGTGAGGAGT
   ZmAHASL2 GCGCCCTGTT CTTTATGTTG GCGGTGGCTG CGCAGCATCT GGTGAGGAGT
   OsAHASL2 GAGGCCCGTC CTCTACGTCG GCGGCGGGTG CTCCGCGTCG GGCTACGAGC
    AtAHASL GAAGCCTGTG TTGTATGTTG GTGGTGGTTG TTTGAATTCT AGCGATGAAT 1551                                                    1600
SEQ ID NO:1 TGCGCCGGTT TGTTGAGCTG ACCGGCATCC CAGTTACAAC CACTCTGATG
OsAHASL1.1  TGCGCCGGTT TGTTGAGCTG ACCGGCATCC CAGTTACAAC CACTCTGATG
OsAHASL1.2  TGCGCCGGTT TGTTGAGCTG ACCGGCATCC CAGTTACAAC CACTCTGATG
OsAHASL1.4  TGCGCTGGTT TGTTGAGCTG ACTGGTATCC CAGTTACAAC CACTCTGATG
OsAHASL1.6  TGCGCTGGTT TGTTGAGCTG ACTGGTATCC CAGTTACAAC CACTCTGATG
   ZmAHASL1 TGTGCCGCTT TGTGGAGTTG ACTGGAATCC CAGTCACAAC TACTCTTATG
   ZmAHASL2 TGCGACGCTT TGTGGAGCTG ACTGGAATCC CGGTCACAAC TACTCTTATG
   OsAHASL2 TGCGGCGCTT CGTGGAGCTG ACGGGCATCC CGGTGACGAC CACCCTCATG
    AtAHASL TGGGTAGGTT TGTTGAGCTT ACGGGGATCC CTGTTGCGAG TACGTTGATG 1601                                                    1650
SEQ ID NO:1 GGCCTCGGCA ATTTCCCCAG TGATGATCCG TTGTCCCTGC GCATGCTTGG
OsAHASL1.1  GGCCTCGGCA ATTTCCCCAG TGATGATCCG TTGTCCCTGC GCATGCTTGG
OsAHASL1.2  GGCCTCGGCA ATTTCCCCAG TGATGATCCG TTGTCCCTGC GCATGCTTGG
OsAHASL1.4  GGCCTCGGCA ATTTCCCCAG TGACGACCCG TTGTCCCTGC GCATGCTTGG
OsAHASL1.6  GGCCTCGGCA ATTTCCCCAG TGACGACCCG TTGTCCCTGC GCATGCTTGG
   ZmAHASL1 GGCCTTGGCA ACTTCCCCAG CGACGACCCA CTGTCACTGC GCATGCTTGG
   ZmAHASL2 GGCCTCGGCA ACTTCCCCAG CGACGACCCA CTGTCTCTGC GCATGCTAGG
   OsAHASL2 GGCATCGGGA ACTTCCCCAG CGACGACCCG CTCTCGCTGC GGATGCTCGG
    AtAHASL GGGCTGGGAT CTTATCCTTG TGATGATGAG TTGTCGTTAC ATATGCTTGG
```

FIGURE 1 (continued)

```
            1651                                                    1700
SEQ ID NO:1 GATGCATGGC ACGGTGTACG CAAATTATGC GGTGGATAAG GCTGACCTGT
OsAHASL1.1  GATGCATGGC ACGGTGTACG CAAATTATGC GGTGGATAAG GCTGACCTGT
OsAHASL1.2  GATGCATGGC ACGGTGTACG CAAATTATGC GGTGGATAAG GCTGACCTGT
OsAHASL1.4  GATGCATGGC ACGGTGTACG CAAATTATGC CGTGGATAAG GCTGACCTGT
OsAHASL1.6  GATGCATGGC ACGGTGTACG CAAATTATGC CGTGGATAAG GCTGACCTGT
   ZmAHASL1 TATGCATGGC ACAGTGTATG CAAATTATGC AGTGGATAAG GCCGATCTGT
   ZmAHASL2 TATGCATGGC ACGGTGTATG CAAATTATGC AGTGGATAAG GCCGATCTGT
   OsAHASL2 GATGCATGGC ACTGTGTACG CCAACTACGC CGTCGACAAC GCCGACCTCC
    AtAHASL AATGCATGGG ACGGTGTATG CGAATTACGC TGTGGAGCAT AGTGATTTGT 1701                                                    1750
SEQ ID NO:1 TGCTTGCATT TGGCGTGCGG TTTGATGATC GTGTGACAGG GAAAATTGAG
OsAHASL1.1  TGCTTGCATT TGGCGTGCGG TTTGATGATC GTGTGACAGG GAAAATTGAG
OsAHASL1.2  TGCTTGCATT TGGCGTGCGG TTTGATGATC GTGTGACAGG GAAAATTGAG
OsAHASL1.4  TGCTTGCGTT TGGTGTGCGG TTTGATGATC GTGTGACAGG GAAAATTGAG
OsAHASL1.6  TGCTTGCGTT TGGTGTGCGG TTTGATGATC GTGTGACAGG GAAAATTGAG
   ZmAHASL1 TGCTTGCATT TGGTGTGCGG TTTGATGATC GTGTGACAGG GAAAATTGAG
   ZmAHASL2 TGCTTGCACT TGGTGTGCGG TTTGATGATC GTGTGACAGG GAAGATTGAG
   OsAHASL2 TCCTCGCGCT CGGCGTGCGC TTCGACGACC GCGTCACCGG CAAAGTCGAG
    AtAHASL TGTTGGCGTT TGGGGTGAGG TTTGATGATC GCGTCACGGG TAAGCTTGAG 1751                                                    1800
SEQ ID NO:1 GCTTTTGCAA GCAGGGCCAA GATTGTGCAC ATTGACATTG ATCCAGCGGA
OsAHASL1.1  GCTTTTGCAA GCAGGGCCAA GATTGTGCAC ATTGACATTG ATCCAGCGGA
OsAHASL1.2  GCTTTTGCAA GCAGGGCCAA GATTGTGCAC ATTGACATTG ATCCAGCGGA
OsAHASL1.4  GCTTTTGCAA GCAGGGCCAA GATTGTGCAC ATTGACATTG ATCCAGCAGA
OsAHASL1.6  GCTTTTGCAA GCAGGGCCAA GATTGTGCAC ATTGACATTG ATCCAGCAGA
   ZmAHASL1 GCTTTTGCAG GCAGAGCTAA GATTGTGCAC ATTGATATTG ATCCTGCTGA
   ZmAHASL2 GCTTTTGCAA GCAGGGCTAA GATTGTGCAC GTTGATATTG ATCCGGCTGA
   OsAHASL2 GCGTTCGCGA GCAGGGCCAA GATCGTGCAC GTCGACATCG ACCCGTCGGA
    AtAHASL GCTTTTGCTA GTAGGGCTAA GATTGTTCAT ATTGATATTG ACTCTGCTGA 1801                                                    1850
SEQ ID NO:1 GATTGGAAAG AACAAGCAAC CACATGTGTC AATTTGCGCA GATGTTAAGC
OsAHASL1.1  GATTGGAAAG AACAAGCAAC CACATGTGTC AATTTGCGCA GATGTTAAGC
OsAHASL1.2  GATTGGAAAG AACAAGCAAC CACATGTGTC AATTTGCGCA GATGTTAAGC
OsAHASL1.4  GATTGGAAAG AACAAGCAAC CACATGTGTC AATTTGCGCA GATGTTAAGC
OsAHASL1.6  GATTGGAAAG AACAAGCAAC CACATGTGTC AATTTGCGCA GATGTTAAGC
   ZmAHASL1 GATTGGCAAG AACAAGCAGC CACATGTGTC CATCTGTGCA GATGTTAAGC
   ZmAHASL2 GATTGGCAAG AACAAGCAGC CACATGTGTC CATCTGTGCA GATGTTAAGC
   OsAHASL2 GCTCGGGAAG AACAAGCAGC CGCACGTCTC CATCTGCGCC GACGTCAAGC
    AtAHASL GATTGGGAAG AATAAGACTC CTCATGTGTC TGTGTGTGGT GATGTCAAGC
```

FIGURE 1 (continued)

```
            1851                                                    1900
SEQ ID NO:1 TTGCTTTACA GGGCTTGAAT GCTCTGCTAG ACCA...GAG CACAACAAAG
OsAHASL1.1  TTGCTTTACA GGGCTTGAAT GCTCTGCTAG ACCA...GAG CACAACAAAG
OsAHASL1.2  TTGCTTTACA GGGCTTGAAT GCTCTGCTAG ACCA...GAG CACAACAAAG
OsAHASL1.4  TTGCTTTACA GGGCTTGAAT GCTCTGCTAC AACA...GAG CACAACAAAG
OsAHASL1.6  TTGCTTTACA GGGCTTGAAT GCTCTGCTAC AACA...GAG CACAACAAAG
   ZmAHASL1 TTGCTTTGCA GGGCATGAAT ACTCTTCTGG AAGG...AAG CACATCAAAG
   ZmAHASL2 TTGCTTTGCA GGGCATGAAT GCTCTTCTTG AAGG...AAG CACATCAAAG
   OsAHASL2 TCGCCCTGCA GGGCATGAAC GCGATGCTGG AAGAACAGAG CGCCGCCGCC
    AtAHASL TGGCTTTGCA AGGGATGAAT AAGGTTCTTG AGAA.CCGAG CTGAGGAGC.

1901                                                    1950
SEQ ID NO:1 ACAAGTT... ..CTG.ATTT TAGTGCGTGG CACAATGAGT TGGACCAGCA
OsAHASL1.1  ACAAGTT... ..CTG.ATTT TAGTGCGTGG CACAATGAGT TGGACCAGCA
OsAHASL1.2  ACAAGTT... ..CTG.ATTT TAGTGCGTGG CACAATGAGT TGGACCAGCA
OsAHASL1.4  ACAAGTT... ..CTG.ATTT TAGTGCATGG CACAATGAGT TGGACCAGCA
OsAHASL1.6  ACAAGTT... ..CTG.ATTT TAGTGCATGG CACAATGAGT TGGACCAGCA
   ZmAHASL1 AAGAGCT... ..TTG.ACTT CGGCTCATGG CATGATGAAT TGGATCAGCA
   ZmAHASL2 AAGAGCT... ..TTG.ACTT TGGCTCATGG AACGATGAGT TGGATCAGCA
   OsAHASL2 GCGCGCAAGA ACCTCGATTT CAGCGCGTGG CGCTCGGAGC TGGAGAAGAA
    AtAHASL TTAAGCT... ...TG.ATTT TGGAGTTTGG AGGAATGAGT TGAACGTACA 1951                                                    2000
SEQ ID NO:1 GAAGAGGGAG TTTCCTCTGG GGTACAAGAC TTTTGGTGAA GAGATCCCAC
OsAHASL1.1  GAAGAGGGAG TTTCCTCTGG GGTACAAGAC TTTTGGTGAA GAGATCCCAC
OsAHASL1.2  GAAGAGGGAG TTTCCTCTGG GGTACAAGAC TTTTGGTGAA GAGATCCCAC
OsAHASL1.4  GAAGAGGGAG TTTCCTCTGG GGTACAAAAC TTTTGGTGAA GAGATCCCAC
OsAHASL1.6  GAAGAGGGAG TTTCCTCTGG GGTACAAAAC TTTTGGTGAA GAGATCCCAC
   ZmAHASL1 AAAGAGGGAG TTTCCCCTTG GATATAAAAT CTTCAATGAG GAAATCCAGC
   ZmAHASL2 GAAGAGGGAA TTCCCCCTTG GGTATAAAAC ATCTAATGAG GAGATCCAGC
   OsAHASL2 GAAGGTCGAG TTCCCACTGG GCTACAGAAC GTTCGGCGAG GAGATCCCGC
    AtAHASL GAAACAGAAG TTTCCGTTGA GCTTTAAGAC GTTTGGGGAA GCTATTCCTC 2001                                                    2050
SEQ ID NO:1 CGCAATATGC TATTCAGGTG CTGGATGAGC TGACGAAAGG GGAGGCAATC
OsAHASL1.1  CGCAATATGC TATTCAGGTG CTGGATGAGC TGACGAAAGG GGAGGCAATC
OsAHASL1.2  CGCAATATGC TATTCAGGTG CTGGATGAGC TGACGAAAGG GGAGGCAATC
OsAHASL1.4  CGCAATATGC CATTCAGGTG CTGGATGAGC TGACGAAAGG TGAGGCAATC
OsAHASL1.6  CGCAATATGC CATTCAGGTG CTGGATGAGC TGACGAAAGG TGAGGCAATC
   ZmAHASL1 CACAATATGC TATTCAGGTT CTTGATGAGT TGACGAAGGG GGAGGCCATC
   ZmAHASL2 CACAATATGC TATTCAGGTT CTTGATGAGC TGACGAAAGG CGAGGCCATC
   OsAHASL2 CGCAGTACGC CATCCAGGTG CTCGACGAGG TCACCAACGG GGAGGCCATC
    AtAHASL CACAGTATGC GATTAAGGTC CTTGATGAGT TGACTGATGG AAAAGCCATA
```

FIGURE 1 (continued)

```
            2051                                                  2100
SEQ ID NO:1 ATCGCTACTG GTGTTGGACA GCACCAGATG TGGGCGGCAC AATATTACAC
OsAHASL1.1  ATCGCTACTG GTGTTGGACA GCACCAGATG TGGGCGGCAC AATATTACAC
OsAHASL1.2  ATCGCTACTG GTGTTGGACA GCACCAGATG TGGGCGGCAC AATATTACAC
OsAHASL1.4  ATCGCTACTG GTGTTGGGCA GCACCAGATG TGGGCGGCAC AATATTACAC
OsAHASL1.6  ATCGCTACTG GTGTTGGGCA GCACCAGATG TGGGCGGCAC AATATTACAC
   ZmAHASL1 ATTGCCACAG GTGTTGGGCA GCACCAGATG TGGGCGGCAC AGTATTACAC
   ZmAHASL2 ATCGGCACAG GTGTTGGGCA GCACCAGATG TGGGCGGCAC AGTACTACAC
   OsAHASL2 GTCGCCACGG GCGTCGGGCA GCACCAGATG TGGGCGACGC AGCACTACAC
     AtAHASL ATAAGTACTG GTGTCGGGCA ACATCAAATG TGGGCGGCGC AGTTCTACAA 2101                                                  2150
SEQ ID NO:1 CTACAAGCGG CCACGGCAGT GGCTGTCTTC GGCTGGTCTG GGCGCAATGG
OsAHASL1.1  CTACAAGCGG CCACGGCAGT GGCTGTCTTC GGCTGGTCTG GGCGCAATGG
OsAHASL1.2  CTACAAGCGG CCACGGCAGT GGCTGTCTTC GGCTGGTCTG GGCGCAATGG
OsAHASL1.4  CTACAAGCGG CCACGGCAGT GGCTGTCTTC GGCTGGTCTG GGCGCAATGG
OsAHASL1.6  CTACAAGCGG CCACGGCAGT GGCTGTCTTC GGCTGGTCTG GGCGCAATGG
   ZmAHASL1 TTACAAGCGG CCAAGGCAGT GGCTGTCTTC AGCTGGTCTT GGGGCTATGG
   ZmAHASL2 TTACAAGCGG CCAAGGCAGT GGTTGTCTTC AGCTGGTCTT GGGGCTATGG
   OsAHASL2 CTACAGGAGG CCCAGGCAGT GGCTCTCGTC CGCCGGGCTG GGCGCCATGG
     AtAHASL TTACAAGAAG CCAAGGCAGT GGCTATCATC AGGAGGCCTT GGAGCTATGG 2151                                                  2200
SEQ ID NO:1 GATTTGGGCT GCCTGCTGCA GCTGGTGCTT CTGTGGCTAA CCCAGGTGTC
OsAHASL1.1  GATTTGGGCT GCCTGCTGCA GCTGGTGCTT CTGTGGCTAA CCCAGGTGTC
OsAHASL1.2  GATTTGGGCT GCCTGCTGCA GCTGGTGCTT CTGTGGCTAA CCCAGGTGTC
OsAHASL1.4  GATTTGGGCT GCCTGCTGCA GCTGGTGCTT CTGTGGCTAA CCCAGGTGTC
OsAHASL1.6  GATTTGGGCT GCCTGCTGCA GCTGGTGCTT CTGTGGCTAA CCCAGGTGTC
   ZmAHASL1 GATTTGGTTT GCCGGCTGCT GCTGGTGCTG CTGTGGCCAA CCCAGGTGTC
   ZmAHASL2 GATTTGGTTT GCCGGCTGCT GCTGGTGCTT CTGTGGCCAA CCCAGGTGTT
   OsAHASL2 GCTTCGGCCT GCCTGCCGCC GCCGGCGCCG CGGTGGCCAA CCCGGGCGCC
     AtAHASL GTTTTGGACT TCCTGCTGCC ATTGGAGCGT CTGTTGCTAA CCCTGATGCA 2201                                                  2250
SEQ ID NO:1 ACAGTTGTTG ATATTGATGG GGATGGTAGC TTCCTCATGA ACATTCAGGA
OsAHASL1.1  ACAGTTGTTG ATATTGATGG GGATGGTAGC TTCCTCATGA ACATTCAGGA
OsAHASL1.2  ACAGTTGTTG ATATTGATGG GGATGGTAGC TTCCTCATGA ACATTCAGGA
OsAHASL1.4  ACAGTTGTTG ATATTGATGG GGATGGTAGC TTCCTCATGA ACATTCAGGA
OsAHASL1.6  ACAGTTGTTG ATATTGATGG GGATGGTAGC TTCCTCATGA ACATTCAGGA
   ZmAHASL1 ACTGTTGTTG ACATCGACGG AGATGGTAGC TTCCTCATGA ACATTCAGGA
   ZmAHASL2 ACTGTTGTTG ACATCGATGG AGATGGTAGC TTTCTCATGA ACGTTCAGGA
   OsAHASL2 ACCGTGGTCG ACATCGACGG CGACGGCAGC CTCCTGATGA ACATCCAGGA
     AtAHASL ATAGTTGTGG ATATTGACGG AGATGGAAGC TTTATAATGA ATGTGCAAGA
```

FIGURE 1 (continued)

```
              2251                                                   2300
SEQ ID NO:1   GTTGGCATTG ATCCGCATTG AGAACCTCCC GGTGAAGGTG ATGGTGTTGA
OsAHASL1.1    GTTGGCATTG ATCCGCATTG AGAACCTCCC GGTGAAGGTG ATGGTGTTGA
OsAHASL1.2    GTTGGCATTG ATCCGCATTG AGAACCTCCC GGTGAAGGTG ATGGTGTTGA
OsAHASL1.4    GCTGGCATTG ATCCGCATTG AGAACCTCCC TGTGAAGGTG ATGGTGTTGA
OsAHASL1.6    GCTGGCATTG ATCCGCATTG AGAACCTCCC TGTGAAGGTG ATGGTGTTGA
   ZmAHASL1   GCTAGCTATG ATCCGTATTG AGAACCTCCC AGTCAAGGTC TTTGTGCTAA
   ZmAHASL2   GCTAGCTATG ATCCGAATTG AGAACCTCCC GGTGAAGGTC TTTGTGCTAA
   OsAHASL2   GCTCGCCATG GTCCGCGTCG AGGACCTGCC GGTGAAGGTG ATGGTGCTGA
    AtAHASL   GCTGGCCACA ATCCGTGTAG AGCAACTTCC AGTGAAGATA CTCTTATTAA 2301                                                   2350
SEQ ID NO:1   ACAACCAACA TTTGGGTATG GTTGTGCAAT GGGAGGATAG GTTTTACAAG
OsAHASL1.1    ACAACCAACA TTTGGGTATG GTTGTGCAAT GGGAGGATAG GTTTTACAAG
OsAHASL1.2    ACAACCAACA TTTGGGTATG GTTGTGCAAT GGGAGGATAG GTTTTACAAG
OsAHASL1.4    ACAACCAACA TTTGGGTATG GTGGTGCAAT GGGAGGATAG GTTTTACAAG
OsAHASL1.6    ACAACCAACA TTTGGGTATG GTGGTGCAAT TGGAGGATAG GTTTTACAAG
   ZmAHASL1   ACAACCAGCA CCTCGGGATG GTGGTGCAGT GGGAGGACAG GTTCTATAAG
   ZmAHASL2   ACAACCAGCA CCTGGGGATG GTGGTGCAGT GGGAGGACAG GTTCTATAAG
   OsAHASL2   ACAACCAGCA CCTGGGCATG GTGGTGCAGT GGGAGGACAG GTTCTACGAC
    AtAHASL   ACAACCAGCA TCTTGGCATG GTTATGCAAT GGGAAGATCG GTTCTACAAG 2351                                                   2400
SEQ ID NO:1   GCAAATAGGG CGCATACATA CTTGGGCAAC CCAG...... AATGTGAGAG
OsAHASL1.1    GCAAATAGGG CGCATACATA CTTGGGCAAC CCAG...... AATGTGAGAG
OsAHASL1.2    GCAAATAGGG CGCATACATA CTTGGGCAAC CCAG...... AATGTGAGAG
OsAHASL1.4    GCGAATAGGG CGCATACATA CTTGGGCAAC CCGG...... AATGTGAGAG
OsAHASL1.6    GCGAATAGGG CGCATACATA CTTGGGCAAC CCGG...... AATGTGAGAG
   ZmAHASL1   GCCAATAGAG CACACACATT CTTGGGAAAC CCAG...... AGAACGAAAG
   ZmAHASL2   GCCAACAGAG CGCACACATA CTTGGGAAAC CCAG...... AGAATGAAAG
   OsAHASL2   GCCAACAGGG CGCACACCTA CCTCGGCAAC CCGGCGGCGA ACGGCGGCGG
    AtAHASL   GCTAACCGAG CTCACACATT TCTCGGGGAT CCGG...... CTCAGGAGGA 2401                                                   2450
SEQ ID NO:1   TGAGATATAT CCAGATTTTG TGACTATTGC TAAAGGGTTC AATATTCCTG
OsAHASL1.1    TGAGATATAT CCAGATTTTG TGACTATTGC TAAAGGGTTC AATATTCCTG
OsAHASL1.2    TGAGATATAT CCAGATTTTG TGACTATTGC TAAAGGGTTC AATATTCCTG
OsAHASL1.4    CGAGATATAT CCAGATTTTG TGACTATTGC TAAGGGGTTC AATATTCCTG
OsAHASL1.6    CGAGATATAT CCAGATTTTG TGACTATTGC TAAGGGGTTC AATATTCCTG
   ZmAHASL1   TGAGATATAT CCAGATTTTG TGGCAATTGC TAAAGGGTTC AACATTCCAG
   ZmAHASL2   TGAGATATAT CCAGATTTCG TGACGATCGC CAAAGGGTTC AACATTCCAG
   OsAHASL2   CGAGGTGTAC CCGGACTTCG TGACGATCGC CGGAGGCTTC GGCATCCCGG
    AtAHASL   CGAGATATTC CCGAACATGT TGCTGTTTGC AGCAGCTTGC GGGATTCCAG
```

FIGURE 1 (continued)

```
            2451                                                    2500
SEQ ID NO:1 CAGTCCGTGT AACAAAGAAG AGTGAAGTCC GTGCCGCCAT CAAGAAGATG
OsAHASL1.1  CAGTCCGTGT AACAAAGAAG AGTGAAGTCC GTGCCGCCAT CAAGAAGATG
OsAHASL1.2  CAGTCCGTGT AACAAAGAAG AGTGAAGTCC GTGCCGCCAT CAAGAAGATG
OsAHASL1.4  CAGTCCGTGT AACAAAGAAG AGTGAAGTCC GTGCCGCCAT CAAGAAGATG
OsAHASL1.6  CAGTCCGTGT AACAAAGAAG AGTGAAGTCC GTGCCGCCAT CAAGAAGATG
  ZmAHASL1  CAGTCCGTGT GACAAAGAAG AGCGAAGTCC ATGCAGCAAT CAAGAAGATG
  ZmAHASL2  CGGTCCGTGT GACAAAGAAG AACGAAGTCC GCGCAGCGAT AAAGAAGATG
  OsAHASL2  CGGCCCGCGT GACGAGGAAG GGCGAGGTCC GCGCCGCCGT CGAGGAGATG
   AtAHASL  CGGCGAGGGT GACAAAGAAA GCAGATCTCC GAGAAGCTAT TCAGACAATG 2501                                                    2550
SEQ ID NO:1 CTCGATACCC CAGGGCCATA CTTGTTGGAT ATCATCGTCC CACACCAGGA
OsAHASL1.1  CTCGATACCC CAGGGCCATA CTTGTTGGAT ATCATCGTCC CACACCAGGA
OsAHASL1.2  CTCGATACCC CAGGGCCATA CTTGTTGGAT ATCATCGTCC CACACCAGGA
OsAHASL1.4  CTCGAGACTC CAGGGCCATA CTTGTTGGAT ATCATCGTCC CGCACCAGGA
OsAHASL1.6  CTCGAGACTC CAGGGCCATA CTTGTTGGAT ATCATCGTCC CGCACCAGGA
  ZmAHASL1  CTTGAGGCTC CAGGGCCGTA CCTCTTGGAT ATAATCGTCC CGCACCAGGA
  ZmAHASL2  CTCGAGACTC CAGGGCCGTA CCTCTTGGAT ATAATCGTCC CACACCAGGA
  OsAHASL2  ATGGCGGCGC CGGGGCCGTA CCTGCTGGAC GTCGTCGTGC CTCACCAGGA
   AtAHASL  CTGGATACAC CAGGACCTTA CCTGTTGGAT GTGATTTGTC CGCACCAAGA 2551                                                    2600
SEQ ID NO:1 GCATGTGCTG CCTATGATCC CAAGTGGGGG CGCATTCAAG GACATGATCC
OsAHASL1.1  GCATGTGCTG CCTATGATCC CAAGTGGGGG CGCATTCAAG GACATGATCC
OsAHASL1.2  GCATGTGCTG CCTATGATCC CAAGTGGGGG CGCATTCAAG GACATGATCC
OsAHASL1.4  GCATGTGCTG CCTATGATCC CAAGTGGGGG CGCATTCAAG GACATGATCC
OsAHASL1.6  GCATGTGCTG CCTATGATCC CAATTGGGGG CGCATTCAAG GACATGATCC
  ZmAHASL1  GCATGTGTTG CCTATGATCC CTAGTGGTGG GGCTTTCAAG GATATGATCC
  ZmAHASL2  GCATGTGTTG CCTATGATCC CTAGTGGTGG GGCTTTCAAG GATATGATCC
  OsAHASL2  GCACGTGCTG CCGATGATCC CCAGCAATGG CGCTTTCAAG GACATTATCG
   AtAHASL  ACATGTGTTG CCGATGATCC CGAGTGGTGG CACTTTCAAC GATGTCATAA 2601                                                    2650
SEQ ID NO:1 TGGATGGTGA TGGCAGGACT GTGTATTAAT CTATA.ATCT GTATGTTGGC
OsAHASL1.1  TGGATGGTGA TGGCAGGACT GTGTATTAAT CTATA.ATCT GTATGTTGGC
OsAHASL1.2  TGGATGGTGA TGGCAGGACT GTGTATTAAT CTATA.ATCT GTATGTTGGC
OsAHASL1.4  TGGATGGTGA TGGCAGGACT GTGTATTAAT CTATA.ATCT GTATGTTGGC
OsAHASL1.6  TGGATGGTGA TGGCAGGACT GTGTATTAAT CTATA.ATCT GTATGTTGGC
  ZmAHASL1  TGGATGGTGA TGGCAGGACT GTGTATTGAT CCGTTGA.CT GCAGGTCGAC
  ZmAHASL2  TGGATGGTGA TGGCAGGACT GTGTACTGAT CTAAAATCCA GCAAGCAACT
  OsAHASL2  TCGACGGTGA TGGCCGGAGT TCGTATTAG. .......... ..........
   AtAHASL  CGGAAGGAGA TGGCCGGATT AAATACTGA. .......... ..........
```

FIGURE 2

```
            1                                                    50
SEQ ID NO:2 ....MATTAA AAAATLSAAA TAKTGRKNHQ RHHVFPARGR VGAAA.....
OsAHASL1.1  ....MATTAA AAAATLSAAA TAKTGRKNHQ RHHVFPARGR VGAAA.....
OsAHASL1.2  ....MATTAA AAAATLSAAA TAKTGRKNHQ RHHVFPARGR VGAAA.....
OsAHASL1.4  ....MATTAA AAAAALSAAA TAKTGRKNHQ RHHVLPARGR VGAAA.....
OsAHASL1.6  ....MATTAA AAAAALSAAA TAKTGRKNHQ RHHVLPARGR VGAAA.....
   ZmAHASL1 ....MATAAT AAAALT GATTATPKSR RRAHHLATRR ALAAP.....
   ZmAHASL2 ....MATAAA ASTALT GATTAAPKAR RRAHLLATRR ALAAP.....
   OsAHASL2 ....MAAAAA AASLSVSDAA AKLPKPGGQV QRRRDRDRPR VDAAACTRDS
    AtAHASL ....MAAATT TTTTSSSISF STKPSPSSSK SPLPISRFSL PFSLNPNKSS 51                                                  100
SEQ ID NO:2 .......... .......... .VRCSAVSPV TPPSPAPPAT PLRPWGPAEP
OsAHASL1.1  .......... .......... .VRCSAVSPV TPPSPAPPAT PLRPWGPAEP
OsAHASL1.2  .......... .......... .VRCSAVSPV TPPSPAPPAT PLRPWGPAEP
OsAHASL1.4  .......... .......... .VRCSAVSPV TPPSPAPPAT PLRPWGPAEP
OsAHASL1.6  .......... .......... .VRCSAVSPV TPPSPAPPAT PLRPWGPAEP
   ZmAHASL1 .......... .......... .IRCSALSRA TPT..APPAT PLRPWGPNEP
   ZmAHASL2 .......... .......... .IRCSAASPA MPM..APPAT PLRPWGPTDP
   OsAHASL2 RRPTRERC.. .......... STTVSLAATA TATTATPVRA PVRTRAPMGQ
    AtAHASL SSSRRRGIKS SSPSSISAVL NTTTNVTTTP SPTKPTKPET FISRFAPDQP 101                                                 150
SEQ ID NO:2 RKGADILVEA LERCGVSDVF AYPGGASMEI HQALTRSPVI TNHLFRHEQG
OsAHASL1.1  RKGADILVEA LERCGVSDVF AYPGGASMEI HQALTRSPVI TNHLFRHEQG
OsAHASL1.2  RKGADILVEA LERCGVSDVF AYPGGASMEI HQALTRSPVI TNHLFRHEQG
OsAHASL1.4  RKGADILVEA LERCGVSDVF AYPGGASMEI HQALTRSPVI TNHLFRHEQG
OsAHASL1.6  RKGADILVEA LERCGVSDVF AYPGGASMEI HQALTRSPVI TNHLFRHEQG
   ZmAHASL1 RKGSDILVEA LERCGVRDVF AYPGGASMEI HQALTRSPVI ANHLFRHEQG
   ZmAHASL2 RKGADILVES LERCGVRDVF AYPGGASMEI HQALTRSPVI ANHLFRHEQG
   OsAHASL2 RKGADIVVEA LERCGVRDVF EYPGGASMEI HQALTRSPVI RNHLLRHEQG
    AtAHASL RKGADILVEA LERQGVETVF AYPGGASMEI HQALTRSSSI RNVLPRHEQG 151                                                 200
SEQ ID NO:2 EAFAASGYAR ASGRVGVCVA TSGPGATNLV SALADALLDS VPMVAITGQV
OsAHASL1.1  EAFAASGYAR ASGRVGVCVA TSGPGATNLV SALADALLDS VPMVAITGQV
OsAHASL1.2  EAFAASGYAR ASGRVGVCVA TSGPGATNLV SALADALLDS VPMVAITGQV
OsAHASL1.4  EAFAASGYAR ASGRVGVCVA TSGPGATNLV SALADALLDS VPMVAITGQV
OsAHASL1.6  EAFAASGYAR ASGRVGVCVA TSGPGATNLV SALADALLDS VPMVAITGQV
   ZmAHASL1 EAFAASAYAR SSGRVGVCIA TSGPGATNLV SALADALLDS VPMVAITGQV
   ZmAHASL2 EAFAASGYAR SSGRVGVCIA TSGPGATNLV SALADALLDS VPMVAITGQV
   OsAHASL2 EAFAASGYAR SSGRPGVCVA TSGPGATNLV SALADAHLDS VPLVAITGQA
    AtAHASL GVFAAEGYAR SSGKPGICIA TSGPGATNLV SGLADALLDS VPLVAITGQV
```

FIGURE 2 (continued)

```
            201                                                        250
SEQ ID NO:2 PRRMIGTDVF QETPIVEVTR SITKHNYLVL DVEDIPRVIQ EAFFLASSGR
OsAHASL1.1  PRRMIGTDAF QETPIVEVTR SITKHNYLVL DVEDIPRVIQ EAFFLASSGR
OsAHASL1.2  PRRMIGTDAF QETPIVEVTR SITKHNYLVL DVEDIPRVIQ EAFFLASSGR
OsAHASL1.4  PRRMIGTDAF QETPIVEVTR SITKHNYLVL DVEDIPRVIQ EAFFLASSGR
OsAHASL1.6  PRRMIGTDAF QETPIVEVTR SITKHNYLVL DVEDIPRVIQ EAFFLASSGR
  ZmAHASL1  PRRMIGTDAF QETPIVEVTR SITKHNYLVL DVDDIPRVVQ EAFFLASSGR
  ZmAHASL2  PRRMIGTDAF QETPIVEVTR SITKHNYLVL DVDDIPRVVQ EAFFLASSGR
  OsAHASL2  PRRMIGTDAF QETPIVEFTR SITKHNYLIL DVDDIPRVIN EAFFLASTGR
   AtAHASL  PRRMIGTDAF QETPIVEVTR SITKHNYLVM DVEDIPRIIE EAFFLATSGR 251                                                        300
SEQ ID NO:2 PGPVLVDIPK DIQQQMAVPV WDTSMNLPGY IARLPKPPAT ELLEQVLRLV
OsAHASL1.1  PGPVLVDIPK DIQQQMAVPV WDTSMNLPGY IARLPKPPAT ELLEQVLRLV
OsAHASL1.2  PGPVLVDIPK DIQQQMAVPV WDTSMNLPGY IARLPKPPAT ELLEQVLRLV
OsAHASL1.4  PGPVLVDIPK DIQQQMAVPV WDTSMNLPGY IARLPKPPAT ELLEQVLRLV
OsAHASL1.6  PGPVLVDIPK DIQQQMAVPV WDTSMNLPGY IARLPKPPAT ELLEQVLRLV
  ZmAHASL1  PGPVLVDIPK DIQQQMAVPA WDTPMSLPGY IARLPKPPAT EFLEQVLRLV
  ZmAHASL2  PGPVLVDIPK DIQQQMAVPV WDKPMSLPGY IARLPKPPAT ELLEQVLRLV
  OsAHASL2  PGPVLVDIPK DIQQQMAVPS WDAPMRLPGY ISRLPKPPAA NLLDEVIRLV
   AtAHASL  PGPVLVDVPK DIQQQLAIPN WEQAMRLPGY MSRMPKPPED SHLEQIVRLI 301                                                        350
SEQ ID NO:2 GESRRPILYV GGGCSASGDE LRRFVELTGI PVTTTLMGLG NFPSDDPLSL
OsAHASL1.1  GESRRPILYV GGGCSASGDE LRRFVELTGI PVTTTLMGLG NFPSDDPLSL
OsAHASL1.2  GESRRPILYV GGGCSASGDE LRRFVELTGI PVTTTLMGLG NFPSDDPLSL
OsAHASL1.4  GESRRPILYV GGGCSASGDE LRWFVELTGI PVTTTLMGLG NFPSDDPLSL
OsAHASL1.6  GESRRPILYV GGGCSASGDE LRWFVELTGI PVTTTLMGLG NFPSDDPLSL
  ZmAHASL1  GESRRPVLYV GGGCAASGEE LCRFVELTGI PVTTTLMGLG NFPSDDPLSL
  ZmAHASL2  GESRRPVLYV GGGCAASGEE LRRFVELTGI PVTTTLMGLG NFPSDDPLSL
  OsAHASL2  GDAERPVLYV GGGCSASGYE LRRFVELTGI PVTTTLMGIG NFPSDDPLSL
   AtAHASL  SESKKPVLYV GGGCLNSSDE LGRFVELTGI PVASTLMGLG SYPCDDELSL 351                                                        400
SEQ ID NO:2 RMLGMHGTVY ANYAVDKADL LLAFGVRFDD RVTGKIEAFA SRAKIVHIDI
OsAHASL1.1  RMLGMHGTVY ANYAVDKADL LLAFGVRFDD RVTGKIEAFA SRAKIVHIDI
OsAHASL1.2  RMLGMHGTVY ANYAVDKADL LLAFGVRFDD RVTGKIEAFA SRAKIVHIDI
OsAHASL1.4  RMLGMHGTVY ANYAVDKADL LLAFGVRFDD RVTGKIEAFA SRAKIVHIDI
OsAHASL1.6  RMLGMHGTVY ANYAVDKADL LLAFGVRFDD RVTGKIEAFA SRAKIVHIDI
  ZmAHASL1  RMLGMHGTVY ANYAVDKADL LLAFGVRFDD RVTGKIEAFA GRAKIVHIDI
  ZmAHASL2  RMLGMHGTVY ANYAVDKADL LLALGVRFDD RVTGKIEAFA SRAKIVHVDI
  OsAHASL2  RMLGMHGTVY ANYAVDNADL LLALGVRFDD RVTGKVEAFA SRAKIVHVDI
   AtAHASL  HMLGMHGTVY ANYAVEHSDL LLAFGVRFDD RVTGKLEAFA SRAKIVHIDI
```

FIGURE 2 (continued)

```
           401                                                       450
SEQ ID NO:2 DPAEIGKNKQ PHVSICADVK LALQGLNALL D...QSTTKT SSDFSAWHNE
OsAHASL1.1  DPAEIGKNKQ PHVSICADVK LALQGLNALL D...QSTTKT SSDFSAWHNE
OsAHASL1.2  DPAEIGKNKQ PHVSICADVK LALQGLNALL D...QSTTKT SSDFSAWHNE
OsAHASL1.4  DPAEIGKNKQ PHVSICADVK LALQGLNALL Q...QSTTKT SSDFSAWHNE
OsAHASL1.6  DPAEIGKNKQ PHVSICADVK LALQGLNALL Q...QSTTKT SSDFSAWHNE
  ZmAHASL1  DPAEIGKNKQ PHVSICADVK LALQGMNTLL E...GSTSKK SFDFGSWHDE
  ZmAHASL2  DPAEIGKNKQ PHVSICADVK LALQGMNALL E...GSTSKK SFDFGSWNDE
  OsAHASL2  DPSELGKNKQ PHVSICADVK LALQGMNAML EEQSAAAARK NLDFSAWRSE
   AtAHASL  DSAEIGKNKT PHVSVCGDVK LALQGMNKVL E...NRAEEL KLDFGVWRNE 451                                                       500
SEQ ID NO:2 LDQQKREFPL GYKTFGEEIP PQYAIQVLDE LTKGEAIIAT GVGQHQMWAA
OsAHASL1.1  LDQQKREFPL GYKTFGEEIP PQYAIQVLDE LTKGEAIIAT GVGQHQMWAA
OsAHASL1.2  LDQQKREFPL GYKTFGEEIP PQYAIQVLDE LTKGEAIIAT GVGQHQMWAA
OsAHASL1.4  LDQQKREFPL GYKTFGEEIP PQYAIQVLDE LTKGEAIIAT GVGQHQMWAA
OsAHASL1.6  LDQQKREFPL GYKTFGEEIP PQYAIQVLDE LTKGEAIIAT GVGQHQMWAA
  ZmAHASL1  LDQQKREFPL GYKIFNEEIQ PQYAIQVLDE LTKGEAIIAT GVGQHQMWAA
  ZmAHASL2  LDQQKREFPL GYKTSNEEIQ PQYAIQVLDE LTKGEAIIGT GVGQHQMWAA
  OsAHASL2  LEKKKVEFPL GYRTFGEEIP PQYAIQVLDE VTNGEAIVAT GVGQHQMWAT
   AtAHASL  LNVQKQKFPL SFKTFGEAIP PQYAIKVLDE LTDGKAIIST GVGQHQMWAA 501                                                       550
SEQ ID NO:2 QYYTYKRPRQ WLSSAGLGAM GFGLPAAAGA SVANPGVTVV DIDGDGSFLM
OsAHASL1.1  QYYTYKRPRQ WLSSAGLGAM GFGLPAAAGA SVANPGVTVV DIDGDGSFLM
OsAHASL1.2  QYYTYKRPRQ WLSSAGLGAM GFGLPAAAGA SVANPGVTVV DIDGDGSFLM
OsAHASL1.4  QYYTYKRPRQ WLSSAGLGAM GFGLPAAAGA SVANPGVTVV DIDGDGSFLM
OsAHASL1.6  QYYTYKRPRQ WLSSAGLGAM GFGLPAAAGA SVANPGVTVV DIDGDGSFLM
  ZmAHASL1  QYYTYKRPRQ WLSSAGLGAM GFGLPAAAGA AVANPGVTVV DIDGDGSFLM
  ZmAHASL2  QYYTYKRPRQ WLSSAGLGAM GFGLPAAAGA SVANPGVTVV DIDGDGSFLM
  OsAHASL2  QHYTYRRPRQ WLSSAGLGAM GFGLPAAAGA AVANPGATVV DIDGDGSLLM
   AtAHASL  QFYNYKKPRQ WLSSGGLGAM GFGLPAAIGA SVANPDAIVV DIDGDGSFIM 551                                                       600
SEQ ID NO:2 NIQELALIRI ENLPVKVMVL NNQHLGMVVQ WEDRFYKANR AHTYLGNP..
OsAHASL1.1  NIQELALIRI ENLPVKVMVL NNQHLGMVVQ WEDRFYKANR AHTYLGNP..
OsAHASL1.2  NIQELALIRI ENLPVKVMVL NNQHLGMVVQ WEDRFYKANR AHTYLGNP..
OsAHASL1.4  NIQELALIRI ENLPVKVMVL NNQHLGMVVQ WEDRFYKANR AHTYLGNP..
OsAHASL1.6  NIQELALIRI ENLPVKVMVL NNQHLGMVVQ LEDRFYKANR AHTYLGNP..
  ZmAHASL1  NIQELAMIRI ENLPVKVFVL NNQHLGMVVQ WEDRFYKANR AHTFLGNP..
  ZmAHASL2  NVQELAMIRI ENLPVKVFVL NNQHLGMVVQ WEDRFYKANR AHTYLGNP..
  OsAHASL2  NIQELAMVRV EDLPVKVMVL NNQHLGMVVQ WEDRFYDANR AHTYLGNPAA
   AtAHASL  NVQELATIRV ENLPVKVLLL NNQHLGMVMQ WEDRFYKANR AHTFLGDP..
```

FIGURE 2 (continued)

```
             601                                                      650
SEQ ID NO:2  ECESEIYPDF  VTIAKGFNIP  AVRVTKKSEV  RAAIKKMLDT  PGPYLLDIIV
OsAHASL1.1   ECESEIYPDF  VTIAKGFNIP  AVRVTKKSEV  RAAIKKMLDT  PGPYLLDIIV
OsAHASL1.2   ECESEIYPDF  VTIAKGFNIP  AVRVTKKSEV  RAAIKKMLDT  PGPYLLDIIV
OsAHASL1.4   ECESEIYPDF  VTIAKGFNIP  AVRVTKKSEV  RAAIKKMLET  PGPYLLDIIV
OsAHASL1.6   ECESEIYPDF  VTIAKGFNIP  AVRVTKKSEV  RAAIKKMLET  PGPYLLDIIV
   ZmAHASL1  ENESEIYPDF  VAIAKGFNIP  AVRVTKKSEV  HAAIKKMLEA  PGPYLLDIIV
   ZmAHASL2  ENESEIYPDF  VTIAKGFNIP  AVRVTKKNEV  RAAIKKMLET  PGPYLLDIIV
   OsAHASL2  NGGGEVYPDF  VTIAGGFGIP  AARVTRKGEV  RAAVEEMMAA  PGPYLLDVVV
    AtAHASL  AQEDEIFPNM  LLFAAACGIP  AARVTKKADL  REAIQTMLDT  PGPYLLDVIC 651                                                      700
SEQ ID NO:2  PHQEHVLPMI  PSGGAFKDMI  LDGDGRTVY.
OsAHASL1.1   PHQEHVLPMI  PSGGAFKDMI  LDGDGRTVY.
OsAHASL1.2   PHQEHVLPMI  PSGGAFKDMI  LDGDGRTVY.
OsAHASL1.4   PHQEHVLPMI  PSGGAFKDMI  LDGDGRTVY
OsAHASL1.6   PHQEHVLPMI  PIGGAFKDMI  LDGDGRTVY.
   ZmAHASL1  PHQEHVLPMI  PSGGAFKDMI  LDGDGRTVY.
   ZmAHASL2  PHQEHVLPMI  PSGGAFKDMI  LDGDGRTVY.
   OsAHASL2  PHQEHVLPMI  PSNGAFKDII  VDGDGRSSY.
    AtAHASL  PHQEHVLPMI  PSGGTFNDVI  TEGDGRIKY.
```

HERBICIDE-RESISTANT RICE PLANTS, POLYNUCLEOTIDES ENCODING HERBICIDE-RESISTANT ACETOHYDROXYACID SYNTHASE LARGE SUBUNIT PROTEINS, AND METHODS OF USE

CROSS-REFERENCE TO RELATED APPLICATIONS

This application is the U.S. National Stage of International Application PCT/US2006/007343 filed Feb. 28, 2006, which was published by the International Bureau on Sep. 8, 2006 and which claims the benefit of U.S. Provisional Application No. 60/657,968 filed Mar. 2, 2005; all of which are hereby incorporated herein in their entirety by reference.

FIELD OF THE INVENTION

This invention relates to the field of agricultural biotechnology, particularly to herbicide-resistant rice plants and to novel polynucleotide sequences that encode herbicide-resistant acetohydroxy acid synthase large subunit proteins.

BACKGROUND OF THE INVENTION

Weeds are one of the major constraints to rice production. Direct seeding has reduced the labor problems of transplanting; however, this technology has helped to increase the weed problem. Herbicide use in rice is a common practice in most of the rice regions under direct seeding crop and/or developed countries that grow rice under either transplanting or direct seeding systems. Usually a grass and a broadleaf herbicide are applied one or more times in order to control weeds in rice crops.

Grasses, sedges and weedy rice (red rice) have been the major groups of species that possess high fitness to the same environments where rice is grown. They have become globally distributed and are difficult to control weeds in rice crops. Although there are several cultural practices that aid in control of weeds and are convenient for better environmental care, these practices impose restrictions and increase production costs. Land preparation, land leveling, levees and depth of water, land rotation, certified seed, proper plant systems and dates of planting could be some of the cultural practices that may help to reduce the weed seed bank and the development of herbicide-tolerant weeds.

In spite of the many recommendations for better cultural practices the farmers still rely on the use of herbicides as the main tool to control weeds. The use and abuse of some of these chemicals has resulted in the development of tolerant weeds like propanil-resistant and butachlor-resistant barnyardgrass (*Echinochloa crus galli*). In these cases, it would be convenient to have other herbicides with different modes of action with the ability to control most of these weed species. The availability of such herbicides would allow for a rotation of herbicides with a different mode of action than those herbicides that are commonly used in rice production.

Imidazolinones are a group of herbicides with a different mode of action than the commonly used rice herbicides. These herbicides are known to inhibit acetohydroxyacid synthase (AHAS; EC 4.1.3.18, also known as acetolactate synthase or ALS), a key enzyme for the biosynthesis of branched-chain amino acids. Inn particular, acetohydroxyacid synthase (AHAS; EC 4.1.3.18, also known as aceto-lactate synthase or ALS), is the first enzyme that catalyzes the biochemical synthesis of the branched chain amino acids valine, leucine and isoleucine (Singh (1999) "Biosynthesis of valine, leucine and isoleucine," in *Plant Amino Acid*, Singh, B. K., ed., Marcel Dekker Inc. New York, New York, pp. 227-247). AHAS is the site of action of four structurally diverse herbicide families including the sulfonylureas (LaRossa and Falco (1984) *Trends Biotechnol.* 2:158-161), the imidazolinones (Shaner et al. (1984) *Plant Physiol.* 76:545-546), the triazolopyrimidines (Subramanian and Gerwick (1989) "Inhibition of acetolactate synthase by triazolopyrimidines," in *Biocatalysis in Agricultural Biotechnology*, Whitaker, J. R. and Sonnet, P. E. eds., ACS Symposium Series, American Chemical Society, Washington, D.C., pp. 277-288), and the pyrimidyloxybenzoates (Subramanian et al. (1990) *Plant Physiol.* 94: 239-244.). Imidazolinone and sulfonylurea herbicides are widely used in modern agriculture due to their effectiveness at very low application rates and relative non-toxicity in animals. By inhibiting AHAS activity, these families of herbicides prevent further growth and development of susceptible plants including many weed species. Several examples of commercially available imidazolinone herbicides are PURSUIT® (imazethapyr), SCEPTER® (imazaquin) and ARSENAL® (imazapyr). Examples of sulfonylurea herbicides are chlorsulfuron, metsulfuron methyl, sulfometuron methyl, chlorimuron ethyl, thifensulfuron methyl, tribenuron methyl, bensulfuron methyl, nicosulfuron, ethametsulfuron methyl, rimsulfuron, triflusulfuron methyl, triasulfuron, primisulfuron methyl, cinosulfuron, amidosulfiuon, flazasulfuron, imazosulfuron, pyrazosulfuron ethyl and halosulfuron.

Due to their high effectiveness and low-toxicity, imidazolinone herbicides are favored for application by spraying over the top of a wide area of vegetation. The ability to spray an herbicide over the top of a wide range of vegetation decreases the costs associated with plantation establishment and maintenance, and decreases the need for site preparation prior to use of such chemicals. Spraying over the top of a desired tolerant species also results in the ability to achieve maximum yield potential of the desired species due to the absence of competitive species. However, the ability to use such spray-over techniques is dependent upon the presence of imidazolinone-resistant species of the desired vegetation in the spray over area.

Among the major agricultural crops, some leguminous species such as soybean are naturally resistant to imidazolinone herbicides due to their ability to rapidly metabolize the herbicide compounds (Shaner and Robinson (1985) *Weed Sci.* 33:469-471). Other crops such as corn (Newhouse et al. (1992) *Plant Physiol.* 100:882-886) and rice (Barrett et al. (1989) *Crop Safeners for Herbicides*, Academic Press, New York, pp. 195-220) are somewhat susceptible to imidazolinone herbicides. The differential sensitivity to the imidazolinone herbicides is dependent on the chemical nature of the particular herbicide and differential metabolism of the compound from a toxic to a non-toxic form in each plant (Shaner et al. (1984) *Plant Physiol.* 76:545-546; Brown et al., (1987) *Pestic. Biochem. Physiol.* 27:24-29). Other plant physiological differences such as absorption and translocation also play an important role in sensitivity (Shaner and Robinson (1985) *Weed Sci.* 33:469-471).

Plants resistant to imidazolinones, sulfonylureas and triazolopyrimidines have been successfully produced using seed, microspore, pollen, and callus mutagenesis in *Zea mays, Arabidopsis thaliana, Brassica napus* (i.e., canola) *Glycine max, Nicotiana tabacum*, and *Oryza sativa* (Sebastian et al. (1989) *Crop Sci.* 29:1403-1408; Swanson et al., 1989 *Theor. Appl. Genet.* 78:525-530; Newhouse et al. (1991) *Theor. Appl. Genet.* 83:65-70; Sathasivan et al.

(1991) *Plant Physiol.* 97:1044-1050; Mourand et al. (1993) *J. Heredity* 84:91-96; U.S. Pat. No. 5,545,822). In all cases, a single, partially dominant nuclear gene conferred resistance. Four imidazolinone resistant wheat plants were also previously isolated following seed mutagenesis of *Triticum aestivum* L. cv. Fidel (Newhouse et al. (1992) *Plant Physiol.* 100:882-886). Inheritance studies confirmed that a single, partially dominant gene conferred resistance. Based on allelic studies, the authors concluded that the mutations in the four identified lines were located at the same locus. One of the Fidel cultivar resistance genes was designated FS-4 (Newhouse et al. (1992) *Plant Physiol.* 100:882-886).

Computer-based modeling of the three dimensional conformation of the AHAS-inhibitor complex predicts several amino acids in the proposed inhibitor binding pocket as sites where induced mutations would likely confer selective resistance to imidazolinones (Ott et al. (1996) *J. Mol. Biol.* 263:359-368). Wheat plants produced with some of these rationally designed mutations in the proposed binding sites of the AHAS enzyme have in fact exhibited specific resistance to a single class of herbicides (Ott et al. (1996) *J. Mol. Biol.* 263:359-368).

Plant resistance to imidazolinone herbicides has also been reported in a number of patents. U.S. Pat. Nos. 4,761,373, 5,331,107, 5,304,732, 6,211,438, 6,211,439 and 6,222,100 generally describe the use of an altered AHAS gene to elicit herbicide resistance in plants, and specifically discloses certain imidazolinone resistant corn lines. U.S. Pat. No. 5,013,659 discloses plants exhibiting herbicide resistance due to mutations in at least one amino acid in one or more conserved regions. The mutations described therein encode either cross-resistance for imidazolinones and sulfonylureas or sulfonylurea-specific resistance, but imidazolinone-specific resistance is not described. U.S. Pat. Nos. 5,731,180 and 5,767,361 discuss an isolated gene having a single amino acid substitution in a wild-type monocot AHAS amino acid sequence that results in imidazolinone-specific resistance. In addition, rice plants that are resistant to herbicides that interfere with AHAS have been developed by mutation breeding and also by the selection of herbicide resistant plants from a pool of rice plants produced by another culture. See, U.S. Pat. Nos. 5,545,822, 5,736,629, 5,773,703, 5,773,704, 5,952,553 and 6,274,796.

In plants, as in all other organisms examined, the AHAS enzyme is comprised of two subunits: a large subunit (catalytic role) and a small subunit (regulatory role) (Duggleby and Pang (2000) *J. Biochem. Mol. Biol.* 33:1-36). The AHAS large subunit (also referred to herein as AHASL) may be encoded by a single gene as in the case of *Arabidopsis* and rice or by multiple gene family members as in maize, canola, and cotton. Specific, single-nucleotide substitutions in the large subunit confer upon the enzyme a degree of insensitivity to one or more classes of herbicides (Chang and Duggleby (1998) *Biochem J.* 333:765-777).

For example, bread wheat, *Triticum aestivum* L., contains three homoeologous acetohydroxyacid synthase large subunit genes. Each of the genes exhibit significant expression based on herbicide response and biochemical data from mutants in each of the three genes (Ascenzi et al. (2003) International Society of Plant Molecular Biologists Congress, Barcelona, Spain, Ref. No. S10-17). The coding sequences of all three genes share extensive homology at the nucleotide level (WO 03/014357). Through sequencing the AHASL genes from several varieties of *Triticum aestivum*, the molecular basis of herbicide tolerance in most IMI-tolerant (imidazolinone-tolerant) lines was found to be the mutation S653(At)N, indicating a serine to asparagine substitution at a position equivalent to the serine at amino acid 653 in *Arabidopsis thaliana* (WO 03/01436; WO 03/014357). This mutation is due to a single nucleotide polymorphism (SNP) in the DNA sequence encoding the AHASL protein.

Given their high effectiveness and low-toxicity, imidazolinone herbicides are favored for agricultural use. However, the ability to use imidazolinone herbicides in a particular crop production system depends upon the availability of imidazolinone-resistant varieties of the crop plant of interest. To produce such imidazolinone-resistant varieties, plant breeders need to develop breeding lines with the imidazolinone-resistance trait. Thus, additional imidazolinone-resistant breeding lines and varieties of crop plants, as well as methods and compositions for the production and use of imidazolinone-resistant breeding lines and varieties, are needed.

SUMMARY OF THE INVENTION

The present invention provides rice plants having increased resistance to herbicides when compared to a wild-type rice plant. In particular, the rice plants of the invention have increased resistance to imidazolinone and sulfonylurea herbicides, when compared to a wild-type rice plant. The herbicide resistant rice plants of the invention comprise at least one copy of a gene or polynucleotide that encodes a herbicide-resistant acetohydroxyacid synthase large subunit 1 (AHASL1) that comprise an amino acid substitution relative to the amino acid sequence of a wild-type. rice AHASL1 protein. In one embodiment of the invention, the herbicide-resistant rice plants comprise a herbicide-resistant AHASL1 protein that comprises a valine or aspartate at amino acid position 179 or equivalent position. The herbicide-resistant rice plant of the invention can contain one, two, three, four, or more copies of a gene or polynucleotide encoding a herbicide-resistant AHASL1 protein of the invention. The rice plants of the invention also include seeds and progeny plants that comprise at least one copy of a gene or polynucleotide encoding a herbicide-resistant AHASL1 of the invention.

The present invention provides herbicide-resistant rice plants that are from the rice line that has been designated as IMINTA 16. A sample of seeds of the IMINTA 16 line has been deposited with the patent depository at NCIMB Ltd. and assigned NCIMB Accession Number NCIMB 41262. The IMINTA 16 rice plants comprise in their genomes an AHASL1 gene that comprises the nucleotide sequences set forth in SEQ ID NOS: 1 and 3, or that encodes the AHASL1 protein comprising, the amino acid sequence set forth in SEQ ID NO: 2. When compared to the amino acid sequence of the AHASL1 protein that is encoded by an AHASL1 gene from a wild-type rice plant (GenBank Accession No. AB049822), the amino acid sequence set forth in SEQ ID NO: 2 possesses a single amino acid difference from the wild-type amino acid sequence. In the amino acid sequence set forth in SEQ ID NO: 2, there is a valine at amino acid position 179. In the amino acid sequence of the wild-type, rice AHASL1 protein, this same amino acid position has an alanine.

The present invention further provides isolated polynucleotides and isolated polypeptides for rice (*Oryza sativa*) AHASL1 proteins. The polynucleotides of the invention encompass nucleotide sequences that encode herbicide-resistant AHASL1 proteins. The herbicide-resistant AHASL1 proteins of the invention are imidazolinone-resistant AHASL1 proteins that comprise an alanine-to-valine substitution at position 179 in their respective amino acid sequences, when compared to the corresponding wild-type amino acid sequence. The polynucleotides of the invention encompass the nucleotide sequences set forth in SEQ ID NOS: 1 and 3, nucleotide sequences encoding the amino acid sequence set forth in SEQ ID NO: 2, and fragments and variants of said nucleotide sequences that encode proteins comprising AHAS activity, particularly herbicide-resistant AHAS activity.

The present invention provides expression cassettes for expressing the polynucleotides of the invention in plants, plant cells, and other non-human host cells. The expression cassettes comprise a promoter expressible in the plant, plant cell, or other host cells of interest operably linked to a polynucleotide of the invention that encodes a herbicide-resistant AHASL1 protein. If necessary for targeting expression to the chloroplast, the expression cassette can also comprise an operably linked chloroplast-targeting sequence that encodes of a chloroplast transit peptide to direct an expressed AHASL1 protein to the chloroplast. The expression cassettes of the invention find use in a method for enhancing the herbicide tolerance of a plant and a host cell. The method involves transforming the plant or host cell with an expression cassette of the invention, wherein the expression cassette comprises a promoter that is expressible in the plant or host cell of interest and the promoter is operably linked to a polynucleotide of the invention that encodes an herbicide-resistant AHASL1 protein of the invention. The method further comprises regenerating a transformed plant from the transformed plant cell.

The present invention provides a method for increasing AHAS activity in a plant comprising transforming a plant cell with a polynucleotide construct comprising a nucleotide sequence operably linked to a promoter that drives expression in a plant cell and regenerating a transformed plant from the transformed plant cell. The nucleotide sequence is selected from those nucleotide sequences that encode the herbicide-resistant AHASL1 proteins of the invention, particularly the nucleotide sequences set forth in SEQ ID NOS: 1 and 3, nucleotide sequences encoding the amino acid sequence set forth in SEQ ID NO: 2, and fragments and variants thereof. A plant produced by this method comprises increased AHAS activity, when compared to an untransformed plant.

The present invention provides a method for producing a herbicide-resistant plant comprising transforming a plant cell with a polynucleotide construct comprising a nucleotide sequence operably linked to a promoter that drives expression in a plant cell and regenerating a transformed plant from said transformed plant cell. The nucleotide sequence is selected from those nucleotide sequences that encode the herbicide-resistant AHASL1 proteins of the invention, particularly the nucleotide sequences set forth in SEQ ID NOS: 1 and 3, nucleotide sequences encoding the amino acid sequence set forth in SEQ ID NO: 2, and fragments and variants thereof, including, but not limited to, the mature forms of the herbicide-resistant AHASL1 proteins of the invention. A herbicide-resistant plant produced by this method comprises enhanced resistance to at least one herbicide, particularly an imidazolinone or sulfonylurea herbicide, when compared to an untransformed plant.

The present invention provides a method for enhancing herbicide-tolerance in a herbicide-tolerant plant. The method finds use in enhancing the resistance of a plant that already is resistant to a level of a herbicide that would kill or significantly injure a wild-type plant. Such a herbicide-tolerant plant can be a herbicide-tolerant plant that has been genetically engineered for herbicide-tolerance or a herbicide-tolerant plant that was developed by means that do not involve recombinant DNA such as, for example, the IMI-NTA 16 rice plants of the present invention. The method comprises transforming a herbicide-tolerant plant with a polynucleotide construct comprising a nucleotide sequence operably linked to a promoter that drives expression in a plant cell and regenerating a transformed plant from the transformed plant cell. The nucleotide sequence is selected from those nucleotide sequences that encode the herbicide-resistant AHASL1 proteins of the invention, particularly the nucleotide sequences set forth in SEQ ID NO: 1 and 3, nucleotide sequences encoding the amino acid sequence set forth in SEQ ID NO: 2, and fragments and variants thereof.

The present invention provides transformation vectors comprising a selectable marker gene of the invention. The selectable marker gene comprises a promoter that drives expression in a host cell operably linked to a polynucleotide comprising a nucleotide sequence that encodes a herbicide-resistant AHASL1 protein of the invention. The transformation vector can additionally comprise a gene of interest to be expressed in the host cell and can also, if desired, include a chloroplast-targeting sequence that is operably linked to the polynucleotide of the invention.

The present invention further provides methods for using the transformation vectors of the invention to select for cells transformed with the gene of interest. Such methods involve the transformation of a host cell with the transformation vector, exposing the cell to a level of an imidazolinone or sulfonylurea herbicide that would kill or inhibit the growth of a non-transformed host cell, and identifying the transformed host cell by its ability to grow in the presence of the herbicide. In one embodiment of the invention, the host cell is a plant cell and the selectable marker gene comprises a promoter that drives expression in a plant cell.

The present invention provides a method for controlling weeds in the vicinity of the herbicide-resistant plants of the invention, including the herbicide-resistant rice plants described above and plants transformed with the herbicide-resistant AHASL1 polynucleotides of the invention. Such transformed plants comprise in their genomes at least one expression cassette comprising a promoter that drives gene expression in a plant cell, wherein the promoter is operably linked to an AHASL1 polynucleotide of the invention. The method comprises applying an effective amount of a herbicide to the weeds and to the herbicide-resistant plant, wherein the herbicide-resistant plant, plant has increased resistance to at least one herbicide, particularly an imidazolinone or sulfonylurea herbicide, when compared to a wild-type or untransformed plant.

The plants of the present invention can be transgenic or non-transgenic. An example of a non-transgenic rice plant having increased resistance to imidazolinone and/or sulfonylurea herbicides includes a rice plant having NCIMB Accession Number NCIMB 41262, or mutant, recombinant, or a genetically engineered derivative of the plant having NCIMB Accession Number NCIMB 41262; or of any progeny of the plant having NCIMB Accession Number NCIMB 41262; or a plant that is a progeny of any of these plants; or a plant that comprises the herbicide resistance characteristics of the plant having NCIMB Accession Number NCIMB 41262.

The present invention also provides plants, plant organs, plant tissues, plant cells, seeds, and non-human host cells that are transformed with the at least one polynucleotide, expression cassette, or transformation vector of the invention. Such transformed plants, plant organs, plant tissues, plant cells, seeds, and non-human host cells have enhanced tolerance or resistance to at least one herbicide, at levels of the herbicide that kill or inhibit the growth of an untransformed plant, plant tissue, plant cell, or non-human host cell, respectively. Preferably, the transformed plants, plant tissues, plant cells, and seeds of the invention are *Arabidopsis thaliana* and crop plants.

BRIEF DESCRIPTION OF THE DRAWING(S)

FIG. 1 is a nucleotide sequence alignment of the herbicide-resistant rice AHASL1 gene of the present invention (SEQ ID NO: 1) with some known plant AHASL nucleotide sequences. The C-to-T transition (relative to wild-type) at nucleotide 542 in SEQ ID NO: 1 is indicated by white type within a black box. The start and stop codons are represented in bold-face type. The names of the other AHASL sequences in the figure are defined as follows: "OsAHASL1.1" is a wild-type AHASL1 nucleotide sequence from El Paso rice background; "OsAHASL1.2" is a wild-type AHASL1 nucleotide sequence from IRGA rice background; "OsAHASL1.4" is a rice AHASL1 nucleotide sequence (Accession No. AB049822); "OsAHASL1.6" is a rice AHASL1 nucleotide sequence (Accession No. AB049823); "ZmAHASL1" is a corn AHASL1 nucleotide sequence (Accession No. X63554); "ZmAHASL2" is a corn AHASL2 nucleotide sequence (Accession No. X63553); "OsAHASL2" is a rice AHASL2 nucleotide sequence (Accession No. AL731599); "AtAHASL" is an *Arabidopsis thaliana* AHASL nucleotide sequence (Accession No. AY124092).

FIG. 2 is an amino acid sequence alignment of the herbicide-resistant rice AHASL1 protein of the present invention (SEQ ID NO: 2) with some known plant AHASL nucleotide sequences. The Ala-to-Val substitution (relative to wild-type) at position 179 in SEQ ID NO: 2 is indicated by white type within a black box. The initial methionine (M) is represented in bold-face type. The other names used in the figure refer to the amino acid sequences encoded by the nucleotide sequences indicated in the description of FIG. 1 above.

SEQUENCE LISTING

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleic acid sequence is shown, but the complementary strand is understood to be included by any reference to the displayed strand. The amino acid sequences follow the standard convention of beginning at the amino terminus of the sequence and proceeding forward (i.e., from left to right in each line) to the carboxyl terminus.

SEQ ID NO: 1 sets forth the nucleotide sequence encoding an imidazolinone-resistant AHASL1 protein from rice with the Ala$_{179}$-to-Val substitution. The coding region of SEQ ID NO: 1 corresponds to nucleotides 7 to 1938.

SEQ ID NO: 2 sets forth the amino acid sequence of an imidazolinone-resistant AHASL1 protein from rice with the Ala$_{179}$-to-Val substitution that is encoded by the nucleotide sequence set forth in SEQ ID NO: 1.

SEQ ID NO: 3 sets forth the nucleotide sequence of the coding region of SEQ ID NO: 1.

SEQ ID NOS: 4-18 set forth the nucleotide sequences of primers used for the PCR amplification and DNA sequencing of the AHASL1 gene of the invention as described in Example 2 below (see, Table 1).

DETAILED DESCRIPTION OF THE INVENTION

The present invention relates to rice plants having increased resistance to herbicides when compared to a wild-type rice plant. The herbicide resistant rice plants of the invention were produced as described hereinbelow by exposing wild-type (with respect to herbicide resistance) rice seeds to a mutagen, sowing the seeds, allowing the plants to mature and reproduce, and selecting progeny plants that displayed enhanced resistance to imidazolinone herbicides, relative to the resistance of a wild-type rice plant. The invention provides the herbicide resistant rice line and plants thereof that are referred to herein IMINTA 16. Such herbicide resistant rice plants find use in methods for controlling weeds, particularly red rice and other weeds that are sensitive to imidazolinone and sulfonylurea herbicides.

From the IMINTA 16 herbicide-resistant rice plants, the coding region of an acetohydroxyacid synthase large subunit 1 (AHASL1) gene was isolated by polymerase chain reaction (PCR) amplification and sequenced. By comparing the polynucleotide sequences of the herbicide resistant rice plants of the invention to a rice AHASL1 cDNA from a wild-type rice plant (GenBank Accession No. AB049822), it was discovered that the coding region of the AHASL1 polynucleotide sequence from IMINTA 16 differed from the wild-type rice AHASL1 cDNA sequence by a single nucleotide. For the AHASL1 polynucleotide sequence of IMINTA 16, there was a C-to-T transition at nucleotide 542 (SEQ ID NO: 1, FIG. 1). This C-to-T transition in the AHASL1 polynucleotide sequence results in a Ala-to-Val substitution at amino acid 179 in a conserved region of the predicted amino acid sequence of the AHASL1 protein, relative to the amino acid sequence of the wild-type AHASL1 protein (FIG. 2).

The invention further relates to isolated polynucleotide molecules comprising nucleotide sequences that encode the herbicide-resistant AHASL1 proteins of IMINTA 16 rice plants and to such AHASL1 proteins. The invention discloses the isolation and nucleotide sequence of a polynucleotide encoding a herbicide-resistant rice AHASL1 protein from herbicide-resistant rice plant that was produced by chemical mutagenesis of wild-type rice plants. The herbicide-resistant AHASL1 proteins of the invention comprise an alanine-to-valine substitution at position 179 in their respective amino acid sequences, when compared to the corresponding wild-type AHASL1 amino acid sequence.

The present invention provides isolated polynucleotide molecules that encode herbicide resistant AHASL1 proteins from rice (*Oryza sativa* L.). Specifically, the invention provides isolated polynucleotide molecules comprising: the nucleotide sequences set forth in SEQ ID NOS: 1 and 3, nucleotide sequences encoding AHASL1 proteins comprising the amino acid sequence set forth in SEQ ID NO: 2, and fragments and variants of such nucleotide sequences that encode functional AHASL1 proteins that comprise herbicide-resistant AHAS activity.

The isolated herbicide-resistant AHASL1 polynucleotide molecules of the invention comprise nucleotide sequences that encode herbicide-resistant AHASL1 proteins. Such polynucleotide molecules can be used in polynucleotide constructs for the transformation of plants, particularly crop plants, to enhance the resistance of the plants to herbicides, particularly herbicides that are known to inhibit AHAS activity, more particularly imidazolinone and sulfonylurea herbicides. Such polynucleotide constructs can be used in expression cassettes, expression vectors, transformation vectors, plasmids and the like. The transgenic plants obtained following transformation with such polynucleotide constructs show increased resistance to AHAS-inhibiting herbicides such as, for example, imidazolinone and sulfonylurea herbicides.

Compositions of the invention include polynucleotide molecules comprising nucleotide sequences that encode AHASL1 proteins. In particular, the present invention provides for isolated polynucleotide molecules comprising nucleotide sequences encoding the amino acid sequence shown in SEQ ID NO: 2, and fragments and variants thereof that encode polypeptides comprising AHAS activity. Further provided are polypeptides having an amino acid sequence encoded by a polynucleotide molecule described herein, for example those set forth in SEQ ID NOS: 1 and 3, and fragments and variants thereof that encode polypeptides comprising AHAS activity, particularly herbicide-resistant AHASL activity. The polynucleotides molecules of the invention further encompass nucleotide sequences that encode mature forms of the AHASL1 proteins described above. Such mature forms of AHASL1 proteins comprise AHAS activity, particularly herbicide-resistant AHAS activity, but lack the chloroplast transit peptide that is part of full-length AHASL1 proteins.

The invention encompasses isolated or substantially purified nucleic acid or protein compositions. An "isolated" or "purified" polynucleotide molecule or protein, or biologically active portion thereof, is substantially or essentially free from components that normally accompany or interact with the polynucleotide molecule or protein as found in its naturally occurring environment. Thus, an isolated or purified polynucleotide molecule or protein is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated polynucleotide molecule can contain less than about 5 kb, 4 kb, 3 kb, 2 kb, 1 kb, 0.5 kb, or 0.1 kb of nucleotide sequences that naturally flank the polynucleotide molecule in genomic DNA of the cell from which the nucleic acid is derived. A protein that is substantially free of cellular material includes preparations of protein having less than about 30%, 20%, 10%, 5%, or 1% (by dry weight) of contaminating protein. When the protein of the invention or biologically active portion thereof is recombinantly produced, preferably culture medium represents less than about 30%, 20%, 10%, 5%, or 1% (by dry weight) of chemical precursors or non-protein-of-interest chemicals.

The present invention provides isolated polypeptides comprising AHASL1 proteins. The isolated polypeptides comprise an amino acid sequence selected from the group consisting of the amino acid sequence set forth in SEQ ID NO: 2, the amino acid sequences encoded by nucleotide sequences set forth in SEQ ID NOS: 1 and 3, and functional fragments and variants of said amino acid sequences that encode an AHASL1 polypeptide comprising AHAS activity.

By "functional fragments and variants" is intended fragments and variants of the exemplified polypeptides that comprise AHAS activity.

Additionally provided are isolated polypeptides comprising the mature forms of the AHASL1 proteins of the invention. Such mature forms of AHASL1 proteins comprise AHAS activity, particularly herbicide-resistant AHAS activity, but lack the chloroplast transit peptide that is part of full-length AHASL1 proteins.

In certain embodiments of the invention, the methods involve the use of herbicide-tolerant or herbicide-resistant plants. By an "herbicide-tolerant" or "herbicide-resistant" plant, it is intended that a plant that is tolerant or resistant to at least one herbicide at a level that would normally kill, or inhibit the growth of, a normal or wild-type plant. In one embodiment of the invention, the herbicide-tolerant plants of the invention comprise a herbicide-tolerant or herbicide-resistant AHASL1 protein. By "herbicide-tolerant AHASL1 protein" or "herbicide-resistant AHASL1 protein", it is intended that such an AHASL1 protein displays higher AHAS activity, relative to the AHAS activity of a wild-type AHASL1 protein, when in the presence of at least one herbicide that is known to interfere with AHAS activity and at a concentration or level of the herbicide that is to known to inhibit the AHAS activity of the wild-type AHASL1 protein. Furthermore, the AHAS activity of such a herbicide-tolerant or herbicide-resistant AHASL1 protein may be referred to herein as "herbicide-tolerant" or "herbicide-resistant" AHAS activity.

For the present invention, the terms "herbicide-tolerant" and "herbicide-resistant" are used interchangeable and are intended to have an equivalent meaning and an equivalent scope. Similarly, the terms "herbicide-tolerance" and "herbicide-resistance" are used interchangeable and are intended to have an equivalent meaning and an equivalent scope. Likewise, the terms "imidazolinone-resistant" and "imidazolinone-resistance" are used interchangeable and are intended to be of an equivalent meaning and an equivalent scope as the terms "imidazolinone-tolerant" and "imidazolinone-tolerance", respectively.

The invention encompasses herbicide-resistant AHASL1 polynucleotides and herbicide-resistant AHASL1 proteins. By "herbicide-resistant AHASL1 polynucleotide" is intended a polynucleotide that encodes a protein comprising herbicide-resistant AHAS activity. By "herbicide-resistant AHASL1 protein" is intended a protein or polypeptide that comprises herbicide-resistant AHAS activity.

Further, it is recognized that a herbicide-tolerant or herbicide-resistant AHASL1 protein can be introduced into a plant by transforming a plant or ancestor thereof with a nucleotide sequence encoding a herbicide-tolerant or herbicide-resistant AHASL1 protein. Such herbicide-tolerant or herbicide-resistant AHASL1 proteins are encoded by the herbicide-tolerant or herbicide-resistant AHASL1 polynucleotides. Alternatively, a herbicide-tolerant or herbicide-resistant AHASL1 protein may occur in a plant as a result of a naturally occurring or induced mutation in an endogenous AHASL1 gene in the genome of a plant or progenitor thereof.

The present invention provides plants, plant tissues, plant cells, and host cells with increased resistance or tolerance to at least one herbicide, particularly an imidazolinone or sulfonylurea herbicide. The preferred amount or concentration of the herbicide is an "effective amount" or "effective concentration." By "effective amount" and "effective concentration" is intended an amount and concentration, respectively, that is sufficient to kill or inhibit the growth of a similar, wild-type, plant, plant tissue, plant cell, or host cell, but that said amount does not kill or inhibit as severely the growth of the herbicide-resistant plants, plant tissues, plant cells, and host cells of the present invention. Typically, the effective amount of a herbicide is an amount that is routinely used in agricultural production systems to kill weeds of interest. Such an amount is known to those of ordinary skill in the art.

By "similar, wild-type, plant, plant tissue, plant cell or host cell" is intended a plant, plant tissue, plant cell, or host cell, respectively, that lacks the herbicide-resistance characteristics and/or particular polynucleotide of the invention that are disclosed herein. The use of the term "wild-type" is not, therefore, intended to imply that a plant, plant tissue, plant cell, or other host cell lacks recombinant DNA in its genome, and/or does not possess herbicide resistant characteristics that are different from those disclosed herein.

As used herein unless clearly indicated otherwise, the term "plant" intended to mean a plant any developmental stage, as well as any part or parts of a plant that may be attached to or separate from a whole intact plant. Such parts of a plant include, but are not limited to, organs, tissues, and cells of a plant. Examples of particular plant parts include a stem, a leaf, a root, an inflorescence, a flower, a floret, a fruit, a pedicle, a peduncle, a stamen, an another, a stigma, a style, an ovary, a petal, a sepal, a carpel, a root tip, a root cap, a root hair, a leaf hair, a seed hair, a pollen grain, a microspore, a cotyledon, a hypocotyl, an epicotyl, xylem, phloem, parenchyma, endosperm, a companion cell, a guard cell, and any other known organs, tissues, and cells of a plant. Furthermore, it is recognized that a seed is a plant.

The plants of the present invention include both non-transgenic plants and transgenic plants. By "non-transgenic plant" is intended mean a plant lacking recombinant DNA in its genome. By "transgenic plant" is intended to mean a plant comprising recombinant DNA in its genome. Such a transgenic plant can be produced by introducing recombinant DNA into the genome of the plant. When such recombinant DNA is incorporated into the genome of the transgenic plant, progeny of the plant can also comprise the recombinant DNA. A progeny plant that comprises at least a portion of the recombinant DNA of at least one progenitor transgenic plant is also a transgenic plant.

The present invention provides the herbicide-resistant rice line and plants thereof known as IMINTA 16. A deposit of at least 250 seeds of IMINTA 16 was made to the patent depository of NCIMB Ltd., Ferguson Building, Craibstone Estate Bucksburn, Aberdeen, AB21 9YA, Scotland, UK on Jan. 5, 2005 and assigned NCIMB Accession Number NCIMB 41262. Due to a shortage of seeds of the IMINTA 16 line at the time of filing, less than 2500 seeds of the IMINTA 16 line were submitted to NCIMB Ltd. prior to filing. Applicants will supply additional seeds of the IMINTA 16 line to reach a total of at least 2500 seeds as the seeds become available. These deposits will be maintained under the terms of the Budapest Treaty on the International Recognition of the Deposit of Microorganisms for the Purposes of Patent Procedure. The deposit of the seeds of IMINTA 16 was made for a term of at least 30 years and at least 5 years after the most recent request for the furnishing of a sample of that deposit is received by NCIMB Ltd. Additionally, Applicants have satisfied all the requirements of 37 C.F.R. §§ 1.801-1.809, including providing an indication of the viability of the sample. The deposit will irrevocably and without restriction or condition be available to the public upon issuance of a patent. However, it should be understood that the availability of the deposit does not constitute a license to practice the subject invention.

The present invention provides herbicide-resistant rice plants of the IMINTA 16 line that were produced by a mutation breeding. Wild-type rice plants were mutagenized by exposing the plants to a mutagen, particularly a chemical mutagen, more particularly sodium azide. However, the present invention is not limited to herbicide-resistant rice plants that are produced by a mutagenesis method involving the chemical mutagen sodium azide. Any mutagenesis method known in the art may be used to produce the herbicide-resistant rice plants of the present invention. Such mutagenesis methods can involve, for example, the use of any one or more of the following mutagens: radiation, such as X-rays, Gamma rays (e.g., cobalt 60 or cesium 137), neutrons, (e.g., product of nuclear fission by uranium 235 in an atomic reactor), Beta radiation (e.g., emitted from radio-isotopes such as phosphorus 32 or carbon 14), and ultraviolet radiation (preferably from 2500 to 2900 nm), and chemical mutagens such as base analogues (e.g., 5-bromo-uracil), related compounds (e.g., 8-ethoxy caffeine), antibiotics (e.g., streptonigrin), alkylating agents (e.g., sulfur mustards, nitrogen mustards, epoxides, ethylenamines, sulfates, sulfonates, sulfones, lactones), azide, hydroxylamine, nitrous acid, ethyl methanesulfonate (EMS), or acridines. Herbicide-resistant plants can also be produced by using tissue culture methods to select for plant cells comprising herbicide-resistance mutations and then regenerating herbicide-resistant plants therefrom. See, for example, U.S. Pat. Nos. 5,773,702 and 5,859,348, both of which are herein incorporated in their entirety by reference. Further details of mutation breeding can be found in "Principals of Cultivar Development" Fehr, 1993 Macmillan Publishing Company the disclosure of which is incorporated herein by reference.

Analysis of the AHASL1 gene of the rice plants of IMINTA 16 line revealed a point mutation. In the AHASL1 gene from IMINTA 16, the point mutation results in the substitution of a valine for the alanine that is found at amino acid position 179 in the wild-type AHASL1 amino acid sequence of GenBank Accession No. AB049822. Thus, the present invention discloses that substituting another amino acid for the alanine at amino acid position 179 of the rice AHASL1 protein can cause a rice plant to have enhanced resistance to a herbicide, particularly an imidazolinone and/or sulfonylurea herbicide. As disclosed in Example 3 below, alanine 179 is found in a conserved region of AHASL proteins and other amino acid substitutions for the alanine at 179 have been disclosed that are known to confer herbicide resistance on a plant that comprises such an AHASL protein. Accordingly, the herbicide-resistant rice plants of the invention include, but are not limited to those rice plants which comprise in their genomes at least one copy of an AHASL1 polynucleotide that encodes a herbicide-resistant AHASL1 protein that comprises an aspartate or valine at amino acid position 179 or equivalent position.

The rice plants of the invention additionally include plants that comprise, relative to the wild-type AHASL1 protein, an aspartate or valine at amino acid position 179 or equivalent position and one or more additional amino acid substitutions in the AHASL1 protein relative to the wild-type AHASL1 protein, wherein such a rice plant has increased resistance to at least one herbicide when compared to a wild-type rice plant. Such additional amino acid substitutions include, but are not limited to: a threonine at amino acid position 96 or equivalent position; an alanine, threonine, histidine, leucine, arginine, isoleucine, glutamine, or serine at amino acid position 171 or equivalent position; a leucine at amino acid position 548 or equivalent position; and an asparagine, threonine, or phenylalanine at amino acid position 627 or equivalent position.

The present invention provides AHASL1 proteins with amino acid substitutions at particular amino acid positions within conserved regions of the rice AHASL1 proteins disclosed herein. Unless otherwise indicated herein, particular amino acid positions refer to the position of that amino acid in the full-length rice AHASL1 amino acid sequences set forth in SEQ ID NO: 2. Furthermore, those of ordinary skill in the art will recognize that such amino acid positions can vary depending on whether amino acids are added or removed from, for example, the N-terminal end of an amino acid sequence. Thus, the invention encompasses the amino substitutions at the recited position or equivalent position (e.g., "amino acid position 179 or equivalent position"). By "equivalent position" is intended to mean a position that is within the same conserved region as the exemplified amino acid position. Examples of such conserved regions are provided in Table 2 below.

In addition, the present invention provides rice AHASL1 polypeptides comprising an aspartate or valine at amino acid position 179 or equivalent position and one or more additional amino acid substitutions in the AHASL1 protein, relative to the wild-type AHASL1 protein, wherein AHASL1 polypeptide comprises herbicide tolerant AHAS activity, when compared to the AHAS activity of a wild-type AHASL1. These amino acid substitutions include, but are not limited, to those that are known to confer resistance on a plant to at least one herbicide, particularly an imidazolinone herbicide and/or a sulfonylurea herbicide. Such additional amino acid substitutions include, but are not limited to: a threonine at amino acid position 96 or equivalent position; an alanine, threonine, histidine, leucine, arginine, isoleucine, glutamine, or serine at amino acid position 171 or equivalent position; a leucine at amino acid position 548 or equivalent position; and an asparagine, threonine, or phenylalanine at amino acid position 627 or equivalent position. The invention further provides isolated polynucleotides encoding such AHASL1 polypeptides, as well as expression cassettes, transformation vectors, transformed host cells, transformed plants, and methods comprising such polynucleotides.

The present invention provides methods for enhancing the tolerance or resistance of a plant, plant tissue, plant cell, or other host cell to at least one herbicide that interferes with the activity of the AHAS enzyme. Preferably, such an AHAS-inhibiting herbicide is an imidazolinone herbicide, a sulfonylurea herbicide, a triazolopyrimidine herbicide, a pyrimidinyloxybenzoate herbicide, a sulfonylamino-carbonyltriazolinone herbicide, or mixture thereof. More preferably, such a herbicide is an imidazolinone herbicide, a sulfonylurea herbicide, or mixture thereof. For the present invention, the imidazolinone herbicides include, but are not limited to, PURSUIT® (imazethapyr), CADRE® (imazapic), RAPTOR® (imazamox), SCEPTER® (imazaquin), ASSERT® (imazethabenz), ARSENAL® (imazapyr), a derivative of any of the aforementioned herbicides, and a mixture of two or more of the aforementioned herbicides, for example, imazapyr/imazamox (ODYSSEY®). More specifically, the imidazolinone herbicide can be selected from, but is not limited to, 2-(4-isopropyl-4-methyl-5-oxo-2-imidiazolin-2-yl)-nicotinic acid, [2-(4-isopropyl)-4-] [methyl-5-oxo-2-imidazolin-2-yl)-3-quinolinecarboxylic] acid, [5-ethyl-2-(4-isopropyl-] 4-methyl-5-oxo-2-imidazolin-2-yl)-nicotinic acid, 2-(4-isopropyl-4-methyl-5-oxo-2-imidazolin-2-yl)-5-(methoxymethyl)-nicotinic acid, [2-(4-isopropyl-4-methyl-5-oxo-2-]imidazolin-2-yl)-5-methylnicotinic acid, and a mixture of methyl [6-(4-isopropyl-4-] methyl-5-oxo-2-imidazolin-2-yl)-m-toluate and methyl [2-(4-isopro-pyl-4-methyl-5-] oxo-2-imidazolin-2-yl)-p-toluate. The use of 5-ethyl-2-(4-isopropyl-4-methyl-5-oxo-2-imidazolin-2-yl)-nicotinic acid and [2-(4-isopropyl-4-methyl-5-oxo-2-imidazolin-2-] yl)-5-(methoxymethyl)-nicotinic acid is preferred. The use of [2-(4-isopropyl-4-] methyl-5-oxo-2-imidazolin-2-yl)-5-(methoxymethyl)-nicotinic acid is particularly preferred.

For the present invention, the sulfonylurea herbicides include, but are not limited to, chlorsulfuron, metsulfuron methyl, sulfometuron methyl, chlorimuron ethyl, thifensulfuron methyl, tribenuron methyl, bensulfuron methyl, nicosulfuron, ethametsulfuron methyl, rimsulfuron, triflusulfuron methyl, triasulfuron, primisulfuron methyl, cinosulfuron, amidosulfiuon, flazasulfuron, imazosulfuron, pyrazosulfuron ethyl, halosulfuron, azimsulfuron, cyclosulfuron, ethoxysulfuron, flazasulfuron, flupyrsulfuron methyl, foramsulfuron, iodosulfuron, oxasulfuron, mesosulfuron, prosulfuron, sulfosulfuron, trifloxysulfuron, tritosulfuron, a derivative of any of the aforementioned herbicides, and a mixture of two or more of the aforementioned herbicides. The triazolopyrimidine herbicides of the invention include, but are not limited to, cloransulam, diclosulam, florasulam, flumetsulam, metosulam, and penoxsulam. The pyrimidinyloxybenzoate herbicides of the invention include, but are not limited to, bispyribac, pyrithiobac, pyriminobac, pyribenzoxim and pyriftalid. The sulfonylamino-carbonyltriazolinone herbicides include, but are not limited to, flucarbazone and propoxycarbazone.

It is recognized that pyrimidinyloxybenzoate herbicides are closely related to the pyrimidinylthiobenzoate herbicides and are generalized under the heading of the latter name by the Weed Science Society of America. Accordingly, the herbicides of the present invention further include pyrimidinylthiobenzoate herbicides, including, but not limited to, the pyrimidinyloxybenzoate herbicides described above.

The present invention provides methods for enhancing AHAS activity in a plant comprising transforming a plant with a polynucleotide construct comprising a promoter operably linked to an AHASL1 nucleotide sequence of the invention. The methods involve introducing a polynucleotide construct of the invention into at least one plant cell and regenerating a transformed plant therefrom. The methods involve the use of a promoter that is capable of driving gene expression in a plant cell. Preferably, such a promoter is a constitutive promoter or a tissue-preferred promoter. The methods find use in enhancing or increasing the resistance of a plant to at least one herbicide that interferes with the catalytic activity of the AHAS enzyme, particularly an imidazolinone or sulfonylurea herbicide.

The present invention provides expression cassettes for expressing the polynucleotides of the invention in plants, plant tissues, plant cells, and other host cells. The expression cassettes comprise a promoter expressible in the plant, plant tissue, plant cell, or other host cells of interest operably linked to a polynucleotide of the invention that comprises a nucleotide sequence encoding either a full-length (i.e. including the chloroplast transit peptide) or mature AHASL1 protein (i.e. without the chloroplast transit peptide). If expression is desired in the plastids or chloroplasts of plants or plant cells, the expression cassette may also comprise an operably linked chloroplast-targeting sequence that encodes a chloroplast transit peptide.

The expression cassettes of the invention find use in a method for enhancing the herbicide tolerance of a plant or a host cell. The method involves transforming the plant or host cell with an expression cassette of the invention, wherein the expression cassette comprises a promoter that is expressible in the plant or host cell of interest and the promoter is operably linked to a polynucleotide of the invention that comprises a nucleotide sequence encoding an imidazolinone-resistant AHASL1 protein of the invention.

The use of the term "polynucleotide constructs" herein is not intended to limit the present invention to polynucleotide constructs comprising DNA. Those of ordinary skill in the art will recognize that polynucleotide constructs, particularly polynucleotides and oligonucleotides, comprised of ribonucleotides and combinations of ribonucleotides and deoxyribonucleotides may also be employed in the methods disclosed herein. Thus, the polynucleotide constructs of the present invention encompass all polynucleotide constructs that can be employed in the methods of the present invention for transforming plants including, but not limited to, those comprised of deoxyribonucleotides, ribonucleotides, and combinations thereof. Such deoxyribonucleotides and ribonucleotides include both naturally occurring molecules and synthetic analogues. The polynucleotide constructs of the invention also encompass all forms of polynucleotide constructs including, but not limited to, single-stranded forms, double-stranded forms, hairpins, stem-and-loop structures, and the like. Furthermore, it is understood by those of ordinary skill the art that each nucleotide sequences disclosed herein also encompasses the complement of that exemplified nucleotide sequence.

Furthermore, it is recognized that the methods of the invention may employ a polynucleotide construct that is capable of directing, in a transformed plant, the expression of at least one protein, or at least one RNA, such as, for example, an antisense RNA that is complementary to at least a portion of an mRNA. Typically such a polynucleotide construct is comprised of a coding sequence for a protein or RNA operably linked to 5' and 3' transcriptional regulatory regions. Alternatively, it is also recognized that the methods of the invention may employ a polynucleotide construct that is not capable of directing, in a transformed plant, the expression of a protein or RNA.

Further, it is recognized that, for expression of a polynucleotides of the invention in a host cell of interest, the polynucleotide is typically operably linked to a promoter that is capable of driving gene expression in the host cell of interest. The methods of the invention for expressing the polynucleotides in host cells do not depend on particular promoter. The methods encompass the use of any promoter that is known in the art and that is capable of driving gene expression in the host cell of interest.

The present invention encompasses AHASL1 polynucleotide molecules and fragments and variants thereof. Polynucleotide molecules that are fragments of these nucleotide sequences are also encompassed by the present invention. By "fragment" is intended a portion of the nucleotide sequence encoding an AHASL1 protein of the invention. A fragment of an AHASL1 nucleotide sequence of the invention may encode a biologically active portion of an AHASL1 protein, or it may be a fragment that can be used as a hybridization probe or PCR primer using methods disclosed below. A biologically active portion of an AHASL1 protein can be prepared by isolating a portion of one of the AHASL1 nucleotide sequences of the invention, expressing the encoded portion of the AHASL1 protein (e.g., by recombinant expression in vitro), and assessing the activity of the encoded portion of the AHASL1 protein. Polynucleotide molecules that are fragments of an AHASL1 nucleotide sequence comprise at least about 15, 20, 50, 75, 100, 200, 300, 350, 400, 450, 500, 550, 600, 650, 700, 750, 800, 850, 900, 950, 1000, 1050, 1100, 1150, 1200, 1250, 1300, 1350, 1400, 1500, 1600, 1700, 1800, 1900, or 1950 nucleotides, or up to the number of nucleotides present in a full-length nucleotide sequence disclosed herein (for example, 1961 and 1932 nucleotides for SEQ ID NOS: 1 and 3, respectively) depending upon the intended use.

A fragment of an AHASL1 nucleotide sequence that encodes a biologically active portion of an AHASL1 protein of the invention will encode at least about 15, 25, 30, 50, 75, 100, 125, 150, 175, 200, 250, 300, 350, 400, 450, 500, 550, 600, or 625 contiguous amino acids, or up to the total number of amino acids present in a full-length AHASL1 protein of the invention (for example, 644 amino acids for SEQ ID NO: 2). Fragments of an AHASL1 nucleotide sequence that are useful as hybridization probes for PCR primers generally need not encode a biologically active portion of an AHASL1 protein.

Polynucleotide molecules that are variants of the nucleotide sequences disclosed herein are also encompassed by the present invention. "Variants" of the AHASL1 nucleotide sequences of the invention include those sequences that encode the AHASL1 proteins disclosed herein but that differ conservatively because of the degeneracy of the genetic code. These naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the AHASL1 protein disclosed in the present invention as discussed below. Generally, nucleotide sequence variants of the invention will have at least about 90%, 91%, 92%, 93%, 94%, 95%, 96%, 97%, 98%, or 99% identity to a particular nucleotide sequence disclosed herein. A variant AHASL1 nucleotide sequence will encode an AHASL1 protein, respectively, that has an amino acid sequence having at least about 90%, 91%, 92%, 93%, 94%, 95%, 96%, 97%, 98%, or 99% identity to the amino acid sequence of an AHASL1 protein disclosed herein.

In addition, the skilled artisan will further appreciate that changes can be introduced by mutation into the nucleotide sequences of the invention thereby leading to changes in the amino acid sequence of the encoded AHASL1 proteins without altering the biological activity of the AHASL1 proteins. Thus, an isolated polynucleotide molecule encoding an AHASL1 protein having a sequence that differs from that of SEQ ID NOS: 1 or 3, respectively, can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, preferably, conservative amino acid substitutions may be made at one or more predicted, preferably nonessential amino acid residues. A "nonessential" amino acid residue is a residue that can be altered from the wild-type sequence of an AHASL1 protein (e.g., the sequence of SEQ ID NO: 2) without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Such substitutions would not be made for conserved amino acid residues, or for amino acid residues residing within a conserved motif.

The proteins of the invention may be altered in various ways including amino acid substitutions, deletions, truncations, and insertions. Methods for such manipulations are generally known in the art. For example, amino acid sequence variants of the AHASL1 proteins can be prepared by mutations in the DNA. Methods for mutagenesis and nucleotide sequence alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferable.

Alternatively, variant AHASL1 nucleotide sequences can be made by introducing mutations randomly along all or part of an AHASL1 coding sequence, such as by saturation mutagenesis, and the resultant mutants can be screened for AHAS activity to identify mutants that retain AHAS activity, including herbicide-resistant AHAS activity. Following mutagenesis, the encoded protein can be expressed recombinantly, and the activity of the protein can be determined using standard assay techniques.

Thus, the nucleotide sequences of the invention include the sequences disclosed herein as well as fragments and variants thereof. The AHASL1 nucleotide sequences of the invention, and fragments and variants thereof, can be used as probes and/or primers to identify and/or clone AHASL homologues in other plants. Such probes can be used to detect transcripts or genomic sequences encoding the same or identical proteins.

In this manner, methods such as PCR, hybridization, and the like can be used to identify such sequences having substantial identity to the sequences of the invention. See, for example, Sambrook et al. (1989) *Molecular Cloning: Laboratory Manual* (2d ed., Cold Spring Harbor Laboratory Press, Plainview, NY) and Innis, et al. (1990) *PCR Protocols: A Guide to Methods and Applications* (Academic Press, NY). AHASL nucleotide sequences isolated based on their sequence identity to the AHASL1 nucleotide sequences set forth herein or to fragments and variants thereof are encompassed by the present invention.

In a hybridization method, all or part of a known AHASL1 nucleotide sequence can be used to screen cDNA or genomic libraries. Methods for construction of such cDNA and genomic libraries are generally known in the art and are disclosed in Sambrook et al. (1989) *Molecular Cloning: A Laboratory Manual* (2d ed., Cold Spring Harbor Laboratory Press, Plainview, NY). The so-called hybridization probes may be genomic DNA fragments, cDNA fragments, RNA fragments, or other oligonucleotides, and may be labeled with a detectable group such as $^{32}$P, or any other detectable marker, such as other radioisotopes, a fluorescent compound, an enzyme, or an enzyme co-factor. Probes for hybridization can be made by labeling synthetic oligonucleotides based on the known AHASL1 nucleotide sequence disclosed herein. Degenerate primers designed on the basis of conserved nucleotides or amino acid residues in a known AHASL1 nucleotide sequence or encoded amino acid sequence can additionally be used. The probe typically comprises a region of nucleotide sequence that hybridizes under stringent conditions to at least about 12, preferably about 25, more preferably about 50, 75, 100, 125, 150, 175, 200, 250, 300, 350, 400, 500, 600, 700, 800, 900, 1000, 1200, 1400, 1600, or 1800 consecutive nucleotides of an AHASL1 nucleotide sequence of the invention or a fragment or variant thereof. Preparation of Probes for Hybridization is Generally Known in the Art and is Disclosed in Sambrook et al. (1989) *Molecular Cloning: A Laboratory Manual* (2d ed., Cold Spring Harbor Laboratory Press, Plainview, New York), herein incorporated by reference.

For example, the entire AHASL1 sequence disclosed herein, or one or more portions thereof, may be used as a probe capable of specifically hybridizing to corresponding AHASL1 sequences and messenger RNAs. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, New York).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. The duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m = 81.5°$ C.$+16.6$ (log M)$+0.41$ (% GC)$-0.61$ (% form)–

500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, New York).

It is recognized that the polynucleotide molecules and proteins of the invention encompass polynucleotide molecules and proteins comprising a nucleotide or an amino acid sequence that is sufficiently identical to the nucleotide sequence of SEQ ID NOS: 1, 3, 4, and/or 6, or to the amino acid sequence of SEQ ID NOS: 2 and/or 5. The term "sufficiently identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain and/or common functional activity. For example, amino acid or nucleotide sequences that contain a common structural domain having at least about 45%, 55%, or 65% identity, preferably 75% identity, more preferably 85%, 95%, or 98% identity are defined herein as sufficiently identical.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A preferred, nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the NBLAST and XBLAST programs of Altschul et al. (1990) *J. Mol. Biol.* 215:403. BLAST nucleotide searches can be performed with the NBLAST program, score=100, wordlength=12, to obtain nucleotide sequences homologous to the polynucleotide molecules of the invention. BLAST protein searches can be performed with the XBLAST program, score=50, wordlength=3, to obtain amino acid sequences homologous to protein molecules of the invention. To obtain gapped alignments for comparison purposes, Gapped BLAST can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used. Alignment may also be performed manually by inspection.

Unless otherwise stated, sequence identity/similarity values provided herein refer to the value obtained using the full-length sequences of the invention and using multiple alignment by mean of the algorithm Clustal W (Nucleic Acid Research, 22(22):4673-4680, 1994) using the program AlignX included in the software package Vector NTI Suite Version 7 (InforMax, Inc., Bethesda, MD, USA) using the default parameters; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by AlignX in the software package Vector NTI Suite Version 7.

The AHASL1 nucleotide sequences of the invention include both the naturally occurring sequences as well as mutant forms, particularly mutant forms that encode AHASL1 proteins comprising herbicide-resistant AHAS activity. Likewise, the proteins of the invention encompass both naturally occurring proteins as well as variations and modified forms thereof. Such variants will continue to possess the desired AHAS activity. Obviously, the mutations that will be made in the DNA encoding the variant must not place the sequence out of reading frame and preferably will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by AHAS activity assays. See, for example, Singh et al. (1988) *Anal. Biochem.* 171:173-179, herein incorporated by reference.

Variant nucleotide sequences and proteins also encompass sequences and proteins derived from a mutagenic and recombinogenic procedure such as DNA shuffling. With such a procedure, one or more different AHASL coding sequences can be manipulated to create a new AHASL protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the AHASL1 gene of the invention and other known AHASL genes to obtain a new gene coding for a protein with an improved property of interest, such as an increased $K_m$ in the case of an enzyme. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The nucleotide sequences of the invention can be used to isolate corresponding sequences from other organisms, particularly other plants, more particularly other dicots. In this manner, methods such as PCR, hybridization, and the like can be used to identify such sequences based on their sequence homology to the sequences set forth herein. Sequences isolated based on their sequence identity to the entire AHASL1 sequences set forth herein or to fragments thereof are encompassed by the present invention. Thus, isolated sequences that encode for an AHASL protein and which hybridize under stringent conditions to the sequence disclosed herein, or to fragments thereof, are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, New York). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

The AHASL1 polynucleotide sequences of the invention are provided in expression cassettes for expression in the plant of interest. The cassette will include 5' and 3' regulatory sequences operably linked to an AHASL1 polynucleotide sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

Such an expression cassette is provided with a plurality of restriction sites for insertion of the AHASL1 polynucleotide sequence to be under the transcriptional regulation of the regulatory regions. The expression cassette may additionally contain selectable marker genes.

The expression cassette will include in the 5'-3' direction of transcription, a transcriptional and translational initiation region (i.e., a promoter), an AHASL1 polynucleotide sequence of the invention, and a transcriptional and translational termination region (i.e., termination region) functional in plants. The promoter may be native or analogous, or foreign or heterologous, to the plant host and/or to the AHASL1 polynucleotide sequence of the invention. Additionally, the promoter may be the natural sequence or alternatively a synthetic sequence. Where the promoter is "foreign" or "heterologous" to the plant host, it is intended that the promoter is not found in the native plant into which the promoter is introduced. Where the promoter is "foreign" or "heterologous" to the AHASL1 polynucleotide sequence of the invention, it is intended that the promoter is not the native or naturally occurring promoter for the operably linked AHASL1 polynucleotide sequence of the invention. As used herein, a chimeric gene comprises a coding sequence operably linked to a transcription initiation region that is heterologous to the coding sequence.

While it may be preferable to express the AHASL1 polynucleotides of the invention using heterologous promoters, the native promoter sequences may be used. Such constructs would change expression levels of the AHASL1 protein in the plant or plant cell. Thus, the phenotype of the plant or plant cell is altered.

The termination region may be native with the transcriptional initiation region, may be native with the operably linked AHASL1 sequence of interest, may be native with the plant host, or may be derived from another source (i.e., foreign or heterologous to the promoter, the AHASL1 polynucleotide sequence of interest, the plant host, or any combination thereof). Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed plant. That is, the genes can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

Nucleotide sequences for enhancing gene expression can also be used in the plant expression vectors. These include the introns of the maize AdhI, intron1 gene (Callis et al. *Genes and Development* 1:1183-1200, 1987), and leader sequences, (W-sequence) from the Tobacco Mosaic virus (TMV), Maize Chlorotic Mottle Virus and Alfalfa Mosaic Virus (Gallie et al. *Nucleic Acid Res.* 15:8693-8711, 1987 and Skuzeski et al. *Plant Mol. Biol.* 15:65-79, 1990). The first intron from the shrunken-1 locus of maize, has been shown to increase expression of genes in chimeric gene constructs. U.S. Pat. Nos. 5,424,412 and 5,593,874 disclose the use of specific introns in gene expression constructs, and Gallie et al. (*Plant Physiol.* 106:929-939, 1994) also have shown that introns are useful for regulating gene expression on a tissue specific basis. To further enhance or to optimize AHAS small subunit gene expression, the plant expression vectors of the invention may also contain DNA sequences containing matrix attachment regions (MARs). Plant cells transformed with such modified expression systems, then, may exhibit overexpression or constitutive expression of a nucleotide sequence of the invention.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus) (*Virology* 154:9-20), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The promoters can be selected based on the desired outcome. The nucleic acids can be combined with constitutive, tissue-preferred, or other promoters for expression in plants.

Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Tissue-preferred promoters can be utilized to target enhanced AHASL1 expression within a particular plant tissue. Such tissue-preferred promoters include, but are not limited to, leaf-preferred promoters, root-preferred promoters, seed-preferred promoters, and stem-preferred promoters. Tissue-preferred promoters include Yamamoto et al. (1997) *Plant J.* 12(2):255-265; Kawamata et al. (1997) *Plant Cell Physiol.* 38(7):792-803; Hansen et al. (1997) *Mol. Gen. Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol. Biol.* 23(6): 1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

In one embodiment, the nucleic acids of interest are targeted to the chloroplast for expression. In this manner, where the nucleic acid of interest is not directly inserted into the chloroplast, the expression cassette will additionally contain a chloroplast-targeting sequence comprising a nucleotide sequence that encodes a chloroplast transit peptide to direct the gene product of interest to the chloroplasts. Such transit peptides are known in the art. With respect to chloroplast-targeting sequences, "operably linked" means that the nucleic acid sequence encoding a transit peptide (i.e., the chloroplast-targeting sequence) is linked to the AHASL1 polynucleotide of the invention such that the two sequences are contiguous and in the same reading frame. See, for example, Von Heijne et al. (1991) *Plant Mol. Biol. Rep.* 9:104-126; Clark et al. (1989) *J. Biol. Chem.* 264: 17544-17550; Della-Cioppa et al. (1987) *Plant Physiol.* 84:965-968; Romer et al. (1993) *Biochem. Biophys. Res. Comnun.* 196:1414-1421; and Shah et al. (1986) *Science* 233:478-481. While the AHASL1 proteins of the invention include a native chloroplast transit peptide, any chloroplast transit peptide known in art can be fused to the amino acid sequence of a mature AHASL1 protein of the invention by operably linking a chloroplast-targeting sequence to the 5'-end of a nucleotide sequence encoding a mature AHASL1 protein of the invention.

Chloroplast targeting sequences are known in the art and include the chloroplast small subunit of ribulose-1,5-bisphosphate carboxylase (Rubisco) (de Castro Silva Filho et al. (1996) *Plant Mol. Biol.* 30:769-780; Schnell et al. (1991) *J. Biol. Chem.* 266(5):3335-3342); 5-(enolpyruvyl)shikimate-3-phosphate synthase (EPSPS) (Archer et al. (1990) *J. Bioenerg. Biomemb.* 22(6):789-810); tryptophan synthase (Zhao et al. (1995) *J. Biol. Chem.* 270(11):6081-6087); plastocyanin (Lawrence et al. (1997) *J. Biol. Chem.* 272

(33):20357-20363); chorismate synthase (Schmidt et al. (1993) *J. Biol. Chem.* 268(36):27447-27457); and the light harvesting chlorophyll a/b binding protein (LHBP) (Lamppa et al. (1988) *J. Biol. Chem.* 263:14996-14999). See also Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

The nucleic acids of interest to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

As disclosed herein, the AHASL1 nucleotide sequences of the invention find use in enhancing the herbicide tolerance of plants that comprise in their genomes a gene encoding a herbicide-tolerant AHASL1 protein. Such a gene may be an endogenous gene or a transgene. Additionally, in certain embodiments, the nucleic acid sequences of the present invention can be stacked with any combination of polynucleotide sequences of interest in order to create plants with a desired phenotype. For example, the polynucleotides of the present invention may be stacked with any other polynucleotides encoding polypeptides having pesticidal and/or insecticidal activity, such as, for example, the *Bacillus thuringiensis* toxin proteins (described in U.S. Pat. Nos. 5,366,892; 5,747,450; 5,737,514; 5,723,756; 5,593,881; and Geiser et al. (1986) *Gene* 48:109). The combinations generated can also include multiple copies of any one of the polynucleotides of interest.

It is recognized that with these nucleotide sequences, antisense constructions, complementary to at least a portion of the messenger RNA (mRNA) for the AHASL1 polynucleotide sequences can be constructed. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, preferably 80%, more preferably 85% sequence identity to the corresponding antisensed sequences may be used. Furthermore, portions of the antisense nucleotides may be used to disrupt the expression of the target gene. Generally, sequences of at least 50 nucleotides, 100 nucleotides, 200 nucleotides, or greater may be used.

The nucleotide sequences of the present invention may also be used in the sense orientation to suppress the expression of endogenous genes in plants. Methods for suppressing gene expression in plants using nucleotide sequences in the sense orientation are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, preferably greater than about 65% sequence identity, more preferably greater than about 85% sequence identity, most preferably greater than about 95% sequence identity. See, U.S. Pat. Nos. 5,283,184 and 5,034,323; herein incorporated by reference.

While the herbicide-resistant AHASL1 polynucleotides of the invention find use as selectable marker genes for plant transformation, the expression cassettes of the invention can include another selectable marker gene for the selection of transformed cells. Selectable marker genes, including those of the present invention, are utilized for the selection of transformed cells or tissues. Marker genes include, but are not limited to, genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). See generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Aci. USA* 86:5400-5404; Fuerst et al. (1989) *Proc. Natl. Acad. Sci. USA* 86:2549-2553; Deuschle et al. (1990) *Science* 248:480-483; Gossen (1993) *Ph.D. Thesis*, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) *Ph.D. Thesis*, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference.

The above list of selectable marker genes is not meant to be limiting. Any selectable marker gene can be used in the present invention.

The isolated polynucleotide molecules comprising nucleotide sequence that encode the AHASL1 proteins of the invention can be used in vectors to transform plants so that the plants created have enhanced resistant to herbicides, particularly imidazolinone herbicides. The isolated AHASL1 polynucleotide molecules of the invention can be used in vectors alone or in combination with a nucleotide sequence encoding the small subunit of the AHAS (AHASS) enzyme in conferring herbicide resistance in plants. See, U.S. Pat. No. 6,348,643; which is herein incorporated by reference.

The invention also relates to a plant expression vector comprising a promoter that drives expression in a plant operably linked to an isolated polynucleotide molecule of the invention. The isolated polynucleotide molecule comprises a nucleotide sequence encoding an AHASL1 protein, particularly an AHASL1 protein comprising an amino sequence that is set forth in SEQ ID NO: 2, or a functional fragment and variant thereof. The plant expression vector of the invention does not depend on a particular promoter, only that such a promoter is capable of driving gene expression in a plant cell. Preferred promoters include constitutive promoters and tissue-preferred promoters.

The transformation vectors of the invention can be used to produce plants transformed with a gene of interest. The transformation vector will comprise a selectable marker gene of the invention and a gene of interest to be introduced and typically expressed in the transformed plant. Such a selectable marker gene comprises a herbicide-resistant AHASL1 polynucleotide of the invention operably linked to a promoter that drives expression in a host cell. For use in plants and plant cells, the transformation vector comprises a selectable marker gene comprising a herbicide-resistant AHASL1 polynucleotide of the invention operably linked to a promoter that drives expression in a plant cell.

The genes of interest of the invention vary depending on the desired outcome. For example, various changes in phenotype can be of interest including modifying the fatty acid composition in a plant, altering the amino acid content of a plant, altering a plant's insect and/or pathogen defense mechanisms, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

In one embodiment of the invention, the genes of interest include insect resistance genes such as, for example, *Bacillus thuringiensis* toxin protein genes (U.S. Pat. Nos. 5,366,892; 5,747,450; 5,736,514; 5,723,756; 5,593,881; and Geiser et al. (1986) *Gene* 48:109).

The AHASL1 proteins or polypeptides of the invention can be purified from, for example, rice plants and can be used in compositions. Also, an isolated polynucleotide molecule encoding an AHASL1 protein of the invention can be used to express an AHASL1 protein of the invention in a microbe such as *E. coli* or a yeast. The expressed AHASL1 protein can be purified from extracts of *E. coli* or yeast by any method known to those or ordinary skill in the art.

The invention also relates to a method for creating a transgenic plant that is resistant to herbicides, comprising transforming a plant with a plant expression vector comprising a promoter that drives expression in a plant operably linked to an isolated polynucleotide molecule of the invention. The isolated polynucleotide molecule comprises a nucleotide sequence encoding an AHASL1 protein of the invention, particularly an AHASL1 protein comprising: an amino sequence that is set forth in SEQ ID NO: 2, an amino acid sequence encoded by SEQ ID NO: 1 or 3, or a functional fragment and variant of said amino acid sequences.

The invention also relates to the non-transgenic rice plants, transgenic plants produced by the methods of the invention, and progeny and other descendants of such non-transgenic and transgenic plants, which plants exhibit enhanced or increased resistance to herbicides that interfere with the AHAS enzyme, particularly imidazolinone and sulfonylurea herbicides.

The AHASL1 polynucleotides of the invention, particularly those encoding herbicide-resistant AHASL1 proteins, find use in methods for enhancing the resistance of herbicide-tolerant plants. In one embodiment of the invention, the herbicide-tolerant plants comprise a herbicide-tolerant or herbicide resistant AHASL1 protein. The herbicide-tolerant plants include both plants transformed with a herbicide-tolerant AHASL1 nucleotide sequences and plants that comprise in their genomes an endogenous gene that encodes a herbicide-tolerant AHASL1 protein. Nucleotide sequences encoding herbicide-tolerant AHASL1 proteins and herbicide-tolerant plants comprising an endogenous gene that encodes a herbicide-tolerant AHASL1 protein include the polynucleotides and plants of the present invention and those that are known in the art. See, for example, U.S. Pat. Nos. 5,013,659, 5,731,180, 5,767,361, 5,545,822, 5,736,629, 5,773,703, 5,773,704, 5,952,553 and 6,274,796; all of which are herein incorporated by reference. Such methods for enhancing the resistance of herbicide-tolerant plants comprise transforming a herbicide-tolerant plant with at least one polynucleotide construction comprising a promoter that drives expression in a plant cell that is operably linked to a herbicide resistant AHASL1 polynucleotide of the invention, particularly the polynucleotide encoding a herbicide-resistant AHASL1 protein set forth in SEQ ID NO: 1 or 3 polynucleotides encoding the amino acid sequence set forth in SEQ ID NO: 2, and fragments and variants said polynucleotides that encode polypeptides comprising herbicide-resistant AHAS activity.

Numerous plant transformation vectors and methods for transforming plants are available. See, for example, An, G. et al. (1986) *Plant Physiol.,* 81:301-305; Fry, J., et al. (1987) *Plant Cell Rep.* 6:321-325; Block, M. (1988) *Theor. Appl. Genet.* 76:767-774; Hinchee, et al. (1990) *Stadler. Genet. Symp.* 203212.203-212; Cousins, et al. (1991) *Aust. J. Plant Physiol.* 18:481-494; Chee, P. P. and Slightom, J. L. (1992) *Gene.* 118:255-260; Christou, et al. (1992) *Trends. Biotechnol.* 10:239-246; D'Halluin, et al. (1992) *Bio/Technol.* 10:309-314; Dhir, et al. (1992) *Plant Physiol.* 99:81-88; Casas et al. (1993) *Proc. Nat. Acad. Sci. USA* 90:11212-11216; Christou, P. (1993) *In Vitro Cell. Dev. Biol.-Plant;* 29P:119-124; Davies, et al. (1993) *Plant Cell Rep.* 12:180-183; Dong, J. A. and Mchughen, A. (1993) *Plant Sci.* 91:139-148; Franklin, C. I. and Trieu, T. N. (1993) *Plant. Physiol* 102:167; Golovkin, et al. (1993) *Plant Sci.* 90:41-52; Guo Chin Sci. Bull. 38:2072-2078; Asano, et al. (1994) *Plant Cell Rep.* 13; Ayeres N. M. and Park, W. D. (1994) *Crit. Rev. Plant. Sci.* 13:219-239; Barcelo, et al. (1994) *Plant. J.* 5:583-592; Becker, et al. (1994) *Plant. J.* 5:299-307; Borkowska et al. (1994) *Acta. Physiol Plant.* 16:225-230; Christou, P. (1994) *Agro. Food. Ind. Hi Tech.* 5: 17-27; Eapen et al. (1994) *Plant Cell Rep.* 13:582-586; Hartman, et al. (1994) *Bio-Technology* 12: 919923; Ritala, et al. (1994) *Plant. Mol. Biol.* 24:317-325; and Wan, Y. C. and Lemaux, P. G. (1994) *Plant Physiol.* 104:3748.

The methods of the invention involve introducing a polynucleotide construct into a plant. By "introducing" is intended presenting to the plant the polynucleotide construct in such a manner that the construct gains access to the interior of a cell of the plant. The methods of the invention do not depend on a particular method for introducing a polynucleotide construct to a plant, only that the polynucleotide construct gains access to the interior of at least one cell of the plant. Methods for introducing polynucleotide constructs into plants are known in the art including, but not limited to, stable transformation methods, transient transformation methods, and virus-mediated methods.

By "stable transformation" is intended that the polynucleotide construct introduced into a plant integrates into the genome of the plant and is capable of being inherited by progeny thereof. By "transient transformation" is intended that a polynucleotide construct introduced into a plant does not integrate into the genome of the plant.

For the transformation of plants and plant cells, the nucleotide sequences of the invention are inserted using standard techniques into any vector known in the art that is suitable for expression of the nucleotide sequences in a plant or plant cell. The selection of the vector depends on the preferred transformation technique and the target plant species to be transformed. In an embodiment of the invention, an AHASL1 nucleotide sequence is operably linked to a plant promoter that is known for high-level expression in a plant cell, and this construct is then introduced into a plant that that is susceptible to an imidazolinone herbicide and a transformed plant it regenerated. The transformed plant is tolerant to exposure to a level of an imidazolinone herbicide that would kill or significantly injure an untransformed plant. This method can be applied to any plant species; however, it is most beneficial when applied to crop plants, particularly crop plants that are typically grown in the presence of at least one herbicide, particularly an imidazolinone herbicide.

Methodologies for constructing plant expression cassettes and introducing foreign nucleic acids into plants are generally known in the art and have been previously described. For example, foreign DNA can be introduced into plants, using tumor-inducing (Ti) plasmid vectors. Other methods utilized for foreign DNA delivery involve the use of PEG mediated protoplast transformation, electroporation, microinjection whiskers, and biolistics or microprojectile bombardment for direct DNA uptake. Such methods are known in the art. (U.S. Pat. No. 5,405,765 to Vasil et al.; Bilang et al. (1991) *Gene* 100: 247-250; Scheid et al., (1991) *Mol. Gen. Genet.,* 228: 104-112; Guerche et al., (1987) *Plant Science* 52: 111-116; Neuhause et al., (1987) *Theor. Appl. Genet.* 75: 30-36; Klein et al., (1987) *Nature* 327: 70-73; Howell et al., (1980) *Science* 208:1265; Horsch et al., (1985) *Science* 227: 1229-1231; DeBlock et al., (1989) *Plant Physiology* 91: 694-701; *Methods for Plant Molecular Biology* (Weissbach and Weissbach, eds.) Academic Press, Inc. (1988) and *Methods in Plant Molecular Biology* (Schuler and Zielinski, eds.) Academic Press, Inc. (1989). The method of transformation depends upon the plant cell to be transformed, stability of vectors used, expression level of gene products and other parameters.

Other suitable methods of introducing nucleotide sequences into plant cells and subsequent insertion into the plant genome include microinjection as Crossway et al. (1986) *Biotechniques* 4:320-334, electroporation as described by Riggs et al. (1986) *Proc. Natl. Acad. Sci. USA* 83:5602-5606, *Agrobacterium*-mediated transformation as described by Townsend et al., U.S. Pat. No. 5,563,055, Zhao et al., U.S. Pat. No. 5,981,840, direct gene transfer as described by Paszkowski et al. (1984) *EMBO J.* 3:2717-2722, and ballistic particle acceleration as described in, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods,* ed. Gamborg and Phillips (Springer-Verlag, Berlin); McCabe et al. (1988) *Biotechnology* 6:923-926); and Lec1 transformation (WO 00/28058). Also see, Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/ Technology* 6:923-926 (soybean); Finer and McMullen (1991) *In Vitro Cell Dev. Biol.* 27P: 175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods,* ed. Gamborg (Springer-Verlag, Berlin) (maize); Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; Bowen et al., U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues,* ed. Chapman et al. (Longman, New York), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

The polynucleotides of the invention may be introduced into plants by contacting plants with a virus or viral nucleic acids. Generally, such methods involve incorporating a polynucleotide construct of the invention within a viral DNA or RNA molecule. It is recognized that the an AHASL1 protein of the invention may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing polynucleotide constructs into plants and expressing a protein encoded therein, involving viral DNA or RNA molecules, are known in the art. See, for example, U.S. Pat. Nos. 5,889,191, 5,889,190, 5,866,785, 5,589,367 and 5,316,931; herein incorporated by reference.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a polynucleotide construct of the invention, for example, an expression cassette of the invention, stably incorporated into their genome.

The present invention may be used for transformation of any plant species, including, but not limited to, monocots and dicots. Examples of plant species of interest include, but are not limited to, corn or maize (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*), sunflower (*Helianthus annuus*), safflower (*Carthamus tinctorius*), wheat (*Triticum aestivum, T. Turgidum* ssp. durum), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers. Preferably, plants of the present invention are crop plants (for example, sunflower, *Brassica* sp., cotton, sugar, beet, soybean, peanut, alfalfa, safflower, tobacco, corn, rice, wheat, rye, barley triticale, sorghum, millet, etc.).

The herbicide resistant plants of the invention find use in methods for controlling weeds. Thus, the present invention further provides a method for controlling weeds in the vicinity of a herbicide-resistant plant of the invention. The method comprises applying an effective amount of a herbicide to the weeds and to the herbicide-resistant plant, wherein the plant has increased resistance to at least one herbicide, particularly an imidazolinone or sulfonylurea herbicide, when compared to a wild-type plant. In such a method for controlling weeds, the herbicide-resistant plants of the invention are preferably crop plants, including, but not limited to, rice, sunflower, alfalfa, *Brassica* sp., soybean, cotton, safflower, peanut, tobacco, tomato, potato, wheat, maize, sorghum, barley, rye, millet, and sorghum.

By providing plants having increased resistance to herbicides, particularly imidazolinone and sulfonylurea herbicides, a wide variety of formulations can be employed for protecting plants from weeds, so as to enhance plant growth and reduce competition for nutrients. A herbicide can be used by itself for pre-emergence, post-emergence, pre-planting and at planting control of weeds in areas surrounding the plants described herein or an imidazolinone herbicide formulation can be used that contains other additives. The herbicide can also be used as a seed treatment. Additives found in an imidazolinone or sulfonylurea herbicide formulation include other herbicides, detergents, adjuvants, spreading agents, sticking agents, stabilizing agents, or the like. The herbicide formulation can be a wet or dry preparation and can include, but is not limited to, flowable powders, emulsifiable concentrates and liquid concentrates. The herbicide and herbicide formulations can be applied in accordance with conventional methods, for example, by spraying, irrigation, dusting, or the like.

The present invention provides non-transgenic and transgenic seeds with increased tolerance to at least one herbicide, particularly an AHAS-inhibiting herbicide, more particularly an imidazolinone herbicide. Such seeds include, for example, non-transgenic rice seeds comprising the herbicide-tolerance characteristics of the plant with NCIMB Accession Number NCIMB 41262, and transgenic seeds comprising an IMI nucleic acid molecule of the invention that encodes an IMI protein.

The present invention provides methods for producing a herbicide-resistant plant, particularly a herbicide-resistant rice plant, through conventional plant breeding involving sexual reproduction. The methods comprise crossing a first plant that is resistant to a herbicide to a second plant that is not resistant to the herbicide. The first plant can be any of the herbicide resistant plants of the present invention including, for example, transgenic plants comprising at least one of the polynucleotides of the present invention that encode a herbicide resistant IMI protein and non-transgenic rice plants that comprise the herbicide-tolerance characteristics of the rice plant with NCIMB Accession Number NCIMB 41262. The second plant can be any plant that is capable of producing viable progeny plants (i.e., seeds) when crossed with the first plant. Typically, but not necessarily, the first and second plants are of the same species. The methods of the invention can further involve one or more generations of backcrossing the progeny plants of the first cross to a plant of the same line or genotype as either the first or second plant. Alternatively, the progeny of the first cross or any subsequent cross can be crossed to a third plant that is of a different line or genotype than either the first or second plant. The methods of the invention can additionally involve selecting plants that comprise the herbicide tolerance characteristics of the first plant.

The present invention further provides methods for increasing the herbicide-resistance of a plant, particularly a herbicide-resistant rice plant, through conventional plant breeding involving sexual reproduction. The methods comprise crossing a first plant that is resistant to a herbicide to a second plant that may or may not be resistant to the herbicide or may be resistant to different herbicide or herbicides than the first plant. The first plant can be any of the herbicide resistant plants of the present invention including, for example, transgenic plants comprising at least one of the IMI nucleic acids of the present invention that encode IMI protein and non-transgenic rice plants that comprise the herbicide-tolerance characteristics of the rice plant with NCIMB Accession Number NCIMB 41262. The second plant can be any plant that is capable of producing viable progeny plants (i.e., seeds) when crossed with the first plant. Typically, but not necessarily, the first and second plants are of the same species. The progeny plants produced by this method of the present invention have increased resistance to a herbicide when compared to either the first or second plant or both. When the first and second plants are resistant to different herbicides, the progeny plants will have the combined herbicide tolerance characteristics of the first and second plants. The methods of the invention can further involve one or more generations of backcrossing the progeny plants of the first cross to a plant of the same line or genotype as either the first or second plant. Alternatively, the progeny of the first cross or any subsequent cross can be crossed to a third plant that is of a different line or genotype than either the first or second plant. The methods of the invention can additionally involve selecting plants that comprise the herbicide tolerance characteristics of the first plant, the second plant, or both the first and the second plant.

The plants of the present invention can be transgenic or non-transgenic. An example of a non-transgenic rice plant having increased resistance to imidazolinone is the rice plant (IMINTA 16) having NCIMB Accession Number NCIMB 41262; or mutant, recombinant, or a genetically engineered derivative of the plant having NCIMB Accession Number NCIMB 41262; or of any progeny of the plant having NCIMB Accession Number NCIMB 41262; or a plant that is a progeny of any of these plants; or a plant that comprises the herbicide tolerance characteristics of the plant having NCIMB Accession Number NCIMB 41262.

The present invention also provides plants, plant organs, plant tissues, plant cells, seeds, and non-human host cells that are transformed with the at least one polynucleotide molecule, expression cassette, or transformation vector of the invention. Such transformed plants, plant organs, plant tissues, plant cells, seeds, and non-human host cells have enhanced tolerance or resistance to at least one herbicide, at levels of the herbicide that kill or inhibit the growth of an untransformed plant, plant tissue, plant cell, or non-human host cell, respectively. Preferably, the transformed plants, plant tissues, plant cells, and seeds of the invention are *Arabidopsis thaliana* and crop plants.

The present invention provides methods that involve the use of at least one AHAS-inhibiting herbicide selected from the group consisting of imidazolinone herbicides, sulfonylurea herbicides, triazolopyrimidine herbicides, pyrimidinyloxybenzoate herbicides, sulfonylamino-carbonyltriazolinone herbicides, and mixtures thereof. In these methods, the AHAS-inhibiting herbicide can be applied by any method known in the art including, but not limited to, seed treatment, soil treatment, and foliar treatment.

Prior to application, the AHAS-inhibiting herbicide can be converted into the customary formulations, for example solutions, emulsions, suspensions, dusts, powders, pastes and granules. The use form depends on the particular intended purpose; in each case, it should ensure a fine and even distribution of the compound according to the invention.

The formulations are prepared in a known manner (see e.g. for review U.S. Pat. No. 3,060,084, EP-A 707 445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pages 8-57 and et seq. WO 91/13546, U.S. Pat. Nos. 4,172,714, 4,144,050, 3,920,442, 5,180,587, 5,232,701, 5,208,030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989 and Mollet, H., Grubemann, A., Formulation technology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8), for example by extending the active compound with auxiliaries suitable for the formulation of agrochemicals, such as solvents and/or carriers, if desired emulsifiers, surfactants and dispersants, preservatives, antifoaming agents, anti-freezing agents, for seed treatment formulation also optionally colorants and/or binders and/or gelling agents.

Examples of suitable solvents are water, aromatic solvents (for example Solvesso products, xylene), paraffins (for example mineral oil fractions), alcohols (for example methanol, butanol, pentanol, benzyl alcohol), ketones (for example cyclohexanone, gamma-butyrolactone), pyrrolidones (NMP, NOP), acetates (glycol diacetate), glycols, fatty acid dimethylamides, fatty acids and fatty acid esters. In principle, solvent mixtures may also be used.

Examples of suitable carriers are ground natural minerals (for example kaolins, clays, talc, chalk) and ground synthetic minerals (for example highly disperse silica, silicates).

Suitable emulsifiers are nonionic and anionic emulsifiers (for example polyoxyethylene fatty alcohol ethers, alkylsulfonates and arylsulfonates).

Examples of dispersants are lignin-sulfite waste liquors and methylcellulose.

Suitable surfactants used are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenol ether, ethoxylated isooctylphenol, octylphenol, nonylphenol, alkylphenol polyglycol ethers, tributylphenyl polyglycol ether, tristearylphenyl polyglycol ether, alkylaryl polyether alcohols, alcohol and fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, highly polar solvents, for example dimethyl sulfoxide, N-methylpyrrolidone or water.

Also anti-freezing agents such as glycerin, ethylene glycol, propylene glycol and bactericides such as can be added to the formulation.

Suitable antifoaming agents are for example antifoaming agents based on silicon or magnesium stearate.

Suitable preservatives are for example Dichlorophen und enzylalkoholhemiformal.

Seed Treatment formulations may additionally comprise binders and optionally colorants.

Binders can be added to improve the adhesion of the active materials on the seeds after treatment. Suitable binders are block copolymers EO/PO surfactants but also polyvinylalcohols, polyvinylpyrrolidones, polyacrylates, polymethacrylates, polybutenes, polyisobutylenes, polystyrene, polyethyleneamines, polyethyleneamides, polyethyleneimines (Lupasol®, Polymin®), polyethers, polyurethanes, polyvinylacetate, tylose and copolymers derived from these polymers.

Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

An example of a suitable gelling agent is carrageen (Satiagel®).

Powders, materials for spreading, and dustable products can be prepared by mixing or concomitantly grinding the active substances with a solid carrier.

Granules, for example coated granules, impregnated granules and homogeneous granules, can be prepared by binding the active compounds to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the AHAS-inhibiting herbicide. In this case, the AHAS-inhibiting herbicides are employed in a purity of from 90% to 100% by weight, preferably 95% to 100% by weight (according to NMR spectrum). For seed treatment purposes, respective formulations can be diluted 2-10 fold leading to concentrations in the ready to use preparations of 0.01 to 60% by weight active compound by weight, preferably 0.1 to 40% by weight.

The AHAS-inhibiting herbicide can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the AHAS-inhibiting herbicide according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. However, it is also possible to prepare concentrates composed of active substance, wetter, tackifier, dispersant or emulsifier and, if appropriate, solvent or oil, and such concentrates are suitable for dilution with water.

The active compound concentrations in the ready-to-use preparations can be varied within relatively wide ranges. In general, they are from 0.0001 to 10%, preferably from 0.01 to 1% per weight.

The AHAS-inhibiting herbicide may also be used successfully in the ultra-low-volume process (ULV), it being possible to apply formulations comprising over 95% by weight of active compound, or even to apply the active compound without additives.

The following are examples of formulations:

1. Products for dilution with water for foliar applications. For seed treatment purposes, such products may be applied to the seed diluted or undiluted.

A) Water-Soluble Concentrates (SL, LS)

Ten parts by weight of the AHAS-inhibiting herbicide are dissolved in 90 parts by weight of water or a water-soluble solvent. As an alternative, wetters or other auxiliaries are added. The AHAS-inhibiting herbicide dissolves upon dilution with water, whereby a formulation with 10% (w/w) of AHAS-inhibiting herbicide is obtained.

B) Dispersible Concentrates (DC)

Twenty parts by weight of the AHAS-inhibiting herbicide are dissolved in 70 parts by weight of cyclohexanone with addition of 10 parts by weight of a dispersant, for example polyvinylpyrrolidone. Dilution with water gives a dispersion, whereby a formulation with 20% (w/w) of AHAS-inhibiting herbicide is obtained.

C) Emulsifiable Concentrates (EC)

Fifteen parts by weight of the AHAS-inhibiting herbicide are dissolved in 7 parts by weight of xylene with addition of calcium dodecylbenzenesulfonate and castor oil ethoxylate (in each case 5 parts by weight). Dilution with water gives an emulsion, whereby a formulation with 15% (w/w) of AHAS-inhibiting herbicide is obtained.

D) Emulsions (EW, EO, ES)

Twenty-five parts by weight of the AHAS-inhibiting herbicide are dissolved in 35 parts by weight of xylene with addition of calcium dodecylbenzenesulfonate and castor oil ethoxylate (in each case 5 parts by weight). This mixture is introduced into 30 parts by weight of water by means of an emulsifier machine (e.g. Ultraturrax) and made into a homogeneous emulsion. Dilution with water gives an emulsion, whereby a formulation with 25% (w/w) of AHAS-inhibiting herbicide is obtained.

E) Suspensions (SC, OD, FS)

In an agitated ball mill, 20 parts by weight of the AHAS-inhibiting herbicide are comminuted with addition of 10 parts by weight of dispersants, wetters and 70 parts by weight of water or of an organic solvent to give a fine AHAS-inhibiting herbicide suspension. Dilution with water gives a stable suspension of the AHAS-inhibiting herbicide, whereby a formulation with 20% (w/w) of AHAS-inhibiting herbicide is obtained.

F) Water-Dispersible Granules and Water-Soluble Granules (WG, SG)

Fifty parts by weight of the AHAS-inhibiting herbicide are ground finely with addition of 50 parts by weight of dispersants and wetters and made as water-dispersible or water-soluble granules by means of technical appliances (for example extrusion, spray tower, fluidized bed). Dilution with water gives a stable dispersion or solution of the AHAS-inhibiting herbicide, whereby a formulation with 50% (w/w) of AHAS-inhibiting herbicide is obtained.

G) Water-Dispersible Powders and Water-Soluble Powders (WP, SP, SS, WS)

Seventy-five parts by weight of the AHAS-inhibiting herbicide are ground in a rotor-stator mill with addition of 25 parts by weight of dispersants, wetters and silica gel. Dilution with water gives a stable dispersion or solution of the AHAS-inhibiting herbicide, whereby a formulation with 75% (w/w) of AHAS-inhibiting herbicide is obtained.

I) Gel-Formulation (GF)

In an agitated ball mill, 20 parts by weight of the AHAS-inhibiting herbicide are comminuted with addition of 10 parts by weight of dispersants, 1 part by weight of a gelling agent wetters and 70 parts by weight of water or of an organic solvent to give a fine AHAS-inhibiting herbicide suspension. Dilution with water gives a stable suspension of the AHAS-inhibiting herbicide, whereby a formulation with 20% (w/w) of AHAS-inhibiting herbicide is obtained. This gel formulation is suitable for us as a seed treatment.

2. Products to be applied undiluted for foliar applications. For seed treatment purposes, such products may be applied to the seed diluted.

A) Dustable Powders (DP, DS)

Five parts by weight of the AHAS-inhibiting herbicide are ground finely and mixed intimately with 95 parts by weight of finely divided kaolin. This gives a dustable product having 5% (w/w) of AHAS-inhibiting herbicide.

B) Granules (GR, FG, GG, MG)

One-half part by weight of the AHAS-inhibiting herbicide is ground finely and associated with 95.5 parts by weight of carriers, whereby a formulation with 0.5% (w/w) of AHAS-inhibiting herbicide is obtained. Current methods are extrusion, spray-drying or the fluidized bed. This gives granules to be applied undiluted for foliar use.

Conventional seed treatment formulations include for example flowable concentrates FS, solutions LS, powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds.

In a preferred embodiment a FS formulation is used for seed treatment. Typcially, a FS formulation may comprise 1-800 g/l of active ingredient, 1-200 g/l Surfactant, 0 to 200 g/l antifreezing agent, 0 to 400 g/l of binder, 0 to 200 g/l of a pigment and up to 1 liter of a solvent, preferably water.

The present invention non-transgenic and transgenic seeds of the herbicide-resistant plants of the present invention. Such seeds include, for example, non-transgenic rice seeds comprising the herbicide-tolerance characteristics of the plant with NCIMB Accession Number NCIMB 41262, and transgenic seeds comprising a polynucleotide molecule of the invention that encodes an IMI protein.

For seed treatment, seeds of the herbicide resistant plants according of the present invention are treated with herbicides, preferably herbicides selected from the group consisting of AHAS-inhibiting herbicides such as amidosulfuron, azimsulfuron, bensulfuron, chlorimuron, chlorsulfuron, cinosulfuron, cyclosulfamuron, ethametsulfuron, ethoxysulfuron, flazasulfuron, flupyrsulfuron, foramsulfuron, halosulfuron, imazosulfuron, iodosulfuron, mesosulfuron, metsulfuron, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, imazamethabenz, imazamox, imazapic, imazapyr, imazaquin, imazethapyr, cloransulam, diclosulam, florasulam, flumetsulam, penoxsulam, bispyribac, pyriminobac, propoxycarbazone, flucarbazone, pyribenzoxim, pyriftalid, pyrithiobac, and mixtures thereof, or with a formulation comprising a AHAS-inhibiting herbicide.

The term seed treatment comprises all suitable seed treatment techniques known in the art, such as seed dressing, seed coating, seed dusting, seed soaking, and seed pelleting.

In accordance with one variant of the present invention, a further subject of the invention is a method of treating soil by the application, in particular into the seed drill: either of a granular formulation containing the AHAS-inhibiting herbicide as a composition/formulation (e.g. a granular formulation, with optionally one or more solid or liquid, agriculturally acceptable carriers and/or optionally with one or more agriculturally acceptable surfactants. This method is advantageously employed, for example, in seedbeds of cereals, maize, cotton, and sunflower.

The present invention also comprises seeds coated with or containing with a seed treatment formulation comprising at least one AHAS-inhibiting herbicide selected from the group consisting of amidosulfuron, azimsulfuron, bensulfuron, chlorimuron, chlorsulfuron, cinosulfuron, cyclosulfamuron, ethametsulfuron, ethoxysulfuron, flazasulfuron, flupyrsulfuron, foramsulfuron, halosulfuron, imazosulfuron, iodosulfuron, mesosulfuron, metsulfuron, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, imazamethabenz, imazamox, imazapic, imazapyr, imazaquin, imazethapyr, cloransulam, diclosulam, florasulam, flumetsulam, metosulam, penoxsulam, bispyribac, pyriminobac, propoxycarbazone, flucarbazone, pyribenzoxim, pyriftalid and pyrithiobac.

The term seed embraces seeds and plant propagules of all kinds including but not limited to true seeds, seed pieces, suckers, corms, bulbs, fruit, tubers, grains, cuttings, cut shoots and the like and means in a preferred embodiment true seeds.

The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

The seed treatment application with the AHAS-inhibiting herbicide or with a formulation comprising the AHAS-inhibiting herbicide is carried out by spraying or dusting the seeds before sowing of the plants and before emergence of the plants.

In the treatment of seeds, the corresponding formulations are applied by treating the seeds with an effective amount of the AHAS-inhibiting herbicide or a formulation comprising the AHAS-inhibiting herbicide. Herein, the application rates are generally from 0.1 g to 10 kg of the a.i. (or of the mixture of a.i. or of the formulation) per 100 kg of seed, preferably from 1 g to 5 kg per 100 kg of seed, in particular from 1 g to 2.5 kg per 100 kg of seed. For specific crops such as lettuce the rate can be higher.

The present invention provides a method for combating undesired vegetation or controlling weeds comprising contacting the seeds of the resistant plants according to the present invention before sowing and/or after pregermination with an AHAS-inhibiting herbicide. The method can further comprise sowing the seeds, for example, in soil in a field or in a potting medium in greenhouse. The method finds particular use in combating undesired vegetation or controlling weeds in the immediate vicinity of the seed.

The control of undesired vegetation is understood as meaning the killing of weeds and/or otherwise retarding or inhibiting the normal growth of the weeds. Weeds, in the broadest sense, are understood as meaning all those plants which grow in locations where they are undesired.

The weeds of the present invention include, for example, dicotyledonous and monocotyledonous weeds. Dicotyledonous weeds include, but are not limited to, weeds of the genera: *Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindemia, Lamium, Veronica, Abutilon, Emex, Datura, Viola, Galeopsis, Papaver, Centaurea, Trifolium, Ranunculus, and Taraxacum. Monocotyledonous weeds include, but are not limited to, weeds of the genera: Echinochloa, Setaria, Panicum, Digitaria, Phleum, Poa, Festuca, Eleusine, Brachiaria,*

*Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus,* and *Apera*.

In addition, the weeds of the present invention can include, for example, crop plants that are growing in an undesired location. For example, a volunteer maize plant that is in a field that predominantly comprises soybean plants can be considered a weed, if the maize plant is undesired in the field of soybean plants.

The articles "a" and "an" are used herein to refer to one or more than one (i.e., to at least one) of the grammatical object of the article. By way of example, "an element" means one or more elements.

As used herein, the word "comprising," or variations such as "comprises" or "comprising," will be understood to imply the inclusion of a stated element, integer or step, or group of elements, integers or steps, but not the exclusion of any other element, integer or step, or group of elements, integers or steps.

The following examples are offered by way of illustration and not by way of limitation.

EXAMPLE 1

Production of an Imidazolinone-Resistant Rice Line

AHASL is a nuclear encoded enzyme and its gene, in different species, has been sequenced in its wild form and other forms showing sites of mutation that confer resistance to sulfonylurea and imidazolinone herbicides. In order to produce rice plants with herbicide-resistant AHAS enzymes, rice seeds were treated with a chemical mutagen in an attempt to induce small changes at the active site of interaction with the herbicide in order to prevent inhibition. Leading rice varieties and elite rice lines were selected in order to generate a new mutation that is resistant to the most active imidazolinones in excellent germplasm. Selection pressure was based on exposure of four-leaf stage plants to two of the most active imidazolinone herbicides applied in one application during several generations until homozygous highly resistant lines were obtained. The imidazolinone-resistance rice lines were produced as described below.

In the late spring of growing season number 1, two samples of seeds (600 g each) of the rice cultivar IRGA 417 were treated with a 0.001 M sodium azide aqueous solution at pH 3 (phosphate buffer 0.067M). This treatment was applied by soaking each seed-sample in a two-liter Erlenmeyer containing one liter of the sodium azide solution, under constant shaking, for 18 hours, at room temperature. After treatment, the seeds were rinsed in tap water and, later on, they were partially dried-aerated on blotting paper sheets in order to extract the moisture from the seeds surface. Afterwards, treated seeds were directly sown at the field nursery in Concepcion del Uruguay, E.R., Argentina.

Treated ($M_1$) and untreated control seeds of the rice cultivar IRGA 417 were planting in the field nursery a rate of 50 plants per square meter. The plants were grown under flooded conditions until maturity (26% grain moisture) and bulk harvested. Seeds ($M_2$) of the plants were collected and dried in a convector drier for 14 h at 45° C. They were kept in close storage until next growing season.

In the late spring of growing season number 2, $M_2$ seeds were planted with an experimental seed planter for large areas at a rate of 50 kg/ha in at the field nursery in Concepcion del Uruguay, E.R., Argentina. An area of 3 ha was established comprising a population of approximately $6 \times 10^6$ $M_2$ plants. IRGA 417 (wild type) was also planted as a control. The entire area was subjected to a selection pressure with a mixture of two imidazolinone herbicides. Three separate applications were done with a commercial sprayer in different directions to prevent any escape and resulting in a 3× treatment. A total volume of 222 L/ha was sprayed at 50 psi, with Teejets 8002 nozzles, in each application. The rate of the 1× treatment was a mixture of Arsenal® (Imazapir 75 cc a.i/ha) and Cadre® (Imazapic 24.85 cc a.i/ha) in a water solution with a non-ionic surfactant (Citowett) at the rate of 0.25%. The applications were done at the four leaf-stage of the rice plants. No rainfall was registered during the 7 days after treatments.

Observations at regular times were done to survey the entire herbicide-treated area. At 90 days after the herbicide treatment, the surviving individuals were labeled and transplanted to the greenhouse for asexual multiplication and seed production. A total of 10 individual plants were grown, and the seed was harvested and dried in a seed incubator for 7 days at 50° C. As expected, none of the control plants (IRGA 417) survived the herbicide treatment.

Seeds ($M_3$) from selected $M_2$ plants were planted in individual pots under greenhouse conditions in Concepcion del Uruguay, E.R., Argentina during the winter immediately following the second season. A 2× treatment was applied with a backpack sprayer divided in two applications of a 1× rate of Arsenal® (Imazapir 75 cc a.i/ha) and Cadre® (Imazapic 24.85 cc a.i/ha) in a water solution with a non-ionic surfactant (Citowet) at the rate of 0.25%.

Tillers from the herbicide-tolerant plants (e.g., plants that survived herbicide treatments) were grown until maturity (26% grain moisture) and hand harvested. The harvested seed ($M_4$) was subjected to a dormancy breaking treatment of 7 days at 50° C. and prepared for the next growing season planting. Seeds from two herbicide-tolerant plants were kept separately. The seeds from were prepared for a late-season planting outdoors at Concepción del Uruguay, E.R., Argentina.

In the summer of growing season number 3, $M_4$ seeds of an herbicide-tolerant $M_3$ plant that was designated as IMINTA 16 were planted with at the rate of 50 kg/ha. A treatment of 2× of imidazolinone herbicides was applied at the four to five leaves stage of the rice plants as two applications of a 1× rate of Arsenal® (Imazapir 75 cc a.i/ha) and Cadre® (Imazapic 24.85 cc a.i/ha) in a water solution with a non-ionic surfactant (Citowet) at the rate of 0.25%. No phytotoxic symptoms were observed for plants of the IMINTA 16 line. No wild-type segregants (i.e., not tolerant to the herbicide treatment) were observed, and a highly homogenous population in agronomic and tolerance traits had been produced. Individual IMINTA 16 plants were transplanted into the greenhouse for seed production, and seeds ($M_5$) were harvested later that year.

EXAMPLE 2

An Imidazoline-Resistant Rice Line with a Mutation in the AHASL1 Gene

Genomic DNA was separately extracted from leaves of greenhouse-grown seedlings of the IMINTA 16 line described in Example 1 above and the AHASL1 gene was amplified by a polymerase chain reaction (PCR) method using the primers described below. The resulting products of the individual PCR amplifications were sequenced using standard methods.

The primers used for PCR and sequencing are provided in Table 1. The primers were selected manually by visual inspection of the publicly known rice sequences for *Oryza sativa* 'Kinmaze', *Oryza sativa japonica* and *Oryza sativa indica*. The primers were nested approximately every 400-

500 bp along the approximately 2000 bp of the AHAS gene. Several primers were designed for each 500 bp stretch to maximize the likelihood of success of amplification. No weight was given to conserved regions when choosing primers. The primer sequences were checked for hairpins and dimers via the website www.rnature.com/oligonucleoti-de.html. Because there are no introns present in the AHASL1 gene, the entire gene represents coding sequence, and is therefore conserved. Primers were designed to have a GC content close to 50% and similar melting temperatures, approximately 54-58° C. The primer names in Table 1 reflect the exact starting base position according to public AHASL1 nucleotide sequences for rice (e.g., GenBank Accession No. AB049822). U136851 refers to a region upstream of the start codon in the AHAS gene and was designed from a BAC clone (OSJNBa0053B21), accession no. AL731599.

TABLE 1

Primers for PCR Amplification and DNA Sequencing of the Rice AHASL1 Gene in IMINTA 16

| Primer Name | Sequence 5''to 3' | | Melting Temp. (° C.) | GC content (%) |
|---|---|---|---|---|
| | | Pair 1 | | |
| U136851 | GACATATGGGGCCCACTGT | (SEQ ID NO: 4) | 58.8 | 58 |
| L789 | GTAGATTCATCGAGGTGTC | (SEQ ID NO: 5) | 54.5 | 47.4 |
| | | Pair 2 | | |
| U642* | GTCCTTGATGTGGAGGACAT | (SEQ ID NO: 6) | 57.3 | 50 |
| L1369 | CATATTGCGGTGGGATCTCT | (SEQ ID NO: 7) | 57.3 | 50 |
| | | Pair 3 | | |
| U1229 | GGGCTTGAATGCTCTGCTAC | (SEQ ID NO: 8) | 59.4 | 55 |
| L1742 | CGGGTTGCCCAAGTATGTAT | (SEQ ID NO: 9) | 57.3 | 50 |
| | | Pair 4 | | |
| U1633 | ACCTCCCTGTGAAGGTGATG | (SEQ ID NO: 10) | 59.4 | 55 |
| L2155* | AGGATTACCATGCCAAGCAC | (SEQ ID NO: 11) | 57.3 | 50 |
| | | Alternate PCR primers and sequencing primers | | |
| U037 | CACCACCCACCATGGCTA | (SEQ ID NO: 12) | 58.2 | 61.1 |
| U114 | GTAAGAACCACCAGCGAC | (SEQ ID NO: 13) | 56 | 55.6 |
| U1109 | GTGGATAAGGCTGACCTGT | (SEQ ID NO: 14) | 56.7 | 52.6 |
| U1166 | GGGAAAATTGAGGCTTTTGCA | (SEQ ID NO: 15) | 55.9 | 42.9 |
| L1299 | CTCATTGTGCCATGCACTAA | (SEQ ID NO: 16) | 55.3 | 45 |
| U1721 | GCATACATACTTGGGCAAC | (SEQ ID NO: 17) | 54 | 47 |
| L2054 | CATACCACTCTTTATGGGTC | (SEQ ID NO: 18) | 52 | 45 |

*Also used U642 and L2155 as a PCR pair

When the PCR-amplified genomic DNA from the IMI-NTA 16 seedlings was examined, a single base change (i.e., transition, C to T) was identified in the coding region of the gene that caused an amino acid substitution in the AHASL1 protein at amino acid position 179 from Ala in the wild type line to Val in the IMINTA 16 line. The site of this substitution corresponds to position 205 in the *Arabidopsis thaliana* AHASL protein (see, Table 2 below). The Ala205Val substitution in the *Arabidopsis thaliana* AHASL protein is known to confer on plants that express this protein tolerance to imidazolinone herbicides.

EXAMPLE 3

Herbicide-Resistant Rice AHASL1 Proteins

The present invention discloses both the nucleotide and amino acid sequences for herbicide resistant rice AHASL1 polypeptides. Plants comprising herbicide-resistant AHASL1 polypeptides have been previously identified, and a number of conserved regions of AHASL1 polypeptides that are the sites of amino acids substitutions that confer herbicide resistance have been described. See, Devine and Eberlein (1997) "Physiological, biochemical and molecular aspects of herbicide resistance based on altered target sites". In: *Herbicide Activity: Toxicology, Biochemistry and Molecular Biology*, Roe et al. (eds.), pp. 159-185, IOS Press, Amsterdam; and Devine and Shukla, (2000) *Crop Protection* 19:881-889.

Using the AHASL1 polynucleotide molecules of the invention and methods known to those of ordinary skill in art, one can produce additional polynucleotide molecules encoding herbicide resistant AHASL1 polypeptides having one, two, three, or more amino acid substitutions at the identified sites in these conserved regions. Table 2 provides the conserved regions of AHASL1 proteins, the amino acid substitutions known to confer herbicide resistance within these conserved regions, and the corresponding amino acids in the rice AHASL1 protein set forth in SEQ ID NO: 2.

TABLE 2

Amino Acid Substitutions in Conserved Regions of AHASL Polypeptides
that are Known to Confer Herbicide-Resistance and their Equivalent
Position in Rice AHASL1 Polypeptides

| Conserved region[1] | Mutation[2] | Reference | Amino acid position in rice |
|---|---|---|---|
| VFAYPGGASMEIHQALTRS[3] (SEQ ID NO: 19) | $Ala_{122}$ to Thr | Bernasconi et al.[4] | $Ala_{96}$ |
| AITGQVPRRMIGT[3] (SEQ ID NO: 20) | $Pro_{197}$ to Ala | Boutsalis et al.[5] | $Pro_{171}$[12] |
| | $Pro_{197}$ to Thr | Guttieri et al.[6] | |
| | $Pro_{197}$ to His | Guttieri et al.[7] | |
| | $Pro_{197}$ to Leu | Guttieri et al.[6] | |
| | $Pro_{197}$ to Arg | Guttieri et al.[6] | |
| | $Pro_{197}$ to Ile | Boutsalis et al.[6] | |
| | $Pro_{197}$ to Gln | Guttieri et al.[6] | |
| | $Pro_{197}$ to Ser | Guttieri et al.[6] | |
| AFQETP[3] (SEQ ID NO: 21) | $Ala_{205}$ to Asp | Hartnett et al.[8] | $Ala_{179}$[13] |
| | $Ala_{205}$ to Val[11] | Simpson[9] | |
| QWFD[3] (SEQ ID NO: 22) | $Trp_{574}$ to Leu | Bruniard[10] Boutsalis et al.[5] | $Trp_{548}$ |
| IPSGG[3] (SEQ ID NO: 23) | $Ser_{653}$ to Asn | Chang & Duggleby[12] | $Ser_{627}$ |
| | $Ser_{653}$ to Thr | Lee et al.[13] | |
| | $Ser_{653}$ to Phe | | |

[1]Conserved regions from Devine and Eberlein (1997) "Physiological, biochemical and molecular aspects of herbicide resistance based on altered target sites". In: Herbicide Activity: Toxicology, Biochemistry and Molecular Biology, Roe et al. (eds.), pp. 159-185, IOS Press, Amsterdam and Devine and Shukla, (2000) Crop Protection 19: 881-889.

[2]Amino acid numbering corresponds to the amino acid sequence of the *Arabidopsis thaliana* AHASL polypeptide.

[3]The rice AHASL1 protein of the invention (SEQ ID NO: 2) has the same conserved regions.

[4]Bernasconi et al. (1995) J. Biol. Chem. 270(29): 17381-17385.

[5]Boutsalis et al. (1999) Pestic. Sci. 55: 507-516.

[6]Guttieri et al. (1995) Weed Sci. 43: 143-178.

[7]Guttieri et al. (1992) Weed Sci. 40: 670-678.

[8]Hartnett et al. (1990) "Herbicide-resistant plants carrying mutated acetolactate synthase genes," In: Managing Resistance to Agrochemicals: Fundamental Research to Practical Strategies, Green et al. (eds.), American Chemical Soc. Symp., Series No. 421, Washington, DC, USA

[9]Simpson (1998) Down to Earth 53(1): 26-35.

[10]Bruniard (2001) Inheritance of imidazolinone resistance, characterization of cross-resistance pattern, and identification of molecular markers in sunflower (Helianthus annuus L.). Ph.D. Thesis, North Dakota State University, Fargo, ND, USA, pp 1-78.

[11]The present invention discloses the amino acid sequence of a herbicide-resistant rice AHASL1 protein with the $Ala_{179}$ to Val substitution (SEQ ID NO: 2) and a polynucleotide sequences encoding this herbicide resistant AHASL1 (SEQ ID NOS: 1 and 3).

[12]Chang and Duggleby (1998) Biochem J. 333: 765-777.

[13]Lee et al. (1999) FEBS Lett. 452: 341-345.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A viable non-transgenic rice seed, comprising:

a mutagenized endogenous rice acetohydroxyacid synthase large subunit (AHASL1) polynucleotide having a sequence that encodes an herbicide-tolerant AHASL1 protein comprising the amino acid sequence of SEQ ID NO:2, SEQ ID NO:2 having a valine at position 179, wherein the polynucleotide is free of site-directed mutations; and a phenotype of tolerance to 75 cc active ingredient/hectare (a.i./ha) imazapyr and 24.85 g a.i./ha imazapic, as a result of the presence of the valine at position 179 of SEQ ID NO:2, wherein said sequence of the polynucleotide has been obtained by chemical mutagenesis using a chemical mutagen.

2. The viable non-transgenic seed of claim 1, said rice AHASL1 polynucleotide comprising the nucleotide sequence of SEQ ID NO: 1 or 3.

3. A viable non-transgenic rice seed, comprising:

a mutagenized endogenous rice acetohydroxyacid synthase large subunit (AHASL1) polynucleotide having a sequence that encodes a herbicide-tolerant AHASL1 protein comprising the amino acid sequence of SEQ ID NO:2, SEQ ID NO:2 having a valine at position 179, wherein the polynucleotide is free of sited-directed mutations; and a phenotype of tolerance to 75 cc active ingredient/hectare (a.i./ha) imazapyr and 24.85 g a.i./ha imazapic as a result of the presence of the valine at position 179 of SEQ ID NO:2, wherein said sequence of the polynucleotide has been obtained by chemical mutagenesis using a chemical mutagen, and wherein said herbicide-tolerant AHASL1 protein further comprises at least one member selected from the group consisting of:

(a) a threonine at amino acid position 96 of SEQ ID NO:2;

(b) an alanine, threonine, histidine, leucine, arginine, isoleucine, glutamine, or serine at amino acid position 171 of SEQ ID NO:2;

(c) a leucine at amino acid position 548 of SEQ ID NO:2; and (d) an asparagine, threonine, or phenylalanine at amino acid position 627 of SEQ ID NO:2.

4. A non-transgenic rice plant grown from the viable non-transgenic rice seed of claim 1, said non-transgenic rice plant comprising in its genome at least one copy of said AHASL1 polynucleotide, and said non-transgenic plant comprising, upon expressing said polynucleotide, a phenotype of tolerance to 75 cc active ingredient/hectare (a.i./ha) imazapyr and 24.85 g a.i./ha imazapic, as a result of the presence of the valine at position 179 of SEQ ID NO:2.

5. The non-transgenic rice plant of claim 4, wherein the non-transgenic rice plant:

(a) is of line IMINTA 16, a representative sample of seed of said line having been deposited under NCIMB Accession Number NCIMB 41262; or (b) is a progeny of the non-transgenic rice plant of line IMINTA 16.

6. The non-transgenic rice plant of claim 4, wherein said non-transgenic rice plant has enhanced tolerance to at least one herbicide chosen from the group of imidazolinone herbicides, sulfonylurea herbicides, triazolopyrimidine herbicides, pyrimidinyloxybenzoate herbicides, or sulfonylamino-carbonyltriazolinone herbicides as compared to that of a corresponding wild-type plant.

7. A method for growing a rice plant from the viable non-transgenic rice seed of claim 1 while controlling weeds in the vicinity of the rice plant, said method comprising:

(a) growing the rice plant from the viable seed of claim 1; and (b) applying an effective amount of an AHAS-inhibiting herbicide to the weeds and to the rice plant.

8. The method of claim 7, wherein said AHAS-inhibiting herbicide comprises at least one of: imazethapyr, imazapic, imazamox, imazaquin, imazethabenz, imazapyr, or a mixture of any two or more thereof.

9. The method of claim 7, wherein said AHAS-inhibiting herbicide comprises at least one of: chlorsulfuron, metsulfuron methyl, sulfometuron methyl, chlorimuron ethyl, thifensulfuron methyl, tribenuron methyl, bensulfuron methyl, nicosulfuron, ethametsulfuron methyl, rimsulfuron, triflusulfuron methyl, triasulfuron, primisulfuron methyl, cinosulfuron, amidosulfuron, flazasulfuron, imazosulfuron, pyrazosulfuron ethyl, halosulfuron, or a mixture of any two or more thereof.

10. The viable non-transgenic seed of claim 1, wherein said AHAS-inhibiting herbicide comprises at least one: imidazolinone herbicide, sulfonylurea herbicide, triazolopyrimidine herbicide, pyrimidinyloxybenzoate herbicide, sulfonylamino-carbonyltriazolinone herbicide, or a mixture of any two or more thereof.

11. A method for combating undesired vegetation comprising: contacting the viable non-transgenic seed of claim 1, before sowing and/or after pregermination, with an AHAS-inhibiting herbicide.

12. The method of claim 11, wherein said AHAS-inhibiting herbicide comprises at least one: imidazolinone herbicide, sulfonylurea herbicide, or a mixture thereof.

13. The method of claim 11, wherein said AHAS-inhibiting herbicide comprises at least one of: imazethapyr, imazapic, imazamox, imazaquin, imazethabenz, imazapyr, or a mixture of any two or more thereof.

14. A non-transgenic rice plant comprising:

a mutagenized endogenous rice acetohydroxyacid synthase large subunit (AHASL1) polynucleotide having a sequence that encodes a herbicide-tolerant AHASL1 protein comprising the amino acid sequence of SEQ ID NO:2, SEQ ID NO:2 having a valine at position 179, wherein the polynucleotide is free of site-directed mutations; and a phenotype of tolerance to 75 cc active ingredient/hectare (a.i./ha) imazapyr and 24.85 g a.i./ha imazapic, as a result of the presence of the valine at position 179 of SEQ ID NO:2, wherein, as a result of said phenotype, said non-transgenic rice plant, if treated with 75 cc a.i./ha imazapyr and 24.85 g a.i./ha imazapic, either (a) does not exhibit any phytotoxic symptoms, or (b) is not killed or inhibited in its growth, or both (a) and (b), and wherein said sequence of the polynucleotide has been obtained by chemical mutagenesis using a chemical mutagen.

15. The viable non-transgenic seed of claim 1, wherein a rice plant grown from the viable non-transgenic seed comprises the herbicide-tolerance characteristics of a plant of line IMINTA 16, a representative sample of seed of said line having been deposited under NCIMB Accession Number NCIMB 41262.

16. The viable non-transgenic seed of claim 1, further comprising an AHAS-inhibiting herbicide on a surface thereof, wherein a rice plant grown from the viable non-transgenic seed comprises no phytotoxic symptoms and is not a wild-type segregant.

17. A method for treating a rice plant according to claim 14, the method comprising applying an AHAS inhibiting herbicide to the plant.

18. The method of claim 17, wherein said AHAS-inhibiting herbicide comprises at least one: imidazolinone herbicide, sulfonylurea herbicide, or a mixture thereof.

19. The method of claim 17, wherein said AHAS-inhibiting herbicide comprises at least one of: imazethapyr, imazapic, imazamox, imazaquin, imazethabenz, imazapyr, or a mixture of any two or more thereof.

\* \* \* \* \*

```
                     SEQUENCE LISTING

<160> NUMBER OF SEQ ID NOS: 23

<210> SEQ ID NO 1
<211> LENGTH: 1961
<212> TYPE: DNA
<213> ORGANISM: Oryza sativa

<400> SEQUENCE: 1
cccaccatgg ctacgaccgc cgcggccgcg gccgccacct tgtccgccgc cgcgacggcc        60
aagaccggcc gtaagaacca ccagcgacac cacgtctttc ccgctcgagg ccgggtgggg       120
gcggcggcgg tcaggtgctc ggcggtgtcc ccggtcaccc cgccgtcccc ggcgccgccg       180
gccacgccgc tccggccgtg ggggccggcc gagccccgca agggcgcgga catcctcgtg       240
gaggcgctgg agcggtgcgg cgtcagcgac gtgttcgcct acccgggcgg cgcgtccatg       300
gagatccacc aggcgctgac gcgctccccg gtcatcacca accacctctt ccgccacgag       360
cagggcgagg cgttcgcggc gtccgggtac gcgcgcgcgt ccggccgcgt cggggtctgc       420
gtcgccacct ccggccccgg ggcaaccaac ctcgtgtccg cgctcgccga cgcgctgctc       480
gactccgtcc cgatggtcgc catcacgggc caggtccccc gccgcatgat cggcaccgac       540
gtcttccagg agacgcccat agtcgaggtc acccgctcca tcaccaagca caattacctt       600
gtccttgatg tggaggacat cccccgcgtc atacaggaag ccttcttcct cgcgtcctcg       660
ggccgtcctg gcccggtgct ggtcgacatc cccaaggaca tccagcagca gatggctgtg       720
ccagtctggg acacctcgat gaatctaccg gggtacattg cacgcctgcc caagccaccc       780
gcgacagaat tgcttgagca ggtcttgcgt ctggttggcg agtcacggcg cccgattctc       840
tatgtcggtg gtggctgctc tgcatctggt gatgaattgc gccggtttgt tgagctgacc       900
ggcatcccag ttacaaccac tctgatgggc ctcggcaatt tccccagtga tgatccgttg       960
tccctgcgca tgcttgggat gcatggcacg gtgtacgcaa attatgcggt ggataaggct      1020
gacctgttgc ttgcatttgg cgtgcggttt gatgatcgtg tgacagggaa aattgaggct      1080
tttgcaagca gggccaagat tgtgcacatt gacattgatc cagcggagat tggaaagaac      1140
aagcaaccac atgtgtcaat ttgcgcagat gttaagcttg ctttacaggg cttgaatgct      1200
ctgctagacc agagcacaac aaagacaagt tctgatttta gtgcgtggca caatgagttg      1260
gaccagcaga agagggagtt tcctctgggg tacaagactt ttggtgaaga gatcccaccg      1320
caatatgcta ttcaggtgct ggatgagctg acgaaagggg aggcaatcat cgctactggt      1380
gttggacagc accagatgtg ggcggcacaa tattacacct acaagcggcc acggcagtgg      1440
ctgtcttcgg ctggtctggg cgcaatggga tttgggctgc ctgctgcagc tggtgcttct      1500
gtggctaacc caggtgtcac agttgttgat attgatgggg atggtagctt cctcatgaac      1560
attcaggagt tggcattgat ccgcattgag aacctcccgg tgaaggtgat ggtgttgaac      1620
aaccaacatt tgggtatggt tgtgcaatgg gaggataggt tttacaaggc aaatagggcg      1680
catacatact tgggcaaccc agaatgtgag agtgagatat atccagattt tgtgactatt      1740
gctaaagggt tcaatattcc tgcagtccgt gtaacaaaga agagtgaagt ccgtgccgcc      1800
```

-continued atcaagaaga tgctcgatac cccagggcca tacttgttgg atatcatcgt cccacaccag    1860
gagcatgtgc tgcctatgat cccaagtggg ggcgcattca aggacatgat cctggatggt    1920
gatggcagga ctgtgtatta atctataatc tgtatgttgg c    1961

<210> SEQ ID NO 2
<211> LENGTH: 644
<212> TYPE: PRT
<213> ORGANISM: Oryza sativa

<400> SEQUENCE: 2

Met Ala Thr Thr Ala Ala Ala Ala Ala Ala Thr Leu Ser Ala Ala Ala
1               5                   10                  15

Thr Ala Lys Thr Gly Arg Lys Asn His Gln Arg His His Val Phe Pro
            20                  25                  30

Ala Arg Gly Arg Val Gly Ala Ala Ala Val Arg Cys Ser Ala Val Ser
        35                  40                  45

Pro Val Thr Pro Pro Ser Pro Ala Pro Pro Ala Thr Pro Leu Arg Pro
    50                  55                  60

Trp Gly Pro Ala Glu Pro Arg Lys Gly Ala Asp Ile Leu Val Glu Ala
65                  70                  75                  80

Leu Glu Arg Cys Gly Val Ser Asp Val Phe Ala Tyr Pro Gly Gly Ala
                85                  90                  95

Ser Met Glu Ile His Gln Ala Leu Thr Arg Ser Pro Val Ile Thr Asn
            100                 105                 110

His Leu Phe Arg His Glu Gln Gly Glu Ala Phe Ala Ala Ser Gly Tyr
        115                 120                 125

Ala Arg Ala Ser Gly Arg Val Gly Val Cys Val Ala Thr Ser Gly Pro
    130                 135                 140

Gly Ala Thr Asn Leu Val Ser Ala Leu Ala Asp Ala Leu Leu Asp Ser
145                 150                 155                 160

Val Pro Met Val Ala Ile Thr Gly Gln Val Pro Arg Arg Met Ile Gly
                165                 170                 175

Thr Asp Val Phe Gln Glu Thr Pro Ile Val Glu Val Thr Arg Ser Ile
            180                 185                 190

Thr Lys His Asn Tyr Leu Val Leu Asp Val Glu Asp Ile Pro Arg Val
        195                 200                 205

Ile Gln Glu Ala Phe Phe Leu Ala Ser Ser Gly Arg Pro Gly Pro Val
    210                 215                 220

Leu Val Asp Ile Pro Lys Asp Ile Gln Gln Gln Met Ala Val Pro Val
225                 230                 235                 240

Trp Asp Thr Ser Met Asn Leu Pro Gly Tyr Ile Ala Arg Leu Pro Lys
                245                 250                 255

Pro Pro Ala Thr Glu Leu Leu Glu Gln Val Leu Arg Leu Val Gly Glu
            260                 265                 270

Ser Arg Arg Pro Ile Leu Tyr Val Gly Gly Gly Cys Ser Ala Ser Gly
        275                 280                 285

Asp Glu Leu Arg Arg Phe Val Glu Leu Thr Gly Ile Pro Val Thr Thr
    290                 295                 300

Thr Leu Met Gly Leu Gly Asn Phe Pro Ser Asp Asp Pro Leu Ser Leu
305                 310                 315                 320

Arg Met Leu Gly Met His Gly Thr Val Tyr Ala Asn Tyr Ala Val Asp
                325                 330                 335

Lys Ala Asp Leu Leu Leu Ala Phe Gly Val Arg Phe Asp Asp Arg Val

-continued

```
          340              345              350
Thr Gly Lys Ile Glu Ala Phe Ala Ser Arg Ala Lys Ile Val His Ile
          355              360              365
Asp Ile Asp Pro Ala Glu Ile Gly Lys Asn Lys Gln Pro His Val Ser
          370              375              380
Ile Cys Ala Asp Val Lys Leu Ala Leu Gln Gly Leu Asn Ala Leu Leu
385              390              395              400
Asp Gln Ser Thr Thr Lys Thr Ser Ser Asp Phe Ser Ala Trp His Asn
                 405              410              415
Glu Leu Asp Gln Gln Lys Arg Glu Phe Pro Leu Gly Tyr Lys Thr Phe
                 420              425              430
Gly Glu Glu Ile Pro Pro Gln Tyr Ala Ile Gln Val Leu Asp Glu Leu
          435              440              445
Thr Lys Gly Glu Ala Ile Ile Ala Thr Gly Val Gly Gln His Gln Met
          450              455              460
Trp Ala Ala Gln Tyr Tyr Thr Tyr Lys Arg Pro Arg Gln Trp Leu Ser
465              470              475              480
Ser Ala Gly Leu Gly Ala Met Gly Phe Gly Leu Pro Ala Ala Ala Gly
                 485              490              495
Ala Ser Val Ala Asn Pro Gly Val Thr Val Val Asp Ile Asp Gly Asp
                 500              505              510
Gly Ser Phe Leu Met Asn Ile Gln Glu Leu Ala Leu Ile Arg Ile Glu
                 515              520              525
Asn Leu Pro Val Lys Val Met Val Leu Asn Asn Gln His Leu Gly Met
          530              535              540
Val Val Gln Trp Glu Asp Arg Phe Tyr Lys Ala Asn Arg Ala His Thr
545              550              555              560
Tyr Leu Gly Asn Pro Glu Cys Glu Ser Glu Ile Tyr Pro Asp Phe Val
                 565              570              575
Thr Ile Ala Lys Gly Phe Asn Ile Pro Ala Val Arg Val Thr Lys Lys
                 580              585              590
Ser Glu Val Arg Ala Ala Ile Lys Lys Met Leu Asp Thr Pro Gly Pro
                 595              600              605
Tyr Leu Leu Asp Ile Ile Val Pro His Gln Glu His Val Leu Pro Met
          610              615              620
Ile Pro Ser Gly Gly Ala Phe Lys Asp Met Ile Leu Asp Gly Asp Gly
625              630              635              640
Arg Thr Val Tyr

<210> SEQ ID NO 3
<211> LENGTH: 1932
<212> TYPE: DNA
<213> ORGANISM: Oryza sativa

<400> SEQUENCE: 3
atggctacga ccgccgcggc cgcggccgcc accttgtccg ccgccgcgac ggccaagacc     60
ggccgtaaga accaccagcg acaccacgtc tttcccgctc gaggccgggt gggggcggcg    120
gcggtcaggt gctcggcggt gtccccggtc accccgccgt ccccggcgcc gccggccacg    180
ccgctccggc cgtgggggcc ggccgagccc cgcaagggcg cggacatcct cgtggaggcg    240
ctggagcggt cggcgtcag cgacgtgttc gcctacccgg cggcgcgcgtc catggagatc    300 caccaggcgc tgacgcgctc cccggtcatc accaaccacc tcttccgcca cgagcagggc    360
gaggcgttcg cggcgtccgg gtacgcgcgc gcgtccggcc gcgtcggggt ctgcgtcgcc    420
```

```
acctccggcc ccggggcaac caacctcgtg tccgcgctcg ccgacgcgct gctcgactcc        480
gtcccgatgg tcgccatcac gggccaggtc ccccgccgca tgatcggcac cgacgtcttc        540
caggagacgc ccatagtcga ggtcacccgc tccatcacca agcacaatta ccttgtcctt        600
gatgtggagg acatcccccg cgtcatacag gaagccttct tcctcgcgtc ctcgggccgt        660
cctggcccgg tgctggtcga catccccaag gacatccagc agcagatggc tgtgccagtc        720
tgggacacct cgatgaatct accggggtac attgcacgcc tgcccaagcc acccgcgaca        780
gaattgcttg agcaggtctt gcgtctggtt ggcgagtcac ggcgcccgat tctctatgtc        840
ggtggtggct gctctgcatc tggtgatgaa ttgcgccggt ttgttgagct gaccggcatc        900
ccagttacaa ccactctgat gggcctcggc aatttcccca gtgatgatcc gttgtccctg        960
cgcatgcttg ggatgcatgg cacggtgtac gcaaattatg cggtggataa ggctgacctg       1020
ttgcttgcat ttggcgtgcg gtttgatgat cgtgtgacag ggaaaattga ggcttttgca       1080
agcagggcca agattgtgca cattgacatt gatccagcgg agattggaaa gaacaagcaa       1140
ccacatgtgt caatttgcgc agatgttaag cttgctttac agggcttgaa tgctctgcta       1200
gaccagagca caacaaagac aagttctgat tttagtgcgt ggcacaatga gttggaccag       1260
cagaagaggg agtttcctct ggggtacaag acttttggtg aagagatccc accgcaatat       1320
gctattcagg tgctggatga gctgacgaaa ggggaggcaa tcatcgctac tggtgttgga       1380
cagcaccaga tgtgggcggc acaatattac acctacaagc ggccacggca gtggctgtct       1440
tcggctggtc tgggcgcaat gggatttggg ctgcctgctg cagctggtgc ttctgtggct       1500
aacccaggtg tcacagttgt tgatattgat ggggatggta gcttcctcat gaacattcag       1560
gagttggcat tgatccgcat tgagaacctc ccggtgaagg tgatggtgtt gaacaaccaa       1620
catttgggta tggttgtgca atgggaggat aggtttttaca aggcaaatag ggcgcataca       1680
tacttgggca acccagaatg tgagagtgag atatatccag attttgtgac tattgctaaa       1740
gggttcaata ttcctgcagt ccgtgtaaca aagaagagtg aagtccgtgc cgccatcaag       1800
aagatgctcg ataccccagg gccatacttg ttggatatca tcgtcccaca ccaggagcat       1860
gtgctgccta tgatcccaag tgggggcgca ttcaaggaca tgatcctgga tggtgatggc       1920
aggactgtgt at                                                          1932
```

```
<210> SEQ ID NO 4
<211> LENGTH: 19
<212> TYPE: DNA
<213> ORGANISM: Artificial Sequence
<220> FEATURE:
<223> OTHER INFORMATION: PCR amplification and sequencing primer U136851

<400> SEQUENCE: 4
gacatatggg gcccactgt                                                     19

<210> SEQ ID NO 5
<211> LENGTH: 19
<212> TYPE: DNA
<213> ORGANISM: Artificial Sequence
<220> FEATURE:
<223> OTHER INFORMATION: PCR amplification and sequencing primer L789

<400> SEQUENCE: 5
gtagattcat cgaggtgtc                                                     19

<210> SEQ ID NO 6
```

-continued

```
<211> LENGTH: 20
<212> TYPE: DNA
<213> ORGANISM: Artificial Sequence
<220> FEATURE:
<223> OTHER INFORMATION: PCR amplification and sequencing primer U642

<400> SEQUENCE: 6
gtccttgatg tggaggacat                                              20

<210> SEQ ID NO 7
<211> LENGTH: 20
<212> TYPE: DNA
<213> ORGANISM: Artificial Sequence
<220> FEATURE:
<223> OTHER INFORMATION: PCR amplification and sequencing primer L1369

<400> SEQUENCE: 7
catattgcgg tgggatctct                                              20

<210> SEQ ID NO 8
<211> LENGTH: 20
<212> TYPE: DNA
<213> ORGANISM: Artificial Sequence
<220> FEATURE:
<223> OTHER INFORMATION: PCR amplification and sequencing primer U1229

<400> SEQUENCE: 8
gggcttgaat gctctgctac                                              20

<210> SEQ ID NO 9
<211> LENGTH: 20
<212> TYPE: DNA
<213> ORGANISM: Artificial Sequence
<220> FEATURE:
<223> OTHER INFORMATION: PCR amplification and sequencing primer L1742

<400> SEQUENCE: 9
cgggttgccc aagtatgtat                                              20

<210> SEQ ID NO 10
<211> LENGTH: 20
<212> TYPE: DNA
<213> ORGANISM: Artificial Sequence
<220> FEATURE:
<223> OTHER INFORMATION: PCR amplification and sequencing primer U1633

<400> SEQUENCE: 10
acctccctgt gaaggtgatg                                              20

<210> SEQ ID NO 11
<211> LENGTH: 20
<212> TYPE: DNA
<213> ORGANISM: Artificial Sequence
<220> FEATURE:
<223> OTHER INFORMATION: PCR amplification and sequencing primer L2155

<400> SEQUENCE: 11
aggattacca tgccaagcac                                              20

<210> SEQ ID NO 12
<211> LENGTH: 18
<212> TYPE: DNA
<213> ORGANISM: Artificial Sequence
<220> FEATURE:
<223> OTHER INFORMATION: PCR amplification and sequencing primer U037

<400> SEQUENCE: 12
```

```
caccacccac catggcta                                              18

<210> SEQ ID NO 13
<211> LENGTH: 18
<212> TYPE: DNA
<213> ORGANISM: Artificial Sequence
<220> FEATURE:
<223> OTHER INFORMATION: PCR amplification and sequencing primer U114

<400> SEQUENCE: 13
gtaagaacca ccagcgac                                              18

<210> SEQ ID NO 14
<211> LENGTH: 19
<212> TYPE: DNA
<213> ORGANISM: Artificial Sequence
<220> FEATURE:
<223> OTHER INFORMATION: PCR amplification and sequencing primer U1109

<400> SEQUENCE: 14
gtggataagg ctgacctgt                                             19

<210> SEQ ID NO 15
<211> LENGTH: 21
<212> TYPE: DNA
<213> ORGANISM: Artificial Sequence
<220> FEATURE:
<223> OTHER INFORMATION: PCR amplification and sequencing primer U1166

<400> SEQUENCE: 15
gggaaaattg aggcttttgc a                                          21

<210> SEQ ID NO 16
<211> LENGTH: 20
<212> TYPE: DNA
<213> ORGANISM: Artificial Sequence
<220> FEATURE:
<223> OTHER INFORMATION: PCR amplification and sequencing primer L1299

<400> SEQUENCE: 16
ctcattgtgc catgcactaa                                            20

<210> SEQ ID NO 17
<211> LENGTH: 19
<212> TYPE: DNA
<213> ORGANISM: Artificial Sequence
<220> FEATURE:
<223> OTHER INFORMATION: PCR amplification and sequencing primer U1721

<400> SEQUENCE: 17
gcatacatac ttgggcaac                                             19

<210> SEQ ID NO 18
<211> LENGTH: 20
<212> TYPE: DNA
<213> ORGANISM: Artificial Sequence
<220> FEATURE:
<223> OTHER INFORMATION: PCR amplification and sequencing primer L2054

<400> SEQUENCE: 18
cataccactc tttatgggtc                                            20

<210> SEQ ID NO 19
<211> LENGTH: 19
<212> TYPE: PRT
```

-continued

```
<213> ORGANISM: Artificial Sequence
<220> FEATURE:
<223> OTHER INFORMATION: Conserved region

<400> SEQUENCE: 19

Val Phe Ala Tyr Pro Gly Gly Ala Ser Met Glu Ile His Gln Ala Leu
1               5                   10                  15

Thr Arg Ser

<210> SEQ ID NO 20
<211> LENGTH: 13
<212> TYPE: PRT
<213> ORGANISM: Artificial Sequence
<220> FEATURE:
<223> OTHER INFORMATION: Conserved region

<400> SEQUENCE: 20

Ala Ile Thr Gly Gln Val Pro Arg Arg Met Ile Gly Thr
1               5                   10

<210> SEQ ID NO 21
<211> LENGTH: 6
<212> TYPE: PRT
<213> ORGANISM: Artificial Sequence
<220> FEATURE:
<223> OTHER INFORMATION: Conserved region

<400> SEQUENCE: 21

Ala Phe Gln Glu Thr Pro
1               5

<210> SEQ ID NO 22
<211> LENGTH: 4
<212> TYPE: PRT
<213> ORGANISM: Artificial Sequence
<220> FEATURE:
<223> OTHER INFORMATION: Conserved region

<400> SEQUENCE: 22

Gln Trp Glu Asp
1

<210> SEQ ID NO 23
<211> LENGTH: 5
<212> TYPE: PRT
<213> ORGANISM: Artificial Sequence
<220> FEATURE:
<223> OTHER INFORMATION: Conserved region

<400> SEQUENCE: 23

Ile Pro Ser Gly Gly
1               5
```